United States Patent
Hansson et al.

(10) Patent No.: US 12,162,824 B2
(45) Date of Patent: *Dec. 10, 2024

(54) SUCCINATE PRODRUG, COMPOSITIONS CONTAINING THE SUCCINATE PRODRUG AND USES THEREOF

(71) Applicant: ABLIVA AB, Lund (SE)

(72) Inventors: Magnus Joakim Hansson, Landskrona (SE); Alvar Grönberg, Knivsta (SE); Mats Eskil Elmér, Lund (SE); Mark Richard Farmery, Södertälje (SE); Steven James Moss, Cambridge (GB); Lee Robert Webster, Cambridge (GB); Matthew Alan Gregory, Cambridge (GB)

(73) Assignee: ABLIVA AB, Lund (SE)

( * ) Notice: Subject to any disclaimer, the term of this patent is extended or adjusted under 35 U.S.C. 154(b) by 177 days.

This patent is subject to a terminal disclaimer.

(21) Appl. No.: 17/944,751

(22) Filed: Sep. 14, 2022

(65) Prior Publication Data

US 2023/0033294 A1 Feb. 2, 2023

Related U.S. Application Data

(63) Continuation of application No. 17/615,408, filed as application No. PCT/EP2020/066923 on Jun. 18, 2020, now Pat. No. 11,565,998.

(30) Foreign Application Priority Data

Jun. 19, 2019 (DK) .............................. PA201970382
Jun. 19, 2019 (DK) .............................. PA201970383
Jun. 19, 2019 (DK) .............................. PA201970384

(51) Int. Cl.
*C07C 327/30* (2006.01)
*A61P 3/00* (2006.01)

(52) U.S. Cl.
CPC .............. *C07C 327/30* (2013.01); *A61P 3/00* (2018.01)

(58) Field of Classification Search
CPC .................................................... C07C 327/30
See application file for complete search history.

(56) References Cited

U.S. PATENT DOCUMENTS

| 10,307,389 | B2  |   | 6/2019 | Elmer et al. |
|------------|-----|---|--------|--------------|
| 11,565,998 | B2  | * | 1/2023 | Hansson ................. A61P 25/16 |
| 2017/0100359 | A1 |   | 4/2017 | Elmer et al. |
| 2017/0105961 | A1 |   | 4/2017 | Elmer et al. |

FOREIGN PATENT DOCUMENTS

| WO | 2015155231 A1 | 10/2015 |
|----|---------------|---------|
| WO | 2015155238 A1 | 10/2015 |

OTHER PUBLICATIONS

Murli, S., et al., "Chemobiosynthesis of Novel 6-Deoxyerythronolide B Analogues by Mutation of the Loading Module pf 6-Deoxyerhtronolide B Synthase 1" Applied and Environmental Microbiology (2005) 71:4503-4509.
Protti, A., "Succinate and the shortcut to the cure of metformin-induced lactic acidosis" Intensive Care Med. Exp. (2018) 6(1):35.
Ehinger, J.K., et al., "Cell-permeable succinate prodrugs bypass mitochondrial complex I deficiency" Nat. Commun. (2016) 7:12317.
Murli, S., et al., CAS, 143:365702 (2005).

* cited by examiner

*Primary Examiner* — Rei Tsang Shiao
(74) *Attorney, Agent, or Firm* — Robert C. Netter, Jr.; Dann, Dorfman, Herrell & Skillman

(57) ABSTRACT

The present invention provides a novel isolated succinate prodrug as the free compound or a salt, hydrate, solvate or complex thereof being cell permeable and aimed for increasing the ATP-production in mitochondria. The compound is useful in the medical treatment of a range of diseases, in nutritional supplements, nutricosmetics and in cosmetics.

14 Claims, 26 Drawing Sheets

SUCCINATE PRODRUG, COMPOSITIONS CONTAINING THE SUCCINATE PRODRUG AND USES THEREOF

This application is a continuation application of U.S. patent application Ser. No. 17/615,408, filed Nov. 30, 2021, which is a § 371 application of PCT/EP2020/066923, filed Jun. 18, 2020, which in turn claims priority to DK Application PA 201970382, filed Jun. 19, 2019; DK Application PA 201970383, filed Jun. 19, 2019; and DK Application PA 201970384, filed Jun. 19, 2019. The entire disclosure of each of the foregoing applications is incorporated by reference herein.

FIELD OF THE INVENTION

The present invention relates to the fields of chemistry, pharmacologically active compounds, pharmaceutical compositions comprising such compounds and nutrition. Specifically, the invention relates to cell-permeable precursors of succinates useful as medicines and nutritional supplements.

BACKGROUND OF THE INVENTION

Mitochondria are organelles in eukaryotic cells that generate most of the cell's supply of adenosine triphosphate (ATP), which is used as an energy source. Thus, mitochondria are indispensable for energy production, for the survival of eukaryotic cells and for correct cellular function. In addition to supplying energy, mitochondria are involved in a number of other processes such as redox and ion balance, cell signalling, cellular differentiation, cell death as well as the control of the metabolic processes, cell cycle and cell growth. In particular, mitochondria are crucial regulators of cell apoptosis and they also play a major role in multiple forms of non-apoptotic cell death such as necrosis.

Mitochondrial dysfunction contributes to a wide variety of diseases and can be caused by mutations or deletions in the mitochondrial or nuclear genome, primary or secondary impairment of the mitochondrial respiratory system or other mechanisms related to abnormal mitochondrial function. At present there is no available treatment that can cure mitochondrial diseases.

The oxidation of nutrients to produce usable chemical energy in the form of ATP occurs to a large extent in the mitochondria through a series of chemical reactions in the tricarboxylic acid cycle and the electron transport chain. NADH generated in the tricarboxylic acid cycle feeds into complex I in the electron transport chain. Succinate is a metabolic intermediate of the tricarboxylic acid cycle in mitochondria and is unique by being directly metabolized by the enzyme succinate dehydrogenase of complex II in the electron transport chain. Succinate can also act as a signaling molecule reflecting the cellular metabolic state.

In view of the recognized importance of maintaining or restoring a normal mitochondrial function or of enhancing the cell's energy production (ATP) in the treatment of disease and conditions related to mitochondrial dysfunction or the enhancement of mitochondrial function, there is a need for compounds having cell permeability, the ability to liberate intracellular succinate or a precursor of succinate, low toxicity of the compound and intracellularly released by-products, and physicochemical properties consistent with administration to a subject or patient.

Succinate compounds have been prepared as prodrugs of other active agents, for example WO 2002/28345 describes succinic acid bis (2,2-dimethylpropionyloxymethyl) ester, succinic acid dibutyryloxymethyl ester and succinic acid bis-(1-butyryloxy-ethyl)ester. These compounds as prepared deliver formaldehyde, and are aimed at different medical uses compared to the current compounds.

Various succinate ester compounds are known in the art.

WO97/47584 discloses polyol succinates comprising multiple succinate moieties linked together.

WO2015/155231 discloses succinates and precursors of succinate which are cell permeable.

Murli et al. (Appl. Environ. Microbiol. 71:2005:4503-4509) discloses the attempted chemo-biosynthesis of 6-deoxyerythronolide B analogues by feeding the bacteria *Escherichia coli* and *Streptomyces coelicolor* acyl-thioesters. A table of structures discloses various acylthioesters including the formal structure of methyl 3-[(2-acetylamino-ethylthio)carbonyl]propionate but synthesis failed and did not give the desired product.

There is a need for effective and safe new treatment options for diseases having their origin in mitochondrial dysfunction or for enhancing metabolism by delivering a substrate of metabolism. There is also a need for new nutritional supplements, nutricosmetics, cosmeceuticals and cosmetics for stimulating energy in a subject and for serving as antioxidant. Such new treatments, nutritional supplements, nutricosmetics, cosmeceuticals and cosmetics are required to have attractive combinations of properties including high activity to enhance mitochondrial energy production and or to serve as anti-oxidant, good bioavailability, long plasma half-life, stability when formulated into a product and low toxicity. In particular there is a need for such new treatments, nutritional supplements, nutricosmetics cosmeceuticals and cosmetics that are based on an active ingredient having a high solubility in water, good cell permeability and when desirable a high blood brain barrier penetration and/or gives reduced lactate production.

SUMMARY OF THE INVENTION

In a first aspect the present invention provides isolated Methyl 3-[(2-acetylaminoethyl-thio)carbonyl]propionate (Compound 1) in solid form. It may be in the free form or a salt, hydrate, solvate or complex thereof.

Compound 1 has the structure (formula 1):

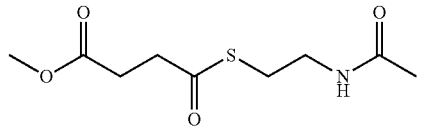

It has now surprisingly been found that the cell permeable Compound 1 has a remarkable combination of advantageous properties. It has potent in vivo activity of stimulating the energy production in mitochondria and has good oral bioavailability, blood brain barrier penetration, good plasma stability, and decrease lactate production and restores succinate levels. Simultaneously, Compound 1 possesses remarkably high solubility in water and aqueous systems. Solubility assessment has shown solubilities in excess of 500 mg/mL, which equates to ~2.1 M. This extremely high aqueous solubility likely comes from the low melting point of Compound 1 (less than 55° C.), and on addition of aqueous solvent it is miscible with the aqueous solvent. This enables very high concentration of aqueous formulations, allowing for high oral dosing of a compound which is in effect a prodrug of a substrate for metabolism.

In an embodiment the isolated Compound 1 is a solid product with a melting point or melting range in the range of from about 35° C. to about 55° C. In preferred embodiments the isolated Compound 1 has a purity of at least 80% w/w, such as at least 85% w/w, at least 90% w/w, such as at least 95% w/w, but it may also have a lower purity such as at least 30% w/w, at least 40% w/w, at least 45% ww, at least 50% w/w, at least 55% w/w, at least 60% w/w, at least 65% w/w, at least 70% w/w or at least 75% w/w. Dependent on the manufacturing method and the storage conditions, Compound 1 may comprise crystals and/or it may comprise non-crystals such as amorphous forms of Compound 1, and mixtures thereof. As seen from the Examples herein, all methods used lead to Compound 1 with a degree of crystallinity.

It is contemplated that more than one crystal form of Compound 1 may exist and Compound 1 may also exist as an amorphous solid'. In the present context, all forms of Compound 1 is within the scope of the present application including mixtures of two of more forms of Compound 1. Thus, the term "Compound 1" denotes a compound of formula 1 in solid form, but irrespective of whether the compound is in a crystalline form, in an amorphous form, in a polymorphous form in powder form or in mixtures thereof.

In particular, it has been found that Compound 1 has a number of solid forms with differing properties. For example, as an amorphous solid or as a mainly amorphous solid, it shows higher kinetic solubility. It also has crystalline forms (or mainly crystalline forms) which have been generated and show other improved properties when handled as a solid form. It has also been found that the purity affects the properties of the preparation. In particular, the melting point is low and close to body temperature and is altered by the presence of impurities. The stability of Compound 1 preparations is also altered by the presence of impurities, such as those in non-purified water, which reduce the stability of Compound 1.

In a second aspect the present invention provides a composition comprising isolated Compound 1.

In a third aspect the present invention provides a cosmeceutical comprising the isolated Compound 1.

In a fourth aspect the present invention provides a nutricosmetics comprising the isolated Compound 1.

In a fifth aspect the present invention provides a process for preparing isolated Compound 1, said process comprising the steps of:
a) reacting N-acetyl cysteamine and monomethyl succinate, in the presence of a coupling reagent, in organic solvent, between 0° C. and 100° C.
b) isolating Compound 1,
so as to provide isolated Compound 1.

The method normally includes a purification step to increase the purity of the compound.

The Compound 1 compounds of the invention can be used to enhance or restore energy production in mitochondria. Notably the compounds can be used in medicine, nutricosmetics, nutritional supplements, cosmeceuticals and in cosmetics. The Compound 1 compounds can be used in the prevention or treatment of disorders or diseases having a component relating to mitochondrial dysfunction and/or to a component of energy (ATP) deficiency as well as to utilize the cell signalling properties of succinate and its anaplerotic effects on metabolic intermediates.

In addition, in comparison with known succinate prodrugs (such as e.g. mentioned in WO 97/47584), the isolated Compound 1 of the present invention shows improved properties for treatment and for use as nutritional supplement and cosmetic product, including better cell permeability, longer plasma half-life, good oral bioavailability, reduced toxicity, increased energy release to mitochondria, and improved formulation properties e.g. due to improved solubility in water.

In another aspect, the invention provides a pharmaceutical composition comprising Compound 1 compounds.

The pharmaceutical composition may be a solid formulation or it may be a solid formulation for reconstitution prior to use.

Alternatively, it may be in the form of a liquid such a an aqueous solution including e.g. an aqueous Phosphate Buffered Saline (PBS) formulation. In general, a pharmaceutical composition of the invention has a concentration of Compound 1 of at least 10% w/w, at least 30% w/w, at least 50% w/w, at least 60% or at least 70% w/w. In an embodiment, the pharmaceutical composition is a solution of Compound 1 in purified water optionally made isotonic with the blood.

In another aspect the present invention provides the use of Compound 1 of a composition thereof in the treatment or prevention of a metabolic disease, a disease of mitochondrial dysfunction, a disease related to mitochondrial dysfunction, a mitochondrial disorder, mitochondrial energy deficiency, drug-induced mitochondrial side effects, cancer, diabetes, traumatic brain injury, acute liver injury and atrial fibrillation.

In an aspect the present invention provides a process for preparing a pharmaceutical composition comprising Compound 1.

DESCRIPTION OF THE INVENTION

Figure 1:
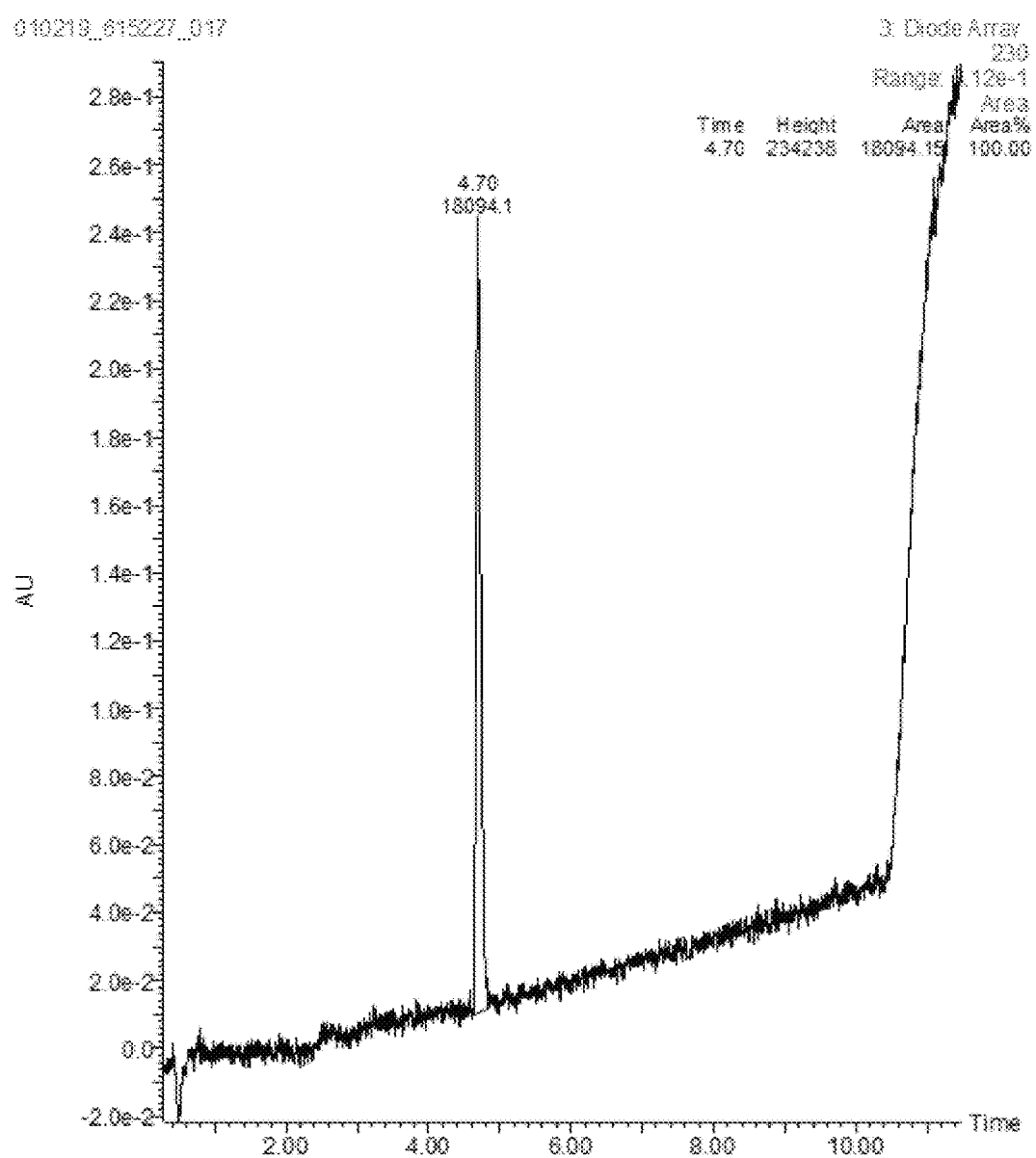
FIG. 1. LCMS analysis of Compound 1 Batch 3 depicting Absorbance Unit (AU) versus time using HPLC Method 2.

In a first aspect the present invention provides isolated Methyl 3-[(2-acetylaminoethyl-thio)carbonyl]propionate (Compound 1) in solid from. It may be in the free form or a salt, hydrate, solvate or complex thereof.

Compound 1 has the structure (formula 1):

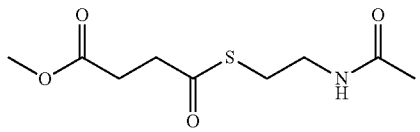

As mentioned above, Compound 1 may be in the form of a salt. Suitable salts include pharmaceutically acceptable salts such as hydrochloride salt, hydrobromide salt, acetate, citrate, lactate, maleate, malonate or the like.

Compound 1 may also be a solvate. Suitable solvates may include hydrates, ethanolates Compound 1 may also be in the form of a complex. Examples of suitable complexes may be Compound 1 complexed with cyclodextrin, lipids, triglycerides, carbohydrates, PVA, In an embodiment the isolated Compound 1 is a solid product with a melting point or melting range in the range of from about 35° C. to about 55° C. As seen from the examples herein Compound 1 has been provided with different melting points most likely dependent on the content of different forms of Compound 1 such as crystal forms, amorphous forms etc. In particular, melting points in the range of from 39 to 51° C. have been found such as melting points of 39° C. and melting points in the range of from 46 to 51° C. such as about 46-47° C., 48-49° C. and 50-51° C.

In preferred embodiments the isolated Compound 1 has a purity of at least 80% w/w, such as at least 85% w/w, at least 90% w/w, such as at least 95% w/w or at least 97% w/w, but it may also have a lower purity such as at least 30% w/w, at least 40% w/w, at least 45% ww, at least 50% w/w, at least 55% w/w, at least 60% w/w, at least 65% w/w, at least 70% w/w or at least 75% w/w. Dependent on the manufacturing method and the storage conditions, Compound 1 may comprise crystals and/or it may comprise non-crystals such as amorphous forms of Compound 1, and mixtures thereof. As seen from the Examples herein, all methods used lead to Compound 1 with a degree of crystallinity. Compound 1 may also appear as a powder.

As seen from the Examples herein, Compound 1 has an excellent water solubility at room temperature (20-25° C.). At pH 7.4 and in the aqueous media tested in the examples, Compound 1 has an aqueous solubility of at least 300 mg/mL. The aqueous solubility of Compound 1 is dependent on the crystallinity of the Compound; thus the lower degree of crystallinity, the higher aqueous solubility. As seen from Example 10 herein a mainly amorphous material may have an aqueous solubility of 850 mg/mL. It is therefore contemplated that the aqueous solubility of Compound 1 is in a range of from 300 mg/mL to about 900 mg/mL.

The kinetic solubility has also been determined and the rate constants for the kinetic solubility have been found to be in a range of from 0.005 to 0.2 s$^{-1}$, such as in a range of from 0.01 to 0.15 s$^{-1}$. The kinetic solubility may depend on various factors such as particle size, crystallinity, content of amorphous material etc.

Regarding the crystallinity of Compound 1 it may have a degree of crystallinity in a range of from 0% to 100% such as from 10% to 100%, from 20% to 100%, from 30% to 100%, from 40% to 100%, from 50% to 100%, from 60% to 100%. As seen from the Examples herein many of the batches prepared by the method described herein have a crystallinity of at least 50% such as in a range of from about 50% to about 80%.

As seen from the XRPD data in the examples, crystals of Compound 1 are characterized by having an X-ray powder diffraction pattern with signals at 21.4, 22.2, 22.8, 23.1 and 23.3 (±0.2 degrees, 2-theta values).

Crystals of Compound 1 may also have one or more signals at 10.9, 13.1, 14.9, 16.2, 20.1, 24.0, 24.8, 26.1, such as two or more, three or more, four or more, six or more, seven or more, or eight. As seen from the examples, almost all the tested compounds have signals at these degrees (±0.2 degrees, 2-theta values).

From the data in the Examples it is contemplated that signals at 11.1 and 16.9 (±0.2 degrees, 2-theta values) relate to a polymorphous form of Compound 1 (Form 1). Thus, crystals of Compound 1 may have an X-ray powder diffraction pattern with signals at 11.1 and 16.9 (±0.2 degrees, 2-theta values), either in complement to one or more of the signals mentioned above, or in the alternative.

As mentioned above, Compound 1 is in solid form notably comprising crystals of the compound. The melting point is rather low, but it is advantageous that Compound 1 is not in the form of an oil. First of all, it will be easier to handle Compound 1 in manufacturing of pharmaceutical/cosmeceutical composition (eg millability, bulk powder flow and compressibility). Secondly, the crystalline form is normally the most stable form and non-crystalline (less ordered) material tends to change form to crystalline (more ordered, lower energy) over time.

Definitions

The term "Compound 1" denotes a compound of formula 1 in solid form and the term includes all crystalline forms, all amorphous forms, all polymorphous forms, and mixtures thereof including mixtures within the same form or within different forms. Compound 1 may also be in powder form.

The term "purity" as used herein in relation to Compound 1 means the degree to which a Compound 1 composition is methyl 3-[(2-acetylaminoethylthio)carbonyl]propionate (Compound 1) relative to the total of Compound 1 and the related impurities being by-products, aberrant forms of Compound 1 (closely related structure) and synthesis precursors for Compound 1. Hence, in a composition containing 10% w/w Compound 1, the purity of said Compound 1 may be e.g. 95% w/w or 50% w/w, meaning that the Compound 1 used to make said composition has a purity of 95% w/w or 50% w/w, respectively. Purity can be assessed by one of a number of methods including qNMR, HPLC etc. In qNMR a known amount of analyte is dissolved in NMR solvent with a known amount of internal standard. A $^1$H NMR spectrum is obtained, with sufficient scans to reduce the signal to noise ratio. An exemplary resonance in the internal standard and the analyte are integrated. The ratio of these integrals, coupled with the knowledge of how many protons the signal is comprised and the molecular weights of both analyte and internal standard, is then used to determine the purity in a w/w %. In HPLC the purity is assessed as the area under curve (AUC) for the analyte in comparison to other signals with different retention times.

The term "isolated" as used herein in relation to Compound 1 means the Compound 1 product methyl 3-[(2-acetylaminoethylthio)carbonyl]propionate as obtained from a synthesis reaction and isolated e.g. by purification from various by-products, synthesis precursors and aberrant Compound 1 forms.

The term 'nutricosmetics' as used herein refers to nutritional supplements or cosmetics specifically formulated to help maintain healthy skin, hair and nails with active ingredients that support physiological functions to achieve a healthier and more youthful appearance over time. Unlike a topical cream or treatment, nutricosmetics are taken orally and work from the inside to promote healthy skin, hair or nails from within.

The term "cosmeceutical" as used herein is intended to mean a cosmetic product with bioactive ingredients purported to have medical benefits. Cosmeceutical products are marketed as cosmetics, but reputedly contain at least one biologically active ingredient. Examples of cosmeceuticals include anti-wrinkle skin creams with ingredients such as alpha lipoic acid and dimethylaminoethanol and creams containing "cellular replenishment serum" that are stated as having "antiaging properties".

The term "treatment" as used herein is intended to mean implementation of therapy with the intention of reducing the severity or frequency of symptoms. As used herein the term "treatment" refers to both therapeutic treatment and prophylactic or preventive measures.

The term "prevention" as used herein is intended to mean preventing in whole or in part, or ameliorating, reducing or controlling.

Compound 1 is generically covered by the Formula (I) of WO2015/155231 disclosing succinates and precursors of succinate which are cell permeable. However, with the identification of Compound I the inventors made a number of new surprising discoveries revealing that it has unexpected good combination of properties that make it suitable for a number of therapeutic and non-therapeutic uses. Additionally, surprising discoveries have been made around the advantages of certain forms and formulations of Compound I.

General Use of the Compounds of the Invention

Methyl 3-[(2-acetylaminoethylthio)carbonyl]propionate (Compound 1) being the free form or a salt, hydrate, solvate or complex thereof as described herein can be used in medicine, notably in the medical treatment or prevention of a mitochondria-related condition, disease or disorder, in nutricosmetics or in cosmetics. Compound I can also be used in the manufacture of a composition for such medical treatment, or prevention, nutricosmetics or cosmetics. The Compound 1 or a salt, hydrate, solvate or a complex thereof can be used in any situation where an enhanced or restored energy production (ATP) is desired, such as in the medical treatment of a disease. The medical treatment may be of metabolic diseases, or in the treatment of diseases or conditions of mitochondrial dysfunction or diseases associated with reduced levels of succinate or functional activity of succinate, or disease where the anaplerotic effect of succinate or its signaling properties are useful, treating or suppressing mitochondrial disorders. The Compound 1 compounds may be used in the stimulation of mitochondrial energy production and in the restoration of drug- or chemically induced mitochondrial dysfunction such as e.g. sensineural hearing loss or tinnitus (side effect of certain antibiotics due to mitochondrial toxicity), poisoning with chemicals or gasses affecting mitochondrial metabolism, or lactic acidosis. The compounds may be used in the treatment of cancer, diabetes, acute starvation, endotoxemia, sepsis, systemic inflammatory response syndrome, multiple organ dysfunction syndrome and following hypoxia, ischemia, stroke, myocardial infarction, acute angina, an acute kidney injury, coronary occlusion and atrial fibrillation, or to avoid or counteract reperfusion injuries. Moreover, it is envisaged that the compounds of the invention may be beneficial in treatment of male infertility and menopausal symptoms in women.

It is envisaged that the Compound 1 compounds of the invention will provide cell-permeable precursors of components of the Kreb's cycle and optionally glycolysis pathways. It is envisaged that following entry into the cell, enzymatic or chemical hydrolysis will liberate succinate. This hydrolysis of Compound 1 is also regarded as especially advantageous as the thiol group released has reductive properties. Many diseases have an unwanted oxidative stress component, which may lead to damage to cell structure and cell function. Also, oxidative stress is believed to be involved in ageing processes. Accordingly, release of a component which can act as an antioxidant and scavenge free radicals or reduce oxygen-reactive species is expected to give extra benefit in both medical, nutricosmetic and cosmetic use.

Compound 1 can be used to enhance or restore energy production in mitochondria. Compound 1 can also be used as an antioxidant and scavenge free radicals or reduce oxygen-reactive species. Compound 1 can be used in the prevention or treatment of disorders or diseases having a component relating to mitochondrial dysfunction and/or to a component of energy (ATP) deficiency, as well as diseases associated with reduced levels of succinate or functional activity of succinate, or diseases where the anaplerotic effect of succinate or its signaling properties are useful.

Enhancement of energy production is e.g. relevant in subjects suffering from a mitochondrial defect, disorder or disease. Mitochondrial diseases result from dysfunction of the mitochondria, which are specialized compartments present in every cell of the body except red blood cells. When mitochondrial function decreases, the energy generated within the cell is reduced and cell injury or cell death will follow.

Diseases of the mitochondria appear most often in organs that are very energy demanding such as retina, the cochlea, the brain, heart, liver, skeletal muscles, kidney and the endocrine and respiratory system. Symptoms of a mitochondrial disease may include loss of motor control, muscle weakness and pain, seizures, visual/hearing problems, cardiac diseases, liver diseases, gastrointestinal disorders, swallowing difficulties, fatigue and more. A mitochondrial disease may be inherited or may be due to spontaneous mutations, which lead to altered functions of the proteins or RNA molecules normally residing in the mitochondria. Many diseases have been found to involve a mitochondrial deficiency such as a Complex I, II, III or IV deficiency or an enzyme deficiency like e.g. pyruvate dehydrogenase deficiency. However, the picture is complex, and many factors may be involved in the diseases.

Up to now, no curative treatments are available. The only treatments available are such that can alleviate the symptoms and delay the progression of the disease.

Accordingly, the findings by the present inventors and described herein are very important as they demonstrate the beneficial effect of the cell permeable Compound 1 being a thioester prodrug of succinic acid on the energy production in the mitochondria.

In addition, in comparison with known succinate prodrugs (such as e.g. mentioned in WO 97/47584), the isolated Compound 1 compounds of the present invention show improved properties for medical treatment and use as nutricosmetics, nutritional supplement, cosmeceutical and cosmetic product, including better cell permeability, longer plasma half-life, reduced toxicity, increased energy release to mitochondria, and improved formulation (due to improved properties including increased solubility). In some cases, the isolated Compound 1 compounds are also orally bioavailable, which allows for easier administration.

Thus, the advantageous properties of the isolated compound of the invention may include one or more of the following:
Increased cell permeability
Increased oral bioavailability
Longer half-life in plasma
Reduced toxicity
Increased energy release to mitochondria
Increased antioxidant activity
Improved formulation
Increased solubility The present invention provides Compound 1 for use as in medicine, as a pharmaceutically active substance, in particular in the treatment of cellular energy (ATP)-deficiency.

A compound of the invention may be used in the treatment of complex I impairment, either dysfunction of the complex itself or any condition or disease that limits the supply of NADH to Complex I, e.g. dysfunction of Krebs cycle, glycolysis, beta-oxidation, pyruvate metabolism and even transport of glucose or Complex-I-related substrates.

The present invention also provides a method of treatment of mitochondrial complex I related disorders such as but not limited to, Leigh Syndrome, Leber's hereditary optic neuropathy (LHON), MELAS (mitochondrial encephalomyopathy, lactic acidosis, and strokelike episodes), mitochondrial deletion syndromes, mitochondrial myopathies and MERRF (myoclonic epilepsy with ragged red fibers), which comprises administering to a subject in need thereof an effective amount of the compound of the invention.

The present invention also provides the use of the compounds of the invention for the manufacture of a medicament for the treatment of toxin- or drug-induced lactic acidosis/mitochondrial dysfunction.

Isolated Compound 1 may also be useful in any condition where extra energy production would potentially be beneficial such as, but not limited to, prolonged surgery and intensive care.

Mitochondria

Mitochondria are organelles in eukaryotic cells, popularly referred to as the "powerhouse" of the cell. One of their primary functions is oxidative phosphorylation. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Kreb's cycle), which generates reduced nicotinamide adenine dinucleotide (NADH) from oxidized nicotinamide adenine dinucleotide (NAD$^+$) and reduced flavin adenine dinucleotide (FADH2) from oxidized flavin adenine dinucleotide (FAD), as well as oxidative phosphorylation, during which NADH and FADH2 is oxidized back to NAD$^+$ and FAD.

The electrons released by oxidation of NADH are shuttled down a series of protein complexes (Complex I, Complex II, Complex III, and Complex IV) known as the electron transport chain or the respiratory chain. The oxidation of succinate occurs at Complex II (succinate dehydrogenase complex) and FAD is a prosthetic group in the enzyme complex succinate dehydrogenase (complex II). The respiratory complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

The citric/tricarboxylic acid cycle and oxidative phosphorylation are preceded by glycolysis, in which a molecule of glucose is broken down into two molecules of pyruvate, with net generation of two molecules of ATP per molecule of glucose. The pyruvate molecules then enter the mitochondria, where they are completely oxidized to $CO_2$ and $H_2O$ via oxidative phosphorylation (the overall process is known as aerobic respiration). The complete oxidation of the two pyruvate molecules to carbon dioxide and water yields about at least 28-29 molecules of ATP, in addition to the 2 molecules of ATP generated by transforming glucose into two pyruvate molecules. If oxygen is not available, the pyruvate molecule does not enter the mitochondria, but rather is converted to lactate, in the process of anaerobic respiration.

The overall net yield per molecule of glucose is thus approximately at least 30-31 ATP molecules. ATP is used to power, directly or indirectly, almost every other biochemical reaction in the cell. Thus, the extra (approximately) at least 28 or 29 molecules of ATP contributed by oxidative phosphorylation during aerobic respiration are critical to the proper functioning of the cell. Lack of oxygen prevents aerobic respiration and will result in eventual death of almost all aerobic organisms; a few organisms, such as yeast, are able to survive using either aerobic or anaerobic respiration.

When cells in an organism are temporarily deprived of oxygen, anaerobic respiration is utilized until oxygen again becomes available or the cell dies. The pyruvate generated during glycolysis is converted to lactate during anaerobic respiration. The build-up of lactic acid is believed to be responsible for muscle fatigue during intense periods of activity, when oxygen cannot be supplied to the muscle cells. When oxygen again becomes available, the lactate is converted back into pyruvate for use in oxidative phosphorylation.

Mitochondrial dysfunction contributes to various disease states. Some mitochondrial diseases are due to mutations or deletions in the mitochondrial genome or nuclear. If a threshold proportion of mitochondria in the cell are defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved.

Use of the Compound of the Invention

The compound of the invention may be used in any situation where an enhanced or restored energy production (ATP) is desired. Examples are e.g. in all clinical conditions where there is a potential benefit of increased mitochondrial ATP-production or a restoration of mitochondrial function, such as in the restoration of drug- or chemically induced mitochondrial dysfunction or lactic acidosis conditions associated with reduced levels of succinate or functional activity of succinate, conditions where the anaplerotic effect of succinate or its signaling properties are useful, and the treatment of inborn errors of metabolism, cancer, diabetes, acute starvation, endotoxemia, sepsis, reduced hearing visual acuity, systemic inflammatory response syndrome and multiple organ dysfunction syndrome.

In particular, Compound 1 can be used in medicine, notably in the treatment or prevention of a mitochondria-related condition, disease or disorder, in nutricosmetics or in cosmetics.

Dysfunction of mitochondria is also described in relation to renal tubular acidosis; motor neuron diseases; other neurological diseases; epilepsy; genetic diseases; Huntington's Disease; mood disorders; schizophrenia; bipolar disorder; age-associated diseases; cerebral vascular accidents, macular degeneration; diabetes; menopausal symptoms and cancer.

Compound 1 for Use in Mitochondrial Related Disorders or Diseases

The compound according to the invention may be used in the prevention or treatment a mitochondria-related disease selected from the following:
Aging
Alpers Disease (Progressive Infantile Poliodystrophy),
Alzheimer's disease
Amyotrophic lateral sclerosis (ALS),
Autism,
Barth syndrome (Lethal Infantile Cardiomyopathy),
Beta-oxidation Defects, Bioenergetic metabolism deficiency,
Carnitine-Acyl-Carnitine Deficiency,
Carnitine Deficiency,
Creatine Deficiency Syndromes (Cerebral Creatine Deficiency Syndromes (CODS) includes: Guanidinoacetate Methyltransferase Deficiency (GAMT Deficiency), L-Arginine:Glycine Amidinotransferase Deficiency (AGAT Deficiency), and SLC6A8-Related Creatine Transporter Deficiency (SLC6A8 Deficiency),
Co-Enzyme Q10 Deficiency,
Complex I Deficiency (NADH dehydrogenase (NADH-CoQ reductase deficiency),
Complex II Deficiency (Succinate dehydrogenase deficiency),
Complex III Deficiency (Ubiquinone-cytochrome c oxidoreductase deficiency),
Complex IV Deficiency/COX Deficiency (Cytochrome c oxidase deficiency is caused by a defect in Complex IV of the respiratory chain),
Complex V Deficiency (ATP synthase deficiency),
COX Deficiency, CPEO (Chronic Progressive External Ophthalmoplegia Syndrome),
CPT I Deficiency,
CPT II Deficiency,
Diabetes type II,
Friedreich's ataxia (FRDA or FA),
Glutaric Aciduria Type II,
KSS (Kearns-Sayre Syndrome),
Lactic Acidosis,
LCAD (Long-Chain Acyl-CoA Dehydrogenase Deficiency),
LC-FAOD (Long-Chain Fatty Acid Oxidation Disorders)
LCHAD, Leigh Disease or Syndrome (Subacute Necrotizing Encephalomyelopathy),
LHON (Leber's hereditary optic neuropathy),
Luft Disease,
MCAD (Medium-Chain Acyl-CoA Dehydrogenase Deficiency),
MELAS (Mitochondrial Encephalomyopathy Lactic Acidosis and Strokelike Episodes),
MERRF (Myoclonic Epilepsy and Ragged-Red Fiber Disease),
METHYLMALONYL-CoA EPIMERASE DEFICIENCY,
METHYLMALONYL-CoA MUTASE DEFICIENCY,
MITOCHONDRIAL DNA DEPLETION SYNDROME 5,
MITOCHONDRIAL DNA DEPLETION SYNDROME 9,
MITOCHONDRIAL DNA DEPLETION SYNDROME 15 (HEPATOCEREBRAL TYPE) (1 family),
Maternally inherited diabetes and deafness,
MIRAS (Mitochondrial Recessive Ataxia Syndrome),
Mitochondrial Cytopathy,
Mitochondrial DNA Depletion,
Mitochondrial Encephalopathy including: Encephalomyopathy and Encephalomyelopathy, Mitochondrial Myopathy,
MNGIE (Myoneurogastointestinal Disorder and Encephalopathy,
NARP (Neuropathy, Ataxia, and Retinitis Pigmentosa),
Neurodegenerative disorders associated with Parkinson's, Alzheimer's or Huntington's disease,
Parkinson's disease
Pearson Syndrome, Progressive external ophtalmoplegia,
Propionic academia,
Pyruvate Dehydrogenase Deficiency,
POLG Mutations,
Respiratory Chain Deficiencies,
SCAD (Short-Chain Acyl-CoA Dehydrogenase Deficiency),
SCHAD and
VLCAD (Very Long-Chain Acyl-CoA Dehydrogenase Deficiency).

Of specific interest is the use of Compound 1 in the treatment of Leigh Syndrome, LHON, MELAS, MERRF (myoclonic epilepsy with ragged red fibers). and other diseases/conditions relating to Complex I defects.

Use of Compounds of the Invention in Cosmetics

The compounds according to the invention may be used in Cosmetics for the following:
Improved metabolic function in dermal cells (aging skin)
Astringent (acne)

Use of Compounds of the Invention as Nutritional Supplements

The compounds according to the invention may be used as nutritional supplements for the following:
Increased energy demand due to strenuous physical activity
Increased energy demand due to metabolic decompensation during infections and surgery
Enhanced muscle recovery via rapid distribution to tissue and by-passing glycolysis Pharmaceutical Compositions Comprising a Compound of the Invention The present invention also provides a pharmaceutical composition comprising the isolated Compound 1 compounds of the invention together with one or more pharmaceutically acceptable diluents or carriers.

The compound of the invention or a formulation thereof may be administered by any conventional method for example but without limitation it may be administered parenterally, orally, topically (including mucosal, buccal, sublingual. transdermal or to the skin), via a medical device (e.g. a stent), by inhalation or via injection or infusion (intraveneous, subcutaneous, intramuscular etc.). The treatment may consist of a single dose or a plurality of doses over a period of time.

The treatment may be by administration once daily, twice daily, three times daily, four times daily etc. The treatment may also be by continuous administration such as e.g. administration intravenous by drop.

Whilst it is possible for the compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Examples of suitable carriers are described in more detail below.

The formulations may conveniently be presented in dosage form such as a unit dosage form and may be prepared by any of the methods well known in the art of pharmacy. Such methods include the step of bringing into association the active ingredient (compound of the invention) with the carrier which constitutes one or more accessory ingredients. In general, the formulations are prepared by uniformly and intimately bringing into association the active ingredient with liquid carriers or finely divided solid carriers or both, and then, if necessary, shaping the product.

The compound of the invention will normally be administered intravenously, orally or by any parenteral route, in the form of a pharmaceutical formulation comprising the active ingredient, optionally in the form of a non-toxic organic, or inorganic, acid, or addition salt, in a pharmaceutically acceptable dosage form. Depending upon the disorder and patient to be treated, as well as the route of administration, the compositions may be administered at varying doses.

The pharmaceutical compositions must be stable under the conditions of manufacture and storage; thus, preferably it should be preserved against the contaminating action of microorganisms such as bacteria and fungi. Dependent on the formulation type and administration route chosen, the carrier can be a solvent or dispersion medium containing, for example, water, ethanol, polyol (e.g. glycerol, propylene glycol and liquid polyethylene glycol), vegetable oils, and suitable mixtures thereof.

For example, the compound of the invention may also be administered orally, buccally or sublingually in the form of tablets, capsules, ovules, elixirs, gels, solutions, emulsions, or suspensions, which may contain flavouring or colouring agents, for immediate-, delayed- or controlled-release applications.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Solutions or suspensions of the compound of the invention suitable for oral administration may also contain excipients e.g. solvents such as water, ethanol etc., N,N-dimethylacetamide, dispersants e.g. polysorbate 80, surfactants, and solubilisers, e.g. polyethylene glycol, Phosal 50 PG (which consists of phosphatidylcholine, soya-fatty acids, ethanol, mono/diglycerides, propylene glycol and ascorbyl palmitate). The formulations according to present invention may also be in the form of emulsions, wherein a Compound 1 compound may be present in a water-in-oil or oil-in-water emulsion. The oil may be any oil-like substance such as e.g. soy bean oil, safflower oil etc., triglycerides such as medium chain triglyceride (MCT-oil) such as e.g. coconut oil, palm oil etc or combinations thereof.

Tablets may contain pharmaceutically acceptable excipients such as fillers, binders, dispersing agents, disintegrants, glidants, pH-adjusting agents, stabilisers, taste-masking agents etc. Specific examples include microcrystalline cellulose, lactose (e.g. lactose monohydrate or lactose anyhydrous), sodium citrate, calcium carbonate, dibasic calcium phosphate and glycine, butylated hydroxytoluene (E321), crospovidone, hypromellose, disintegrants such as starch (preferably corn, potato or tapioca starch), sodium starch glycollate, croscarmellose sodium, and certain complex silicates, and granulation binders such as polyvinylpyrrolidone, hydroxypropylmethylcellulose (HPMC), hydroxy-propylcellulose (HPC), macrogol 8000, sucrose, gelatin and acacia. Additionally, lubricating agents such as magnesium stearate, stearic acid, glyceryl behenate and talc may be included.

A tablet may be made by compression or moulding, optionally with one or more pharmaceutically acceptable excipients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl-cellulose in varying proportions to provide desired release profile.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Formulations suitable for topical administration in the mouth include film compositions or lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Pharmaceutical compositions adapted for topical administration may be formulated as ointments, creams, suspensions, emulsions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms or infusions are prepared utilizing the active ingredient and a sterile vehicle, for example but without limitation water, alcohols, polyols, glycerine and vegetable oils, water being preferred. The active ingredient, depending on the vehicle and concentration used, can be either colloidal, suspended or dissolved in the vehicle. In preparing solutions the active ingredient can be dissolved in water for injection and sterilised, eg by filter sterilization, before filling into a suitable vial or ampoule and sealing.

Advantageously, agents such as local anaesthetics, preservatives and buffering agents can be dissolved in the vehicle. To enhance the stability, the composition can be frozen eg by freeze drying after filling into the vial and the water removed under vacuum. The dry lyophilized powder is then sealed in the vial and an accompanying vial of water for injection may be supplied to reconstitute the liquid prior to use.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability.

Pharmaceutical compositions of the present invention include formulations suitable for intraocular administration. These consist of a therapeutically effective quantity of Compound 1, one or more pharmaceutically acceptable excipients or a pharmaceutically acceptable carrier. Such pharmaceutical compositions may be the conventional dosage form of eye drops or other composition having better bioavailability. Such compositions overcoming the ocular drug delivery barriers and having improved ocular bioavailability are e.g. emulsions, ointments, suspensions, aqueous gels, nanomicelles, nanoparticles, liposomes, dendrimers, nanosuspensions, microneedles, and in situ thermosensitive gels.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

As seen from the Examples herein, excipients containing carbonate should be avoided, notably in liquid or semi-solid formulations. Preferably carbonate concentration should be below 0.85 mM.

It should be understood that in addition to the ingredients particularly mentioned above the formulations of this invention may include other agents conventional in the art having regard to the type of formulation in question, for example those suitable for oral administration may include flavouring agents. A person skilled in the art will know how to choose a suitable formulation and how to prepare it (see eg. Remington's Pharmaceutical Sciences 18 Ed. or later). A person skilled in the art will also know how to choose a suitable administration route and dosage.

The present invention provides a process for preparing a liquid pharmaceutical composition according to any of the preceding claims, said process comprising the steps of:
  a) obtaining methyl 3-[(2-acetylaminoethylthio)carbonyl] propionate (Compound 1) as the free form or a salt, hydrate, solvate or complex thereof,
  b) optionally heating to less than 90° C., such as 60° C. or keeping at room temperature
  c) adding an aqueous liquid (e.g. phosphate buffer saline at pH 7.4), saline solution or pure water d) optionally aiding dissolution with sonication
e) mixing at room temperature
to obtain said pharmaceutical composition.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

All % values mentioned herein are % w/w unless the context requires otherwise.

Nutricosmetic Compositions Comprising a Compound of the Invention

Nutricosmetics are orally administered products. The present invention also provides a nutricosmetic composition comprising the Compound 1 compounds. Nutricosmetic compositions comprise Compound 1 in the free form or a salt, hydrate, solvate or complex thereof together with one or more orally acceptable diluents or carriers. Nutricosmetic compositions are very alike pharmaceutical composition for oral administration.

Hence, typical compositions are tablets, capsules, ovules, elixirs, gels, solutions or suspensions.

Cosmeceutical Compositions Comprising a Compound of the Invention

Cosmeceutical compositions are typically administered to the skin or mucosa. Sometimes they may also be given by injections. The present invention also provides a cosmeceutical composition comprising the Compound 1 compounds. Cosmeceutical compositions comprise Compound 1 in the free form or a salt, hydrate, solvate or complex thereof together with one or more orally acceptable diluents or carriers.

Typical cosmeceutical compositions include those mentioned herein above suitable for application to the skin, to the mucosa or by injection.

Other Aspects of the Invention

The present invention also provides a combination (for example for the treatment of mitochondrial dysfunction) of a compound of formula (I) or a pharmaceutically acceptable form thereof as hereinbefore defined, and one or more agents independently selected from:
  Quinone derivatives, e.g. Ubiquinone, Idebenone, MitoQ
  Vitamins e.g. Tocopherols, Tocotrienols and Trolox (Vitamin E), Ascorbate (C), Thiamine (B1), Riboflavin (B2), Nicotinamide (B3), Menadione (K3),
  Antioxidants in addition to vitamins e.g. TPP-compounds (MitoQ), Sk-compounds, Epicatechin, Catechin, Lipoic acid, Uric acid, Melatonin
  Dichloroacetate
  Methylene blue
  L-arginine
  Szeto-Schiller peptides, elamipretide and elamipretide analogs
  Creatine
  Benzodiazepines
  Modulators of PGC-1α
  Modulators of AMPK
  Modulators of mitochondrial fission and fusion
  PPARalfa/beta/gamma-agonists
  Trolox analogs, carboxamide derivatives
  Nrf-2 activators
  $NAD^+$ modulators
  $NAD^+$ precursors
  Ketogenic diet One other aspect of the invention is that any of the Compound 1 compounds as disclosed herein may be administered together with any other compounds such as e.g. sodium bicarbonate (as a bolus (e.g. 1 mEq/kg) followed by a continuous infusion.) as a concomitant medication to the compounds as disclosed herein.

Lactic Acidosis or Drug-Induced Side-Effects Due to Complex I-Related Impairment of Mitochondrial Oxidative Phosphorylation The present invention also relates to the prevention or treatment of lactic acidosis and of mitochondrial-related drug-induced side effects. In particular the Compound 1 compounds according to the invention are used in the prevention or treatment of a mitochondrial-related drug or toxin-induced side effects at or up-stream of Complex I, or expressed otherwise, the invention provides according to the invention for the prevention or treatment of drug-induced direct inhibition of Complex I or of any drug-induced effect that limits the supply of NADH to Complex I (such as, but not limited to, effects on Krebs cycle, glycolysis, beta-oxidation, pyruvate metabolism and even drugs that effects the transport or levels of glucose or other complex I related substrates).

Mitochondrial toxicity induced by drugs may be a part of the desired therapeutic effect (e.g. mitochondrial toxicity induced by cancer drugs), but in most case mitochondrial toxicity induced by drugs is an unwanted effect. Mitochondrial toxicity can markedly increase glycolysis to compensate for cellular loss of mitochondrial ATP formation by oxidative phosphorylation. This can result in increased lactate plasma levels, which if excessive results in lactic acidosis, which can be lethal. Type A lactic acidosis is primarily associated with tissue hypoxia, whereas type B aerobic lactic acidosis is associated with drugs, toxin or systemic disorders such as liver diseases, diabetes, cancer and inborn errors of metabolism (e.g. mitochondrial genetic defects).

Many known drug substances negatively influence mitochondrial respiration (e.g. antipsychotics, local anaesthetics and anti-diabetics) and, accordingly, there is a need to identify or develop means that either can be used to circumvent or alleviate the negative mitochondrial effects induced by the use of such a drug substance. In addition, several chemical agents and gasses negatively influence mitochondrial metabolism and function.

The present invention provides Compound 1 compounds for use in the prevention or treatment of lactic acidosis and of mitochondrial-related drug or toxin-induced side effects. In particular the succinate prodrugs are used in the prevention or treatment of a mitochondrial-related drug-induced side effects at or up-stream of Complex I, or expressed otherwise, the invention provides succinate prodrugs for the prevention or treatment of drug-induced direct inhibition of Complex I, other respiratory complexes, or of any drug-induced effect that limits the supply of NADH to Complex I (such as, but not limited to, effects on Krebs cycle, glycolysis, beta-oxidation, pyruvate metabolism and even drugs that effects the transport or levels of glucose or other Complex I related substrates).

As mentioned above, increased lactate plasma levels are often observed in patients treated with drugs that may have mitochondrial-related side effects. The present invention is based on experimental results showing that metformin (first-line treatment for type 2 diabetes and which has been associated with lactic acidosis as a rare side-effect) inhibits mitochondrial function of human peripheral blood cells at Complex I in a time- and dose-dependent fashion at concentrations relevant for metformin intoxication. Metformin further causes a significant increase in lactate production by intact platelets over time.

Accordingly, the invention provides compounds according to Formula (I) for use in the prevention of treatment of lactic acidosis. However, as the results reported herein are based on lactic acidosis related to direct inhibition of Complex I or associated with a defect at or up-stream of Complex I, it is contemplated that the compounds according to the invention are suitable for use in the prevention or treatment of a mitochondrial-related drug-induced side-effects at or up-stream of Complex I. The compounds according to the invention would also counteract drug effects disrupting metabolism upstream of complex I (indirect inhibition of Complex I, which would encompass any drug effect that limits the supply of NADH to Complex I, e.g. effects on Krebs cycle, glycolysis, beta-oxidation, pyruvate metabolism and even drugs that affect the levels of glucose or other complex I related substrates). The compounds may also counteract defects down-stream of Complex I (complex III, IV and V), by increasing proton motive force.

It is contemplated that Compound 1 can be used in industrial applications, e.g. in vitro to reduce or inhibit formation of lactate or to increase the ATP-availability of commercial or industrial cell lines. Examples include the use in cell culture, in organ preservation, etc.

The compounds according to the invention are used in the treatment or prevention of drug-induced mitochondrial-related side-effects or to increase or restore cellular levels of energy (ATP) or of succinate, in the treatment. Especially, they are used in the treatment or prevention of direct or indirect drug-induced Complex I mitochondrial-related side-effects. In particular, they are used in the treatment or prevention of lactic acidosis, such as lactic acidosis induced by a drug substance.

The invention also relates to a combination of Compound 1 and a drug substance that may induce a mitochondrial-related side-effect, in particular a side-effect that is caused by direct or indirect impairment of Complex I by the drug substance. Such combination can be used as prophylactic prevention of a mitochondrial-related side-effect or, in case the side-effect appears, in alleviating and/or treating the mitochondrial-related side effect.

It is contemplated that Compound 1 will be effective in treatment or prevention of drug-induced side-effects, in particular in side-effects related to direct or indirect inhibition of Complex I.

Drug substances that are known to give rise in Complex I defects, malfunction or impairment and/or are known to have lactic acidosis as side-effect are:

Analgesics including acetaminophen, capsaicin
Antianginals including amiodarone, perhexiline
Antibiotics including linezolid, trovafloxacin, gentamycin
Anticancer drugs including quinones including mitomycin C, adriamycin
Anti-convulsant drugs including valproic acid
Anti-diabetics including metformin, phenformin, butyl-biguanide, troglitazone and rosiglitazone, pioglitazone
Anti-Hepatitis B including fialuridine
Antihistamines
Anti-Parkinson including tolcapone
Anti-psycotics Risperidone,
Anti-schizoprenia zotepine, clozapine
Antiseptics, quaternary ammonium compounds (QAC)
Anti-tuberculosis including isoniazid
Fibrates including clofibrate, ciprofibrate, simvastatin
Hypnotics including Propofol
Immunosupressive disease-modifying antirheumatic drug (DMARD) Leflunomide
Local anaesthetics including bupivacaine, diclofenac, indomethacin, and lidocaine
Muscle relaxant including dantrolene
Neuroleptics including antipsychotic neuroleptics like chlorpromazine, fluphenazine and haloperidol
NRTI (Nucleotide reverse Transcriptase Inhibitors) including efavirenz, tenofovir, emtricitabine, zidovudine, lamivudine, rilpivirine, abacavir, didanosine
NSAIDs including nimesulfide, mefenamic acid, sulindac
Barbituric acids.

Other drug substances that are known to have lactic acidosis as side-effects include beta2-agonists, epinephrine, theophylline or other herbicides. Alcohols and cocaine can also result in lactic acidosis.

Moreover, it is contemplated that the compounds of the invention also may be effective in the treatment or prevention of lactic acidosis even if it is not related to a Complex I defect.

Combination of Drugs and Compounds of the Invention

The present invention also relates to a combination of a drug substance and a compound of the invention for use in the treatment and/or prevention of a drug-induced side-effect selected from lactic acidosis and side-effect related to a Complex I defect, inhibition or malfunction, wherein
i) the drug substance is used for treatment of a disease for which the drug substance is indicated, and
ii) the compound of the invention is used for prevention or alleviation of the side effects induced or inducible by the drug substance, wherein the side-effects are selected from lactic acidosis and side-effects related to a Complex I defect, inhibition or malfunction.

Any combination of such a drug substance with any compound of the invention is within the scope of the present invention. Accordingly, based on the disclosure herein a person skilled in the art will understand that the gist of the invention is the findings of the valuable properties of compounds of the invention to avoid or reduce the side-effects described herein. Thus, the potential use of compounds of the invention capable of entering cells and deliver succinate and possibly other active moieties in combination with any drug substance that has or potentially have the side-effects described herein is evident from the present disclosure.

The invention further relates to
i) a composition comprising a drug substance and a compound of the invention, wherein the drug substance has a potential drug-induced side-effect selected from lactic acidosis and side-effects related to a Complex I defect, inhibition or malfunction,
ii) a composition as described above under i), wherein the compound of the invention is used for prevention or alleviation of side effects induced or inducible by the drug substance, wherein the side-effects are selected from lactic acidosis and side-effects related to a Complex I defect, inhibition or malfunction.

The composition may be in the form of two separate packages:

A first package containing the drug substance or a composition comprising the drug substance and a second package containing the Compound 1 compound of the invention or a composition comprising the compound of the invention. The composition may also be a single composition comprising both the drug substance and the Compound 1 compound of the invention.

In the event that the composition comprises two separate packages, the drug substance and the Compound 1 compound of the invention may be administered by different administration routes (e.g. drug substance via oral administration and compound of the invention by parenteral or mucosal administration) and/or they may be administered essentially at the same time or the drug substance may be administered before the compound of the invention or vice versa.

Kits

The invention also provides a kit comprising i) a first container comprising a drug substance, which has a potential drug-induced side-effect selected from lactic acidosis and side-effects related to a Complex I defect, inhibition or malfunction, and ii) a second container comprising a Compound 1 compound of the invention, which has the potential for prevention or alleviation of the side effects induced or inducible by the drug substance, wherein the side-effects are selected from lactic acidosis and side-effects related to a Complex I defect, inhibition or malfunction.

Method for Treatment/Prevention of Side-Effects

The invention also relates to a method for treating a subject suffering from a drug-induced side-effect selected from lactic acidosis and side-effect related to a Complex I defect, inhibition or malfunction, the method comprises administering an effective amount of a Compound 1 compound of the invention to the subject, and to a method for preventing or alleviating a drug-induced side-effect selected from lactic acidosis and side-effect related to a Complex I defect, inhibition or malfunction in a subject, who is suffering from a disease that is treated with a drug substance, which potentially induce a side-effect selected from lactic acidosis and side-effect related to a Complex I defect, inhibition or malfunction, the method comprises administering an effective amount of a Compound 1 compound of the invention to the subject before, during or after treatment with said drug substance.

Metformin

Metformin is an anti-diabetic drug belonging to the class of biguanides. It's the first line treatment for type 2 diabetes, which accounts for around 90% of diabetes cases in the U.S.A. The anti-diabetic effect has been attributed to decreasing hepatic glucose production, increasing the biological effect of insulin through increased glucose uptake in peripheral tissues and decreasing uptake of glucose in the intestine, but the exact mechanisms of action have not been completely elucidated. Despite its advantages over other anti-diabetics it has been related to rare cases of lactic acidosis (LA) as side effect). LA is defined as an increased anion gap, an arterial blood lactate level above 5 mM and a pH≤7.35.

The following list of non-limiting embodiments further illustrate the invention:

1. Isolated Methyl 3-[(2-acetylaminoethylthio)carbonyl] propionate (Compound 1) being the free form or a salt, hydrate, solvate or complex thereof.

2. The isolated Compound 1 according to embodiment 1, which is a solid product.

Figure 7A:
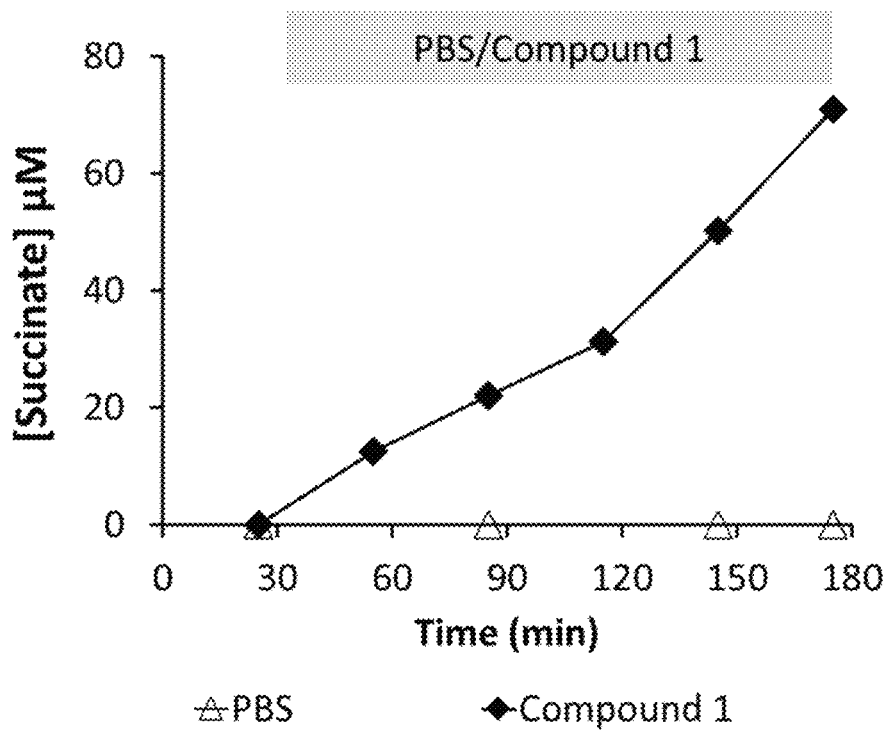
FIG. 7A-B. Intravenous infusion of PBS or Compound 1 in an anesthesised pig depicting succinate concentration in plasma versus time of infusion in (FIG. 7A), and fumarate concentrations in tissue in (FIG. 7B).
Figure 7B:
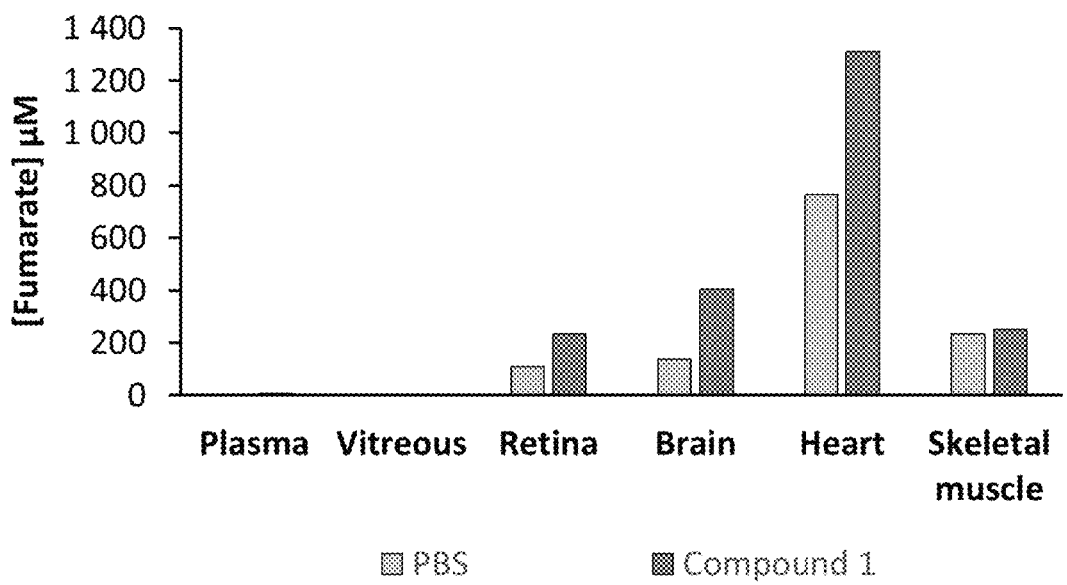

3. The isolated Compound 1 according to any of the preceding embodiments, which is or comprises a crystalline product such as the polymorph having the XRPD pattern of Compound 1 Batch 12 (FIG. 7) or having the XRPD pattern of Compound 1 Batch 15 (FIG. 8), or having the position (°2Theta) being 11.2 (±0.2) and 16.9 (±0.2).

4. The isolated Compound 1 according to any of embodiments 1-2, which is or comprises an amorphous product.

5. The isolated Compound 1 according to any of the preceding embodiments, having a purity of at least 20% w/w, at least 30% w/w, at least 40% w/w, at least 50% w/w, at least 60% w/w, at least 70% w/w, at least 75% w/w, at least 80% w/w, at least 90% w/w, at least 95% w/w, at least 97% w/w, at least 98% w/w or at least 99% w/w.

6. The isolated Compound 1 according to any of the preceding embodiments, having a content of related impurities of less than 75% w/w, less than 70% w/w, less than 65% w/w, less than 60% w/w, less than 55% w/w, less than 50% w/w, less than 45% w/w, less than 40% w/w, less than 35% w/w, less than 30% w/w, less than 25% w/w, less than 20% w/w, less than 15% w/w, less than 10% w/w, less than 5% w/w, less than 3% w/w, less than 2% w/w, or less than 1% w/w.

7. The isolated Compound 1 according to any of the preceding embodiments, having a content of synthesis precursors of less than 50% w/w, less than 40% w/w, less than 30% w/w, less than 25% w/w, less than 20% w/w, less than 15% w/w, less than 10% w/w, less than 5% w/w, less than 3% w/w, less than 2% w/w, or less than 1% w/w.

8. The isolated Compound 1 according to any of the preceding embodiments having a purity sufficient for pharmaceutical use.

9. The isolated Compound 1 according to any of the preceding embodiments, which is the free form.

10. The isolated Compound 1 according to any of embodiments 1-8, which is a salt.

11. The isolated Compound 1 according to embodiment 10, which is a hydrochloride salt, hydrobromide salt, acetate salt, citrate salt, lactate salt, maleate salt, or malonate salt.

12. The isolated Compound 1 according to any of embodiments 1-8, which is a hydrate such as a monohydrate.

13. The isolated Compound 1 according to any of the preceding embodiments, for use in humans or animals.

14. The isolated Compound 1 according to any of the preceding embodiments, for use in humans.

15. The isolated Compound 1 according to any of the preceding embodiments, for use in medicine.

16. The isolated Compound 1 according to any of the preceding embodiments, for use as the active pharmaceutical ingredient in a pharmaceutical product.

17. The isolated Compound 1 according to any of the preceding embodiments, for use in the treatment or prevention of a metabolic disease, a disease of mitochondrial dysfunction, a disease related to mitochondrial dysfunction, a mitochondrial disorder, mitochondrial energy deficiency, drug-induced mitochondrial side effects, cancer, diabetes, traumatic brain injury, cardiac arrest hypoxia, ischemia, stroke, myocardial infarction, acute angina, acute liver injury, coronary occlusion, atrial fibrillation, male infertility and menopausal symptoms in women.

18. The isolated Compound 1 according to embodiment 17, wherein said disease of mitochondrial dysfunction or disease related to mitochondrial dysfunction is selected from Aging
Alpers Disease (Progressive Infantile Poliodystrophy),
Alzheimer's disease,
Amyotrophic lateral sclerosis (ALS)Autism,
Barth syndrome (Lethal Infantile Cardiomyopathy),
Beta-oxidation Defects, Bioenergetic metabolism deficiency,
Carnitine-Acyl-Carnitine Deficiency,
Carnitine Deficiency,
Creatine Deficiency Syndromes (Cerebral Creatine Deficiency Syndromes (CCDS) including: Guanidinoacetate Methyltransferase Deficiency (GAMT Deficiency), L-Arginine: Glycine Amidinotransferase Deficiency (AGAT Deficiency), and SLC6A8-Related Creatine Transporter Deficiency (SLC6A8 Deficiency),
Co-Enzyme Q10 Deficiency,
Complex I Deficiency (NADH dehydrogenase (NADH-CoQ reductase deficiency),
Complex II Deficiency (Succinate dehydrogenase deficiency),
Complex III Deficiency (Ubiquinone-cytochrome c oxidoreductase deficiency),
Complex IV Deficiency/COX Deficiency (Cytochrome c oxidase deficiency is caused by a defect in Complex IV of the respiratory chain),
Complex V Deficiency (ATP synthase deficiency),
COX Deficiency, CPEO (Chronic Progressive External Ophthalmoplegia Syndrome), CPT I Deficiency,
CPT II Deficiency,
Diabetes type II,
Friedreich's ataxia (FRDA or FA),
Glutaric Aciduria Type II,
KSS (Kearns-Sayre Syndrome),
Lactic Acidosis,
LOAD (Long-Chain Acyl-CoA Dehydrogenase Deficiency),
LC-FAOD (Long-Chain Fatty Acid Oxidation Disease)
LCHAD, Leigh Disease or Syndrome (Subacute Necrotizing Encephalomyelopathy),
LHON (Leber's hereditary optic neuropathy),
Luft Disease,
MCAD (Medium-Chain Acyl-CoA Dehydrogenase Deficiency),
MELAS (Mitochondrial Encephalomyopathy Lactic Acidosis and Strokelike Episodes),
MERRF (Myoclonic Epilepsy and Ragged-Red Fiber Disease),
METHYLMALONYL-CoA EPIMERASE DEFICIENCY,
METHYLMALONYL-CoA MUTASE DEFICIENCY,
MITOCHONDRIAL DNA DEPLETION SYNDROME 5,
MITOCHONDRIAL DNA DEPLETION SYNDROME 9,
MITOCHONDRIAL DNA DEPLETION SYNDROME 15 (HEPATOCEREBRAL TYPE) (1 family),
Maternally inherited diabetes and deafness,
MI RAS (Mitochondrial Recessive Ataxia Syndrome),
Mitochondrial Cytopathy,
Mitochondrial DNA Depletion,
Mitochondrial Encephalopathy including: Encephalomyopathy and Encephalomyelopathy,
Mitochondrial Myopathy,
MNGIE (Myoneurogastointestinal Disorder and Encephalopathy,
NARP (Neuropathy, Ataxia, and Retinitis Pigmentosa),
Neurodegenerative disorders associated with Parkinson's, Alzheimer's or Huntington's disease,
Pearson Syndrome,
Parkinson's disease
Progressive external ophtalmoplegia,
Propionic academia,
Pyruvate Dehydrogenase Deficiency,
POLG Mutations,
Respiratory Chain Deficiencies,
SCAD (Short-Chain Acyl-CoA Dehydrogenase Deficiency),
SCHAD,
VLCAD (Very Long-Chain Acyl-CoA Dehydrogenase Deficiency).

19. The isolated Compound 1 according to embodiment 18, wherein said disease of mitochondrial dysfunction or disease related to mitochondrial dysfunction is attributed to complex I dysfunction and selected from Leigh Syndrome, Leber's hereditary optic neuropathy (LHON), MELAS (mitochondrial encephalomyopathy, lactic acidosis, and stroke-like episodes) and MERRF (myoclonic epilepsy with ragged red fibers).

20. The isolated Compound 1 according to any of embodiments 1-17, for use in the treatment or prevention of metabolic dysfunction.

21. The isolated Compound 1 according to embodiment 20, wherein said metabolic dysfunction is diabetes such as defective insulin secretion (Type 2 diabetes).

22. The isolated Compound 1 according to embodiment 20, wherein said metabolic dysfunction is drug induced side effects on mitochondria.

23. The isolated Compound 1 according to embodiment 22, wherein said drug induced side effects on mitochondria are selected from metformin induced complex I inhibition (lactic acidosis), paracetamol/acetaminophen induced complex I inhibition (liver failure) or drug-induced mitochondrial depletion.

24. The isolated Compound 1 according to embodiment 20, wherein said metabolic dysfunction is chemically induced side effects on mitochondria.

25. The isolated Compound 1 according to embodiment 24, wherein said chemically induced side effects on mitochondria are selected from rotenone inhibition of complex I (Parkinson like symptoms), pesticide-induced inhibition of respiratory complexes and mitochondrial enzymes, chemical warfare agent-induced inhibition of respiratory complexes and mitochondrial enzymes and gaseous poisoning of respiratory complexes and mitochondrial enzymes, e.g. carbon monoxide poisoning.

26. The isolated Compound 1 according to embodiment 20, wherein said metabolic dysfunction is genetical mitochondrial dysfunction.

27. The isolated Compound 1 according to embodiment 26, wherein said genetical mitochondrial dysfunction is selected from dysfunctional energy production due to decreased number of mitochondria, dysfunctional mitochondrial transcription factors, dysfunctional transcription factors for nuclear DNA encoded mitochondrial proteins, mitochondrial membrane proteins that contribute to the stabilization of large mitochondrial DNA (mtDNA)-protein complexes called nucleoids, dysfunctional energy production, pyruvate dehydrogenase deficiencies, deficiency of complex I, II, III or IV, or an enzyme deficiency like e.g. pyruvate dehydrogenase deficiency, dysfunction of enzymes involved in succinate synthesis, e.g. propionyl CoA carboxylase, methylmalonyl CoA mutase and succinyl CoA synthetase.

28. The isolated Compound 1 according to embodiment 27, where said effective amount is in the range from from 1 mg to 5.0 g per day, from 10 mg to 2.0 g per day, from 25 mg to 1 g per day, from 50 mg to 500 mg per day, from 100 mg to 1000 mg per day, from 250 mg to 1000 mg per day, or from 50 mg to 500 mg per day of Compound 1 or a salt, hydrate, solvate or complex thereof.

29. The isolated Compound 1 according to any of embodiments 15-28, wherein said Compound 1 or a salt, hydrate, solvate or complex thereof is administered to said subject from one time per day to 10 times per day, or from one time per day to 4 times per day.

30. The isolated Compound 1 according to any of embodiments 15-29, wherein said treatment or prevention is pre-treatment, e.g. the use before surgery, the use before planned medical intervention with a high metabolic demand, and before subject entering a war zone or other hazardous environment.

31. The isolated Compound 1 according to any of embodiments 15-30, wherein said treatment or prevention is a chronic treatment.

32. The isolated Compound 1 according to any of embodiments 1-14, for non-pharmaceutical use in humans or animals.

33. The isolated Compound 1 according to embodiment 19, for use as a cosmeceutical or nutricosmetics.

34. The isolated Compound 1 according to any of embodiments 28-29, for use as an energy drink or a cream.

35. Composition comprising the isolated Compound 1 according to any of the preceding embodiments.

36. Cosmeceutical comprising the isolated Compound 1 according to any of embodiments 1-14.

37. Nutricosmetics comprising the isolated Compound 1 according to any of embodiments 1-14.

38. Energy drink comprising the isolated Compound 1 according to any of embodiments 1-14.

39. Pharmaceutical composition comprising isolated Compound 1 according to any of embodiments 1-33.

40. A process for preparing isolated Compound 1 according to any of embodiments 1-33, said process comprising the steps of:
a) reacting N-acetyl cysteamine and monomethyl succinate, in the presence of a coupling reagent, in organic solvent, between 0° C. and 100° C.
b) isolating Compound 1,
so as to provide isolated Compound 1.

41. The process according to embodiment 40, wherein step a) is conducted where independently the solvent is dichloromethane, the coupling agent is carbonyldiimidazole and the temperature is 15-30° C.

42. The process according to any of embodiments 40-41 wherein step b) comprises extraction with an aqueous acidic solution (optionally 20% ammonium chloride) and then extracting the organic layer with another aqueous medium (suitable brine or water).

43. The process according to embodiment 42 wherein the organic layer is removed in vacuo and the residue dissolved in an organic solvent with suitable dissolution properties for crystallization, such as methyl-tert-butylether (MTBE).

44. The process according to embodiment 42 wherein the solution is cooled, suitably to approximately 5° C. and an antisolvent is added, such as n-heptane, after stirring for a period of time, suitably approximately 24 hours, compound 1 is harvested by filtration and washed with an antisolvent.

45. The isolated Compound 1 according to any of embodiments 1-3 where the position (°2Theta) is 11.2 (±0.2) and 16.9 (±0.2).

46. A pharmaceutical composition according to embodiment 39, which is a solid formulation.

47. The pharmaceutical composition according to embodiment 46, which is a solid formulation for reconstitution prior to use.

48. The pharmaceutical composition according to embodiment 46, which is an aqueous formulation.

49. The pharmaceutical composition according to embodiment 48, which is an aqueous Phosphate Buffered Saline (PBS) formulation.

50. The pharmaceutical composition according to any of embodiments 46-49, which has a concentration of Compound 1 of at least 10% w/w, at least 30% w/w, at least 50% w/w, at least 60% or at least 70% w/w.

51. The pharmaceutical composition according to any of embodiments 46-50, which is for oral administration, for subcutaneous administration, for intravenous administration, for parenteral administration, for ocular administration or for topical administration.

52. The pharmaceutical composition according to embodiment 51, which is a drink or a gel.

53. The pharmaceutical composition according to any of embodiments 46-52, which comprises from 1 mg to 5.0 g, from 10 mg to 2.0 g, from 25 mg to 1 g, from 50 mg to 500 mg, from 100 mg to 1000 mg, from 250 mg to 1000 mg, or from 50 mg to 500 mg of Compound 1 or a salt, hydrate, solvate or complex thereof.

54. The pharmaceutical composition according to any of embodiments 46-53, which is an immediate release formulation.

EXAMPLES

General Methods, Materials and Assays

HPLC Method for Purity Analysis

HPLC Method 1
Solvent A is Water+0.1% NH$_4$OH
Solvent B is 2.5 L Acetonitrile+130 ml H$_2$O+0.1% NH$_4$OH
Gradient: T=0 minutes, B %=5, flow rate=1 ml/min; T=0.1 minutes, B %=5, flow rate=1 ml/min; T=9.5 minutes, B %=95, flow rate=1 ml/min; T=10.2 minutes, B %=95, flow rate=1 ml/min; T=10.3 minutes, B %=95, flow rate=1.5 ml/min; T=11.1 minutes, B %=95, flow rate=1.5 ml/min; T=11.15 minutes, B %=5, flow rate=1.5 ml/min; T=11.5 minutes, B %=5, flow rate=1.5 ml/min;
Column is a Waters XSelect CSH C18 3.5 um, 2.1 mm×50 mm.
Absorbance is monitored at 234 nm on a diode array detector.
1 mg/ml sample conc, 1 µl injection volume
HPLC Method 2
Solvent A is Water+1.57 g NH$_4$HCO$_2$+5 ml Formic acid
Solvent B is 2.5 L Acetonitrile+130 ml H$_2$O+4.5 ml Formic acid Gradient: T=0 minutes, B %=0, flow rate=1 ml/min; T=1 minutes, B %=0, flow rate=1 ml/min; T=9.5 minutes, B %=20, flow rate=1 ml/min; T=10.3 minutes, B %=95, flow rate=1 ml/min; T=10.5 minutes, B %=95, flow rate=1.5 ml/min; T=11.0 minutes, B %=95, flow rate=1.5 ml/min; T=11.05 minutes, 13%=0, flow rate=1.5 ml/min; T=11.5 minutes, B %=0, flow rate=1.5 ml/min;

Column is a Waters XSelect CSH C18 3.5 um, 2.1 mm×50 mm.

Absorbance is monitored at 230 nm on a diode array detector.

1 mg/ml sample conc, 1 μl injection volume

Example 1

Synthesis of Methyl 3-[(2-acetylaminoethylthio)carbonyl]propionate (Compound 1)

Detailed description of the synthesis and isolation of Compound 1:

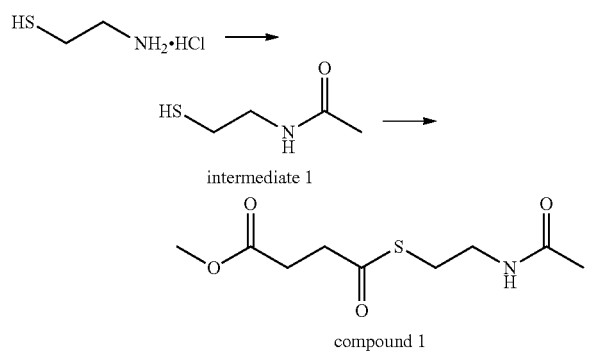

Compound 1 has been made by three separate methods (A, B and C below).

Method A

To a solution of 2-aminoethanethiol hydrochloride (226 g, 2 mol), KOH (114 g, 2 mol) and NaHCO$_3$ (168 g, 2 mol) in water (4 L) was added acetic anhydride (204 g, 2 mol) dropwise. The mixture was stirred at room temperature for 45 minutes. The reaction mixture was extracted with EtOAc (8×2 L), dried over MgSO$_4$ and the solvent was removed to give intermediate 1 (190 g, 80% yield) as slight yellow oil under reduced pressure.

To a solution of 4-methoxy-4-oxobutanoic acid (209 g, 1.583 mol) and HOBT (214 g, 1.583 mol) in dichloromethane (4 L) was added N-(3-Dimethylaminopropyl)-N'-ethylcar-bodiimide hydrochloride (304 g, 1.583 mol). The mixture was stirred at room temperature for 2 hours. Intermediate 1 (189 g, 1.583 mol) was added dropwise. The mixture was stirred at room temperature for 2 hours. triethylamine (160 g, 1.583 mol) was added dropwise. The mixture was stirred at room temperature overnight. The resulting mixture was washed with water (2 L) and saturated solution of NaHCO$_3$ (2×2 L), dried over Na$_2$SO$_4$ and concentrated under reduced pressure to afford crude compound 1 (350 g) as yellow oil. The crude compound 1 was purified by silica gel column chromatography (2000 g silica gel, eluting with CH$_2$Cl$_2$/MeOH=100/1 to 80/1) to give compound 1 (201 g, 94.9% in LCMS) as white solid. Crude side cuts from the purification (110 g) were purified by silica gel column chromatography (1200 g silica gel, eluting with CH$_2$Cl$_2$/MeOH=100/1 to 80/1) to give compound 1 (40 g, 96.7% in LCMS) as white solid.

Method B

Acetic anhydride was added dropwise (7.14 g, 0.07 mol) to a solution of 2-aminoethanethiol hydrochloride (11.3 g, 0.1 mol), KOH (5.6 g, 0.1 mol) and NaHCO$_3$ (5.88 g, 0.07 mol) in water (200 mL) at room temperature. The mixture was stirred at room temperature for 45 minutes. The reaction mixture was extracted with EtOAc (8×200 mL), dried over MgSO$_4$ (1 h) and then the solvent was removed in vacuo at 50° C. to give crude intermediate 1 (7 g, 84% yield) as slight yellow liquid.

1,1'-Carbonyldiimidazole (11.34 g, 0.07 mol) was added portion wise to a solution of 4-methoxy-4-oxobutanoic acid (9.24 g, 0.07 mol) in dichloromethane (200 mL). The mixture was stirred at room temperature for 1 hour. intermediate 1 (7 g, 0.059 mol) was added dropwise and then the mixture was stirred at room temperature for 3 hours. The resulting mixture was washed with HCl (1N, 3×150 mL) and saturated solution of NaHCO$_3$ (3×150 mL), dried over Na$_2$SO$_4$ (1 h) and then the solvent was removed in vacuo at 50° C. to afford 9.5 g of compound 1 as yellow solid.

Method C

To the solution of KOH (0.71 kg, 13.2 mol) and Na$_2$CO$_3$ (1.00 kg, 9.43 mol) in water (15 L) 2-aminoethanethiol hydrochloride (1.5 kg, 13.2 mol) was added. To the resulting clear dark violet solution acetic anhydride (0.96 kg, 9.43 mol) was added dropwise at +22° C. keeping the internal temperature below +30° C. during addition (addition time was 24 minutes). The reaction mixture was stirred at +20° C. for 1 h 35 min. Dichloromethane (23 L) was added and the mixture was stirred at +28±2° C. for 20 minutes. The layers were separated. Aqueous phase was extracted with dichloromethane (2×15 L) adjusting the internal temperature to +28±2° C. during extractions. The organic phases were combined, and solvent was removed in vacuo. Afterwards intermediate 1 was dried under vacuum at +40° C. for 18 hours. Yield 996 g and purity>97 area-% (GC). Crude intermediate 1 was obtained as brown oil.

Distillation: 933 g of intermediate 1 was distilled using thin layer distillation unit under the following conditions: T=+110° C., P=1 mbar, rate 202 g/h. Intermediate 1 was obtained as clear colourless oil.

To the solution of 4-methoxy-4-oxobutanoic acid (1.33 kg, 10.07 mol) in DCM (10 L) 1,1'-carbonyldiimidazole (CDI) (1.63 kg, 10.07 mol) was added portionwise. Intensive foaming and gas evolution were observed during addition. After the addition was finished the mixture was stirred at +20 to +25° C. for 1 hour. Intermediate 1 (1.00 kg, 8.39 mol) solution in dichloromethane (5 L) was added keeping the internal temperature below +30° C. The reaction mixture was stirred at +20 to +25° C. for 2 hours. 20% NH$_4$Cl aqueous solution (10 L) was added and the mixture was stirred for 20 minutes. The layers were separated. Organic phase was extracted with 13% NaCl aqueous solution and water, subsequently (10 L and 5 L, individually). Afterwards the solvent (DCM) was changed to MTBE by distillation. Solution of compound 1 in MTBE (approximately 6 L) was gradually cooled to +5° C. Crystallization started when the internal temperature reached +12° C. To the slurry n-heptane (15 L) was added and the mixture was stirred at 0 to +5° C. for 20 hours (overnight). Slurry was filtered and the filter cake was washed with N-heptane(2×3 L). Product was dried by pulling air through it for 42 hours. Yield was 1.26 kg (64%) and purity 98.5 area-% (HPLC).

Several batches of Compound 1 were prepared by the above described synthesis. The batches were purified by different purification methods, as set out in Methods A, B and C.

Batch 3 (or compound 1-s3) was prepared via Method A.
Batch 12 (or compound 1-s12), 13 (or compound 1-s13) and 14 (or compound 1-s14) were prepared by method B.

Batch 15 (or compound 1-s15), 16, and 17 were prepared by method C.

Example 2

Characterization of Compound 1 from Different Batches

Figure 11:
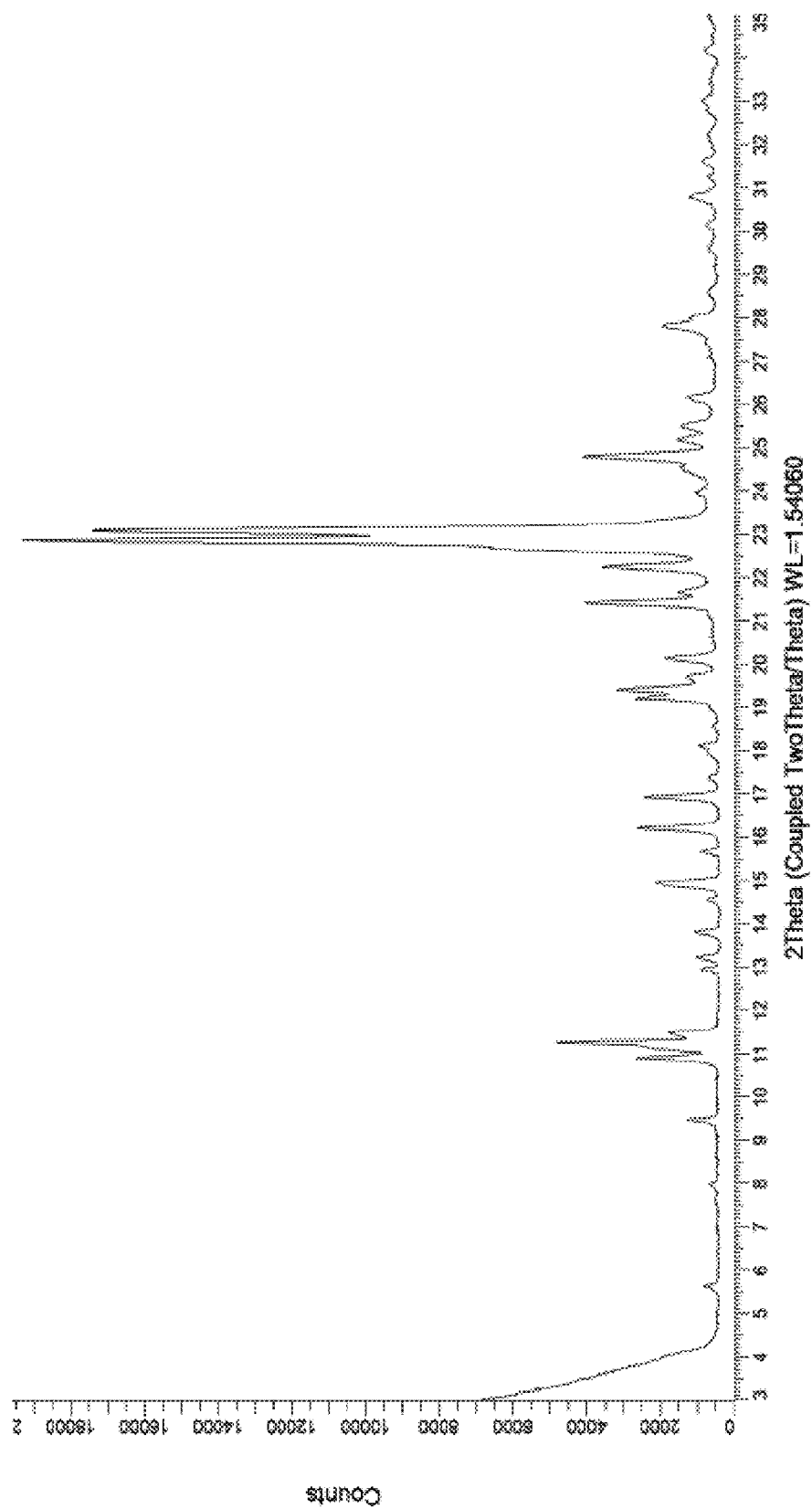
FIG. 11. XRPD analysis of Compound 1 Batch 12
Figure 12:
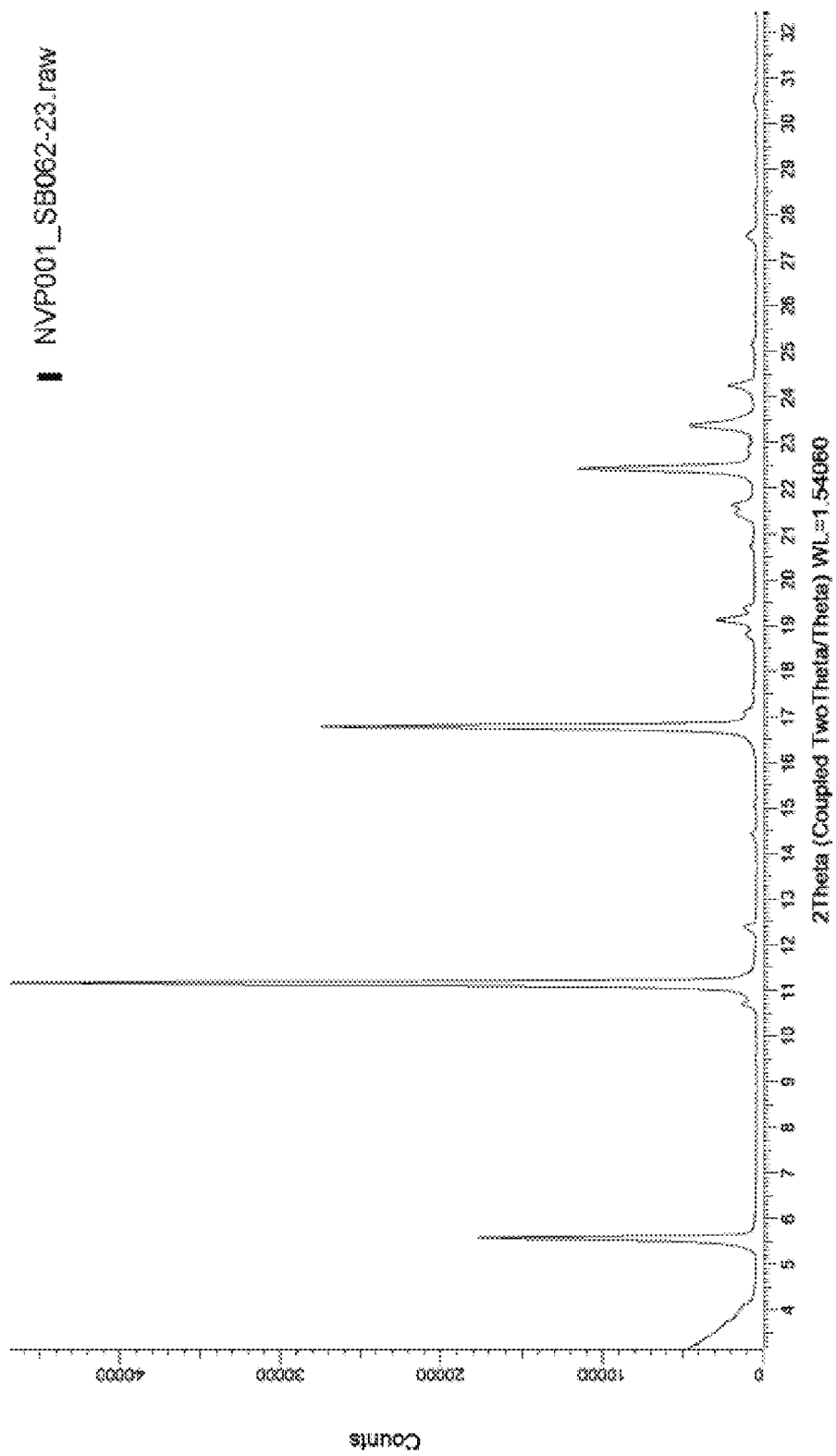
FIG. 12. XRPD analysis of Compound 1 Batch 15
Figure 13:
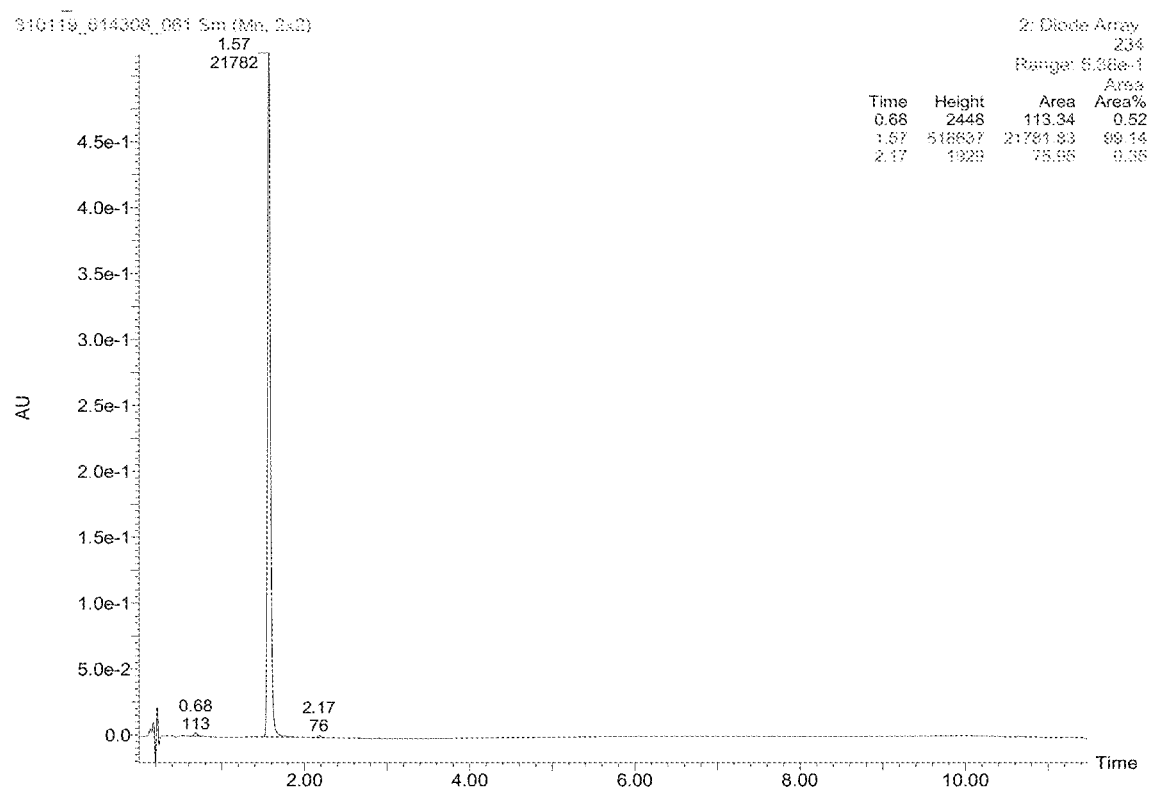
FIG. 13. LCMS analysis of Compound 1 Batch 3 depicting Absorbance Unit (AU) versus time using HPLC Method 1.
Figure 14:
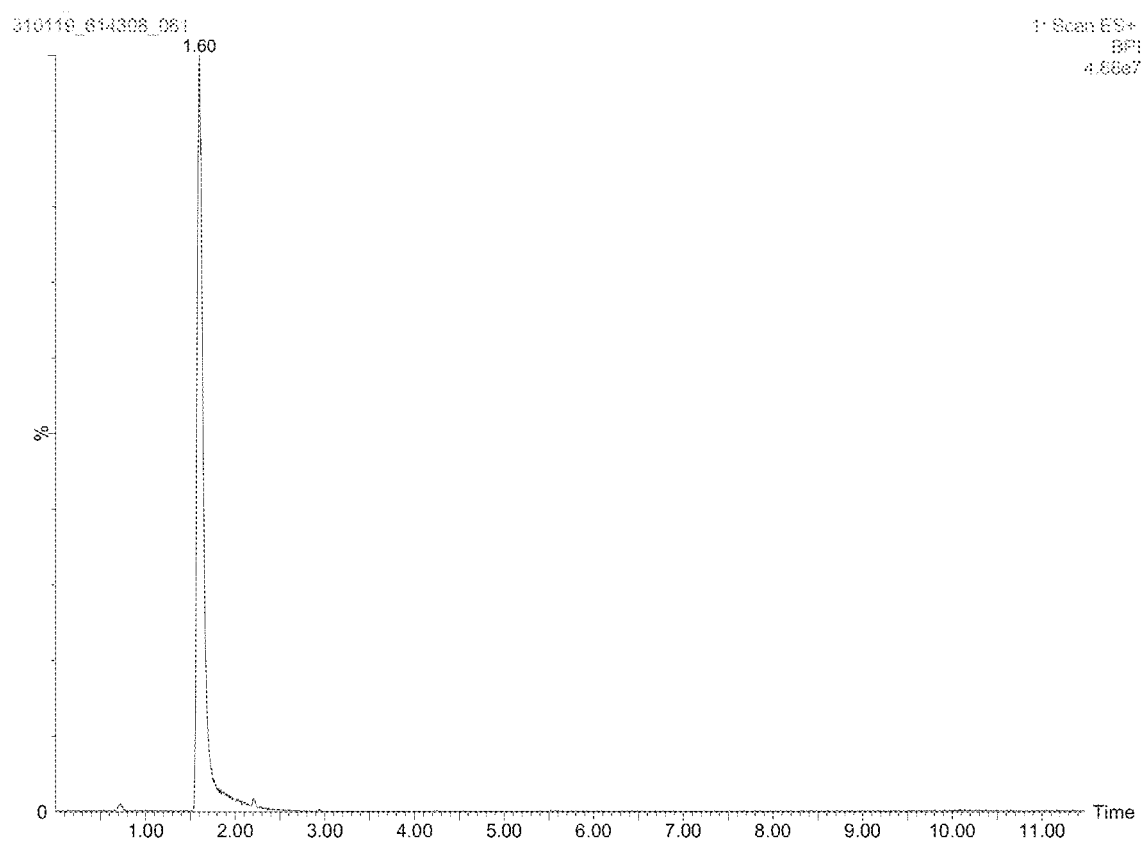
FIG. 14. LCMS analysis of Compound 1 Batch 3 depicting total ion count on a normalised scale versus time using HPLC Method 1.
Figure 15:
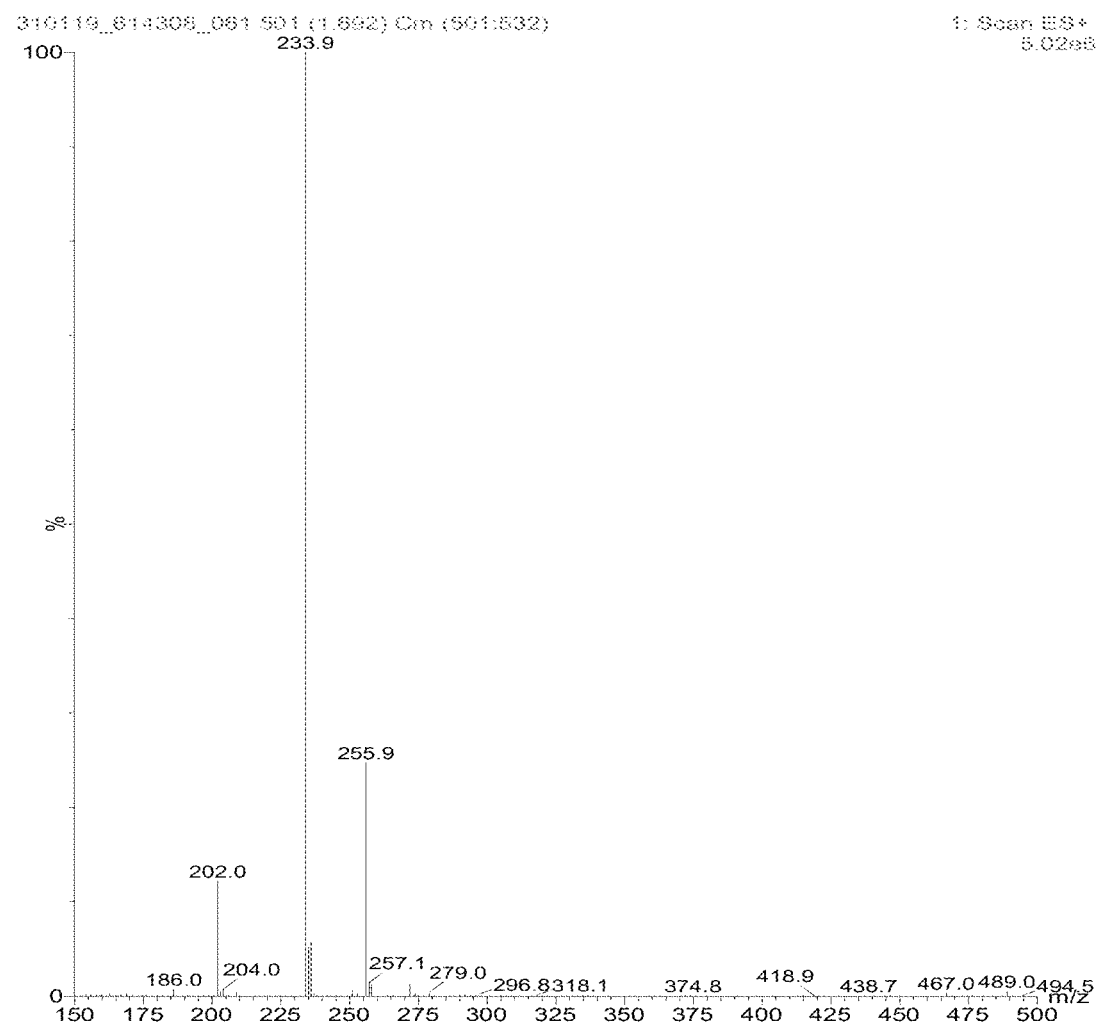
FIG. 15. LCMS analysis of Compound 1 Batch 3 depicting intensity (%) versus m/z using HPLC Method 1.
Figure 16:
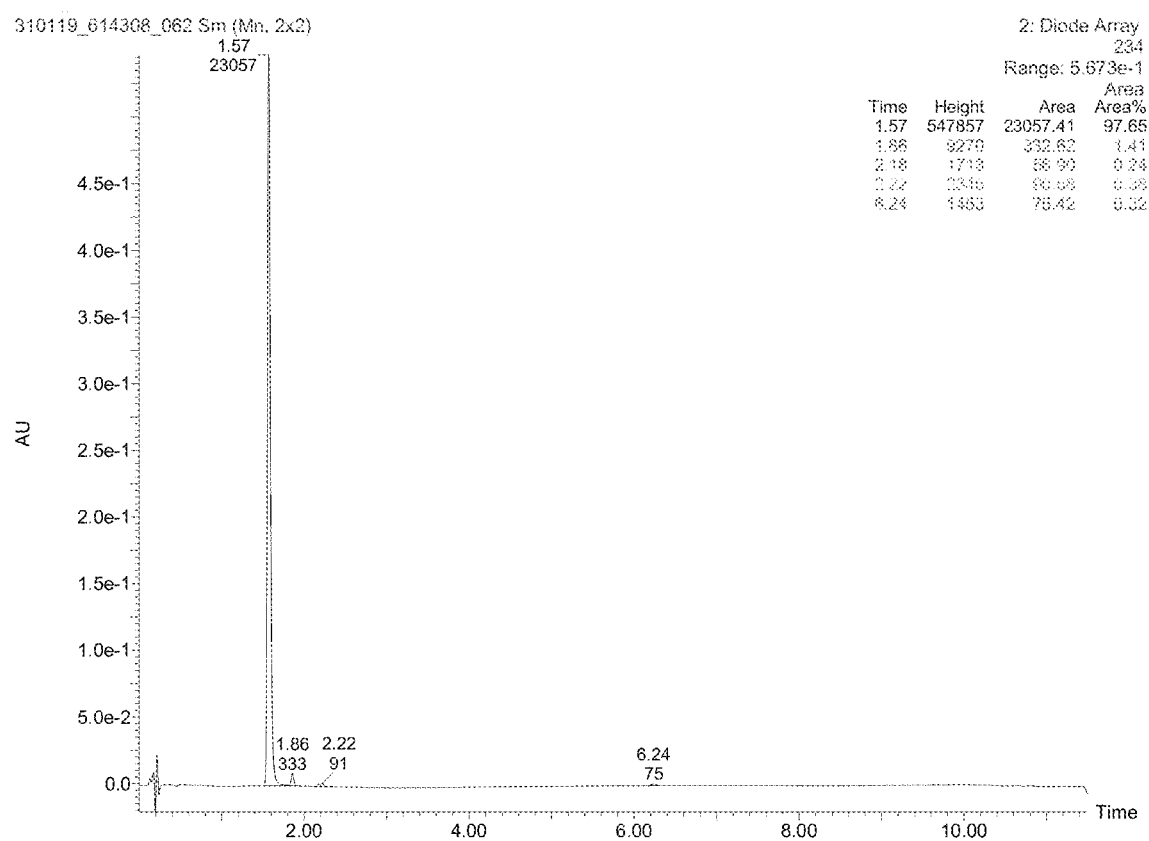
FIG. 16. LCMS analysis of Compound 1 Batch 12 depicting Absorbance Units (AU) versus time using HPLC Method 1.
Figure 17:
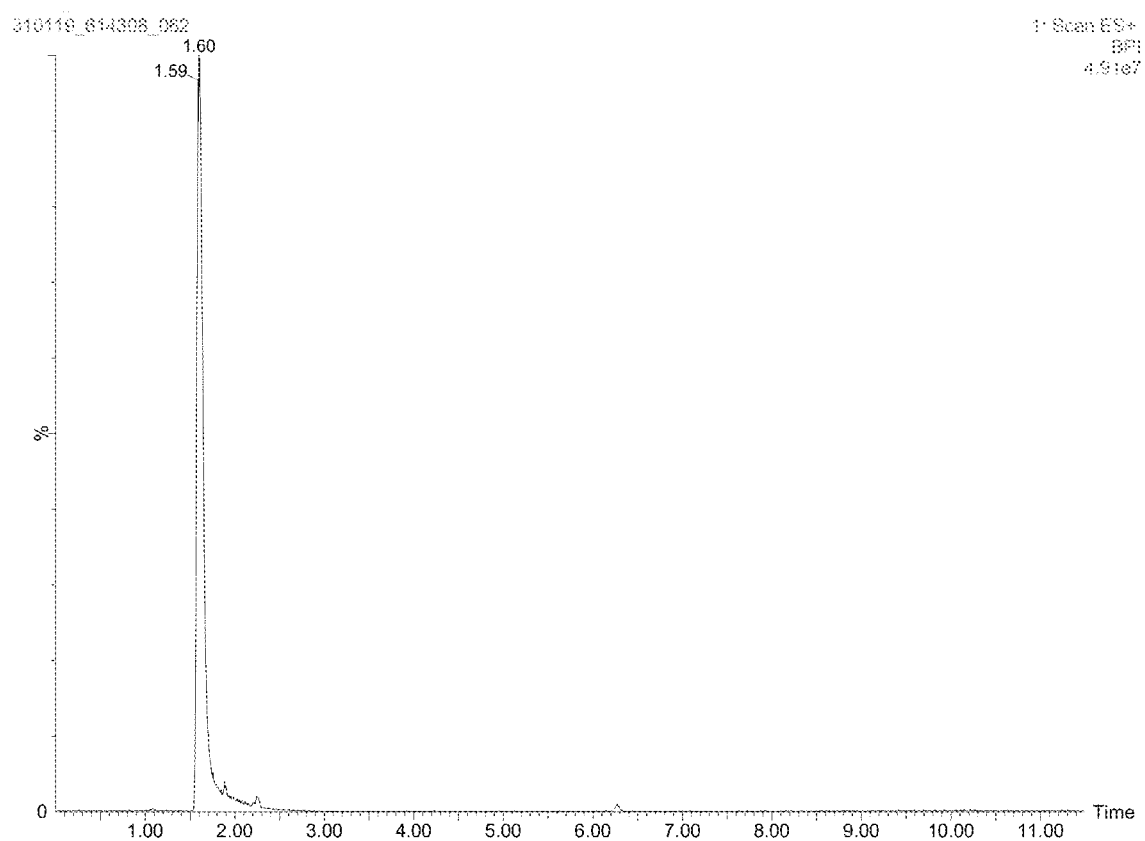
FIG. 17. LCMS analysis of Compound 1 Batch 12 depicting total ion count on a normalised scale versus time using HPLC Method 1.
Figure 18:
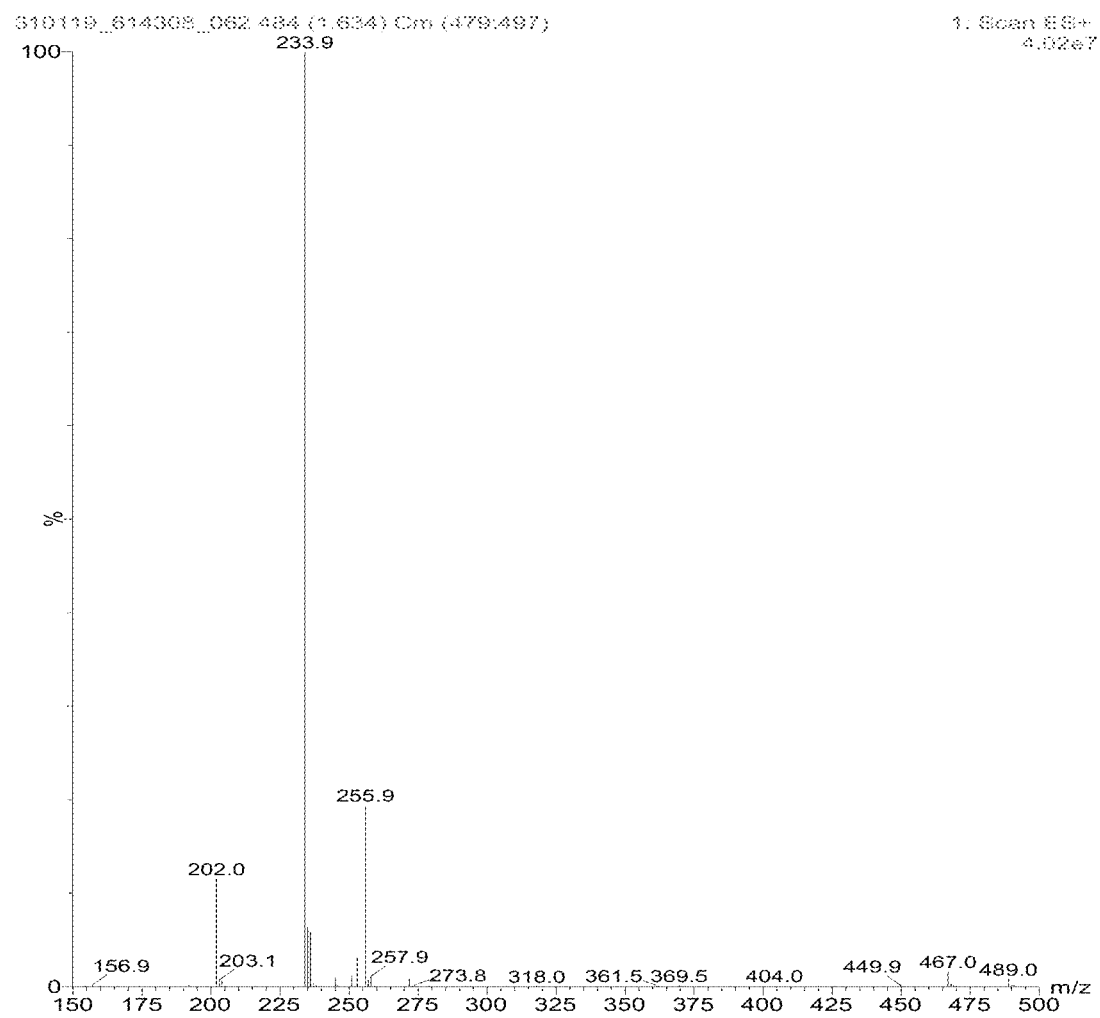
FIG. 18. LCMS analysis of Compound 1 Batch 12 depicting intensity (%) versus m/z using HPLC Method 1.
Figure 19:
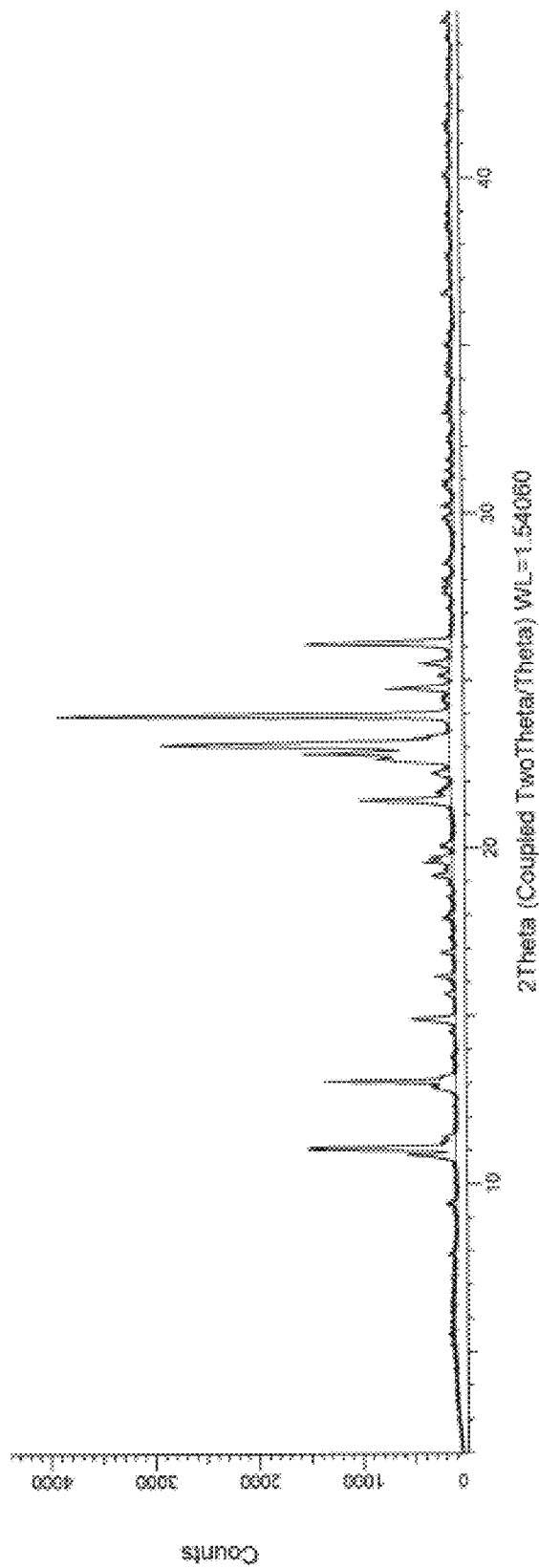
FIG. 19. XRPD analysis of Compound 1 Batch 3.
Figure 20:
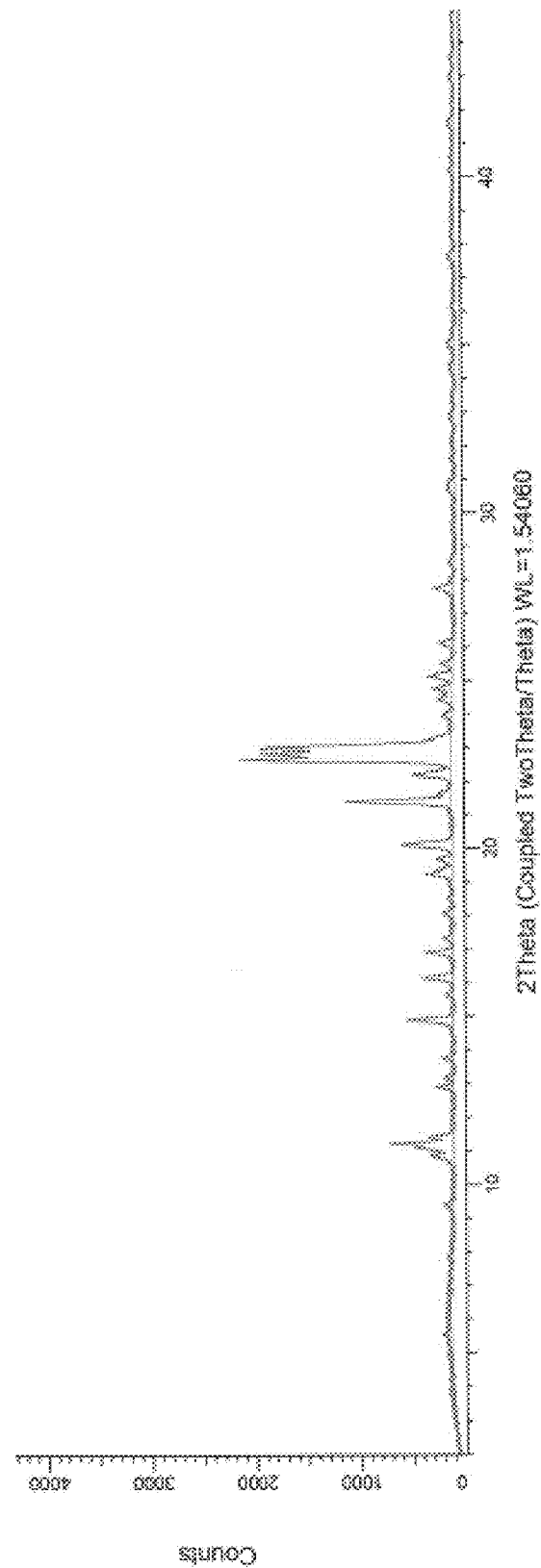
FIG. 20. XRPD analysis of Compound 1 Batch 18.
Figure 21:
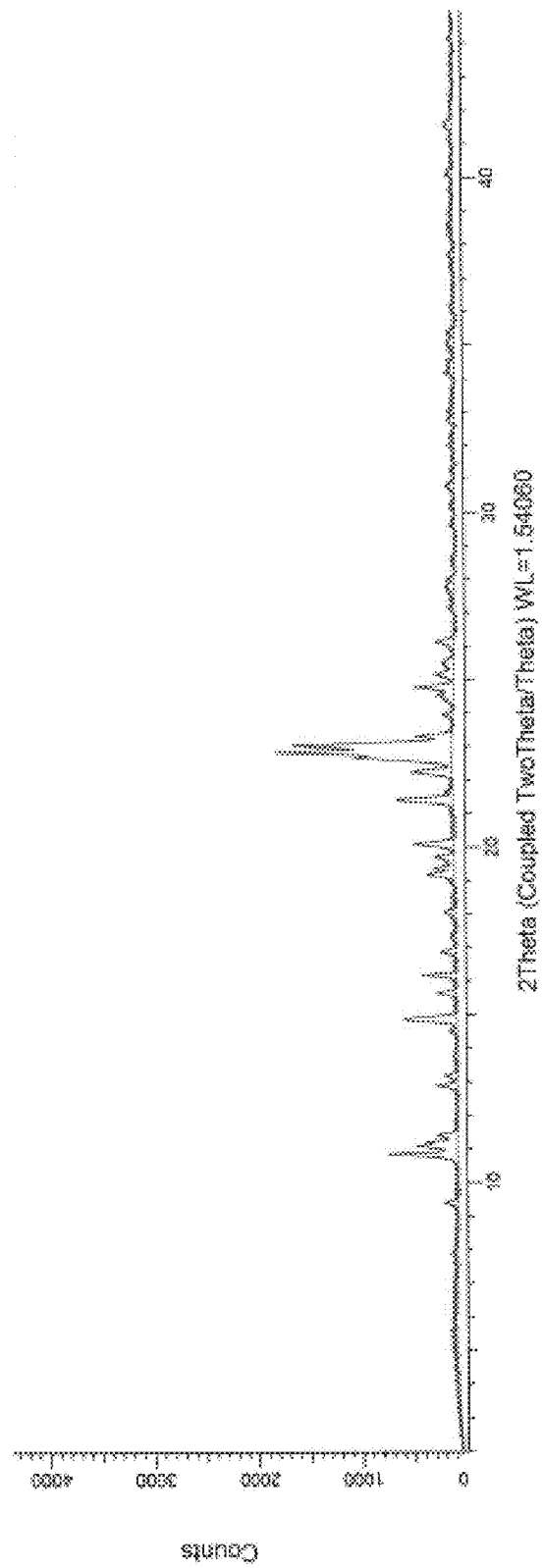
FIG. 21. XRPD analysis of Compound 1 Batch 13.
Figure 22:
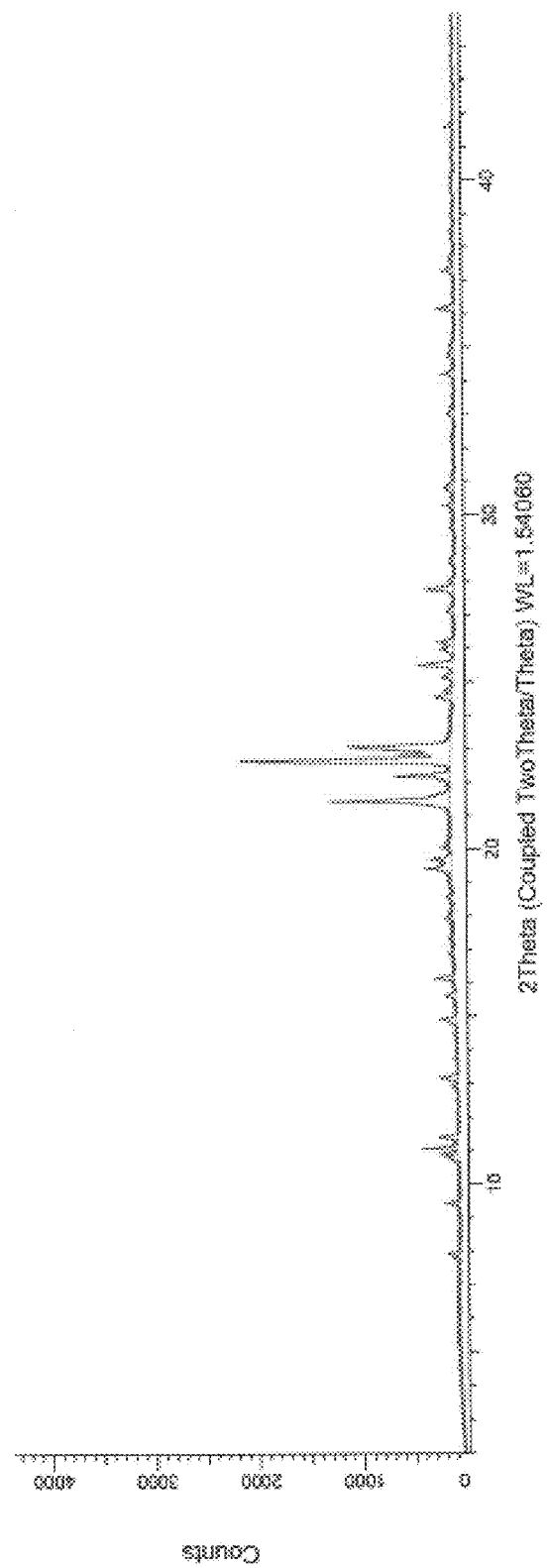
FIG. 22. XRPD analysis of Compound 1 Batch 14.
Figure 23:
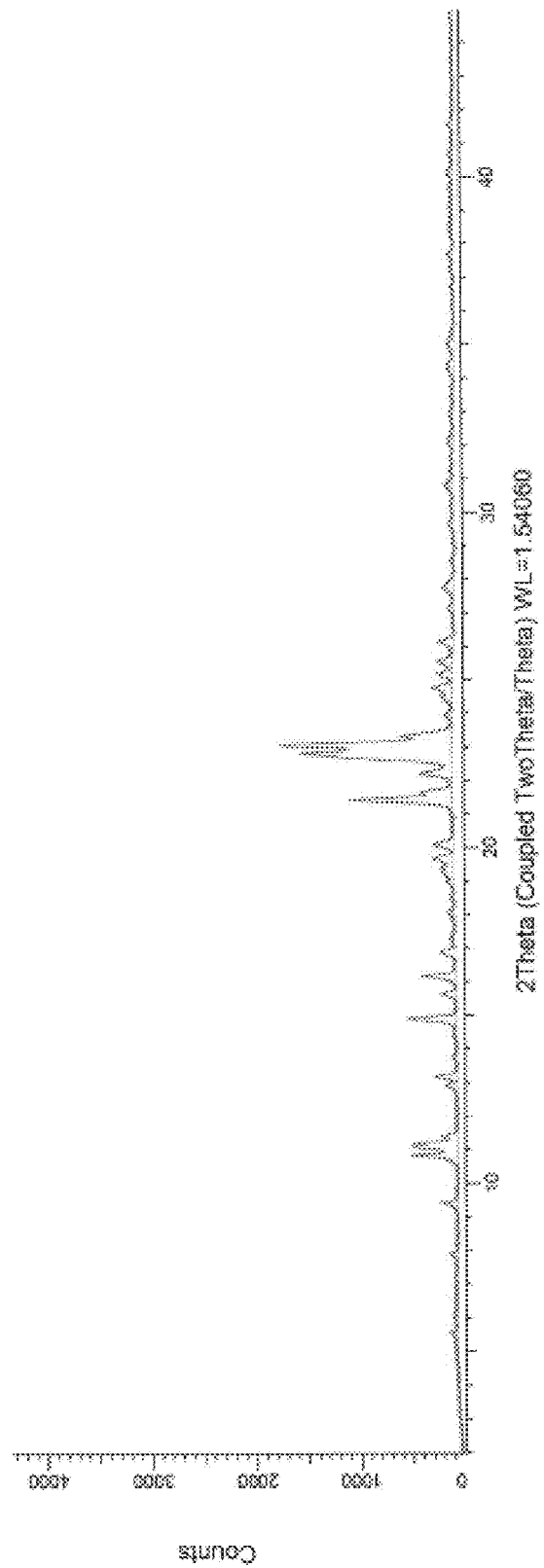
FIG. 23. XRPD analysis of Compound 1 Batch 19.
Figure 24:
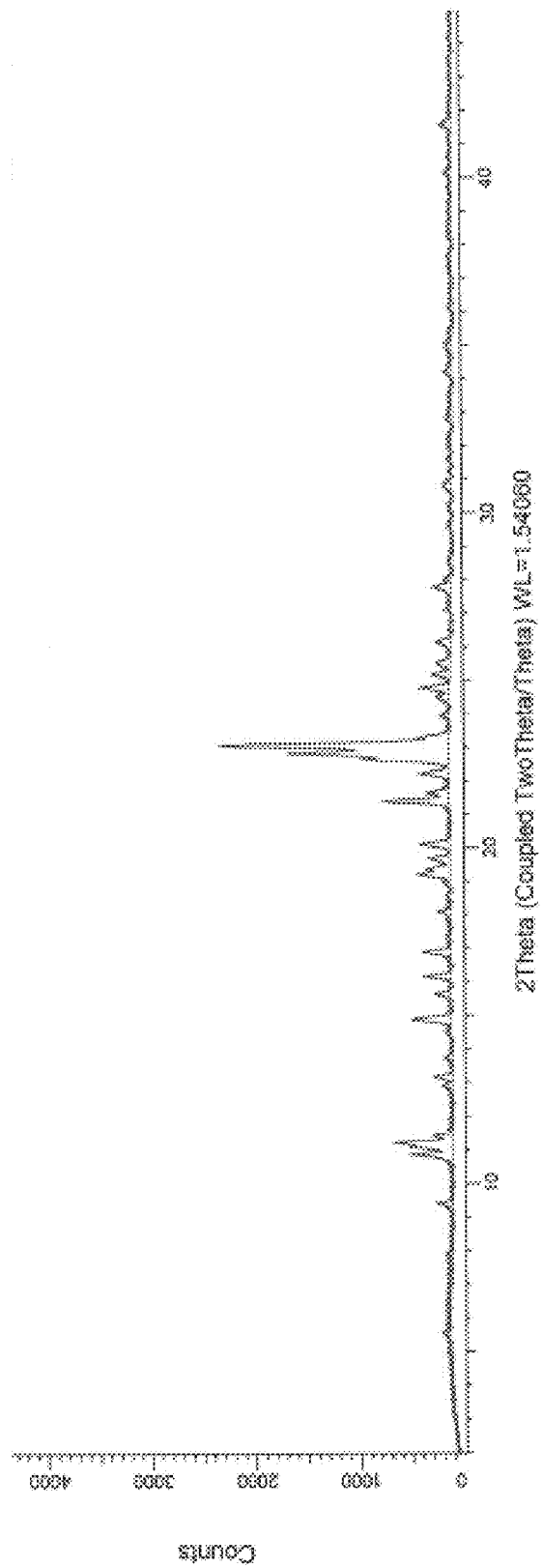
FIG. 24. XRPD analysis of Compound 1 Batch 16.
Figure 25:
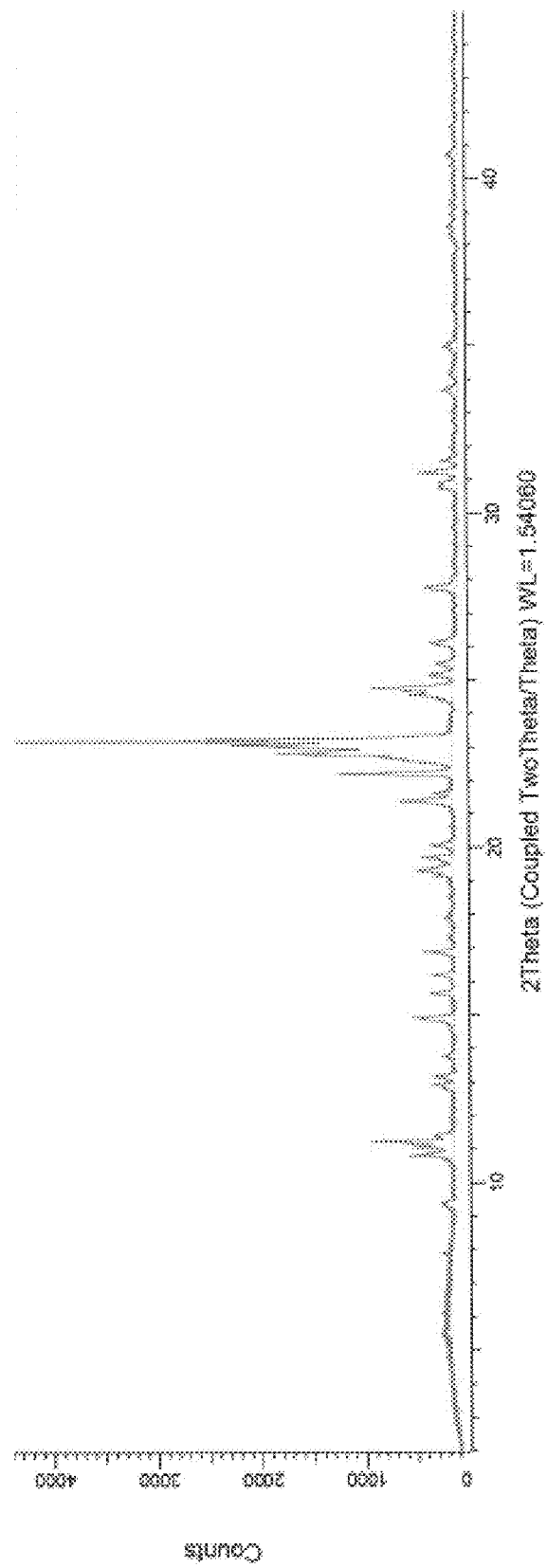
FIG. 25. XRPD analysis of Compound 1 Batch 17.

| Batch number | Method of generation | XRPD data | Crystallinity by XRPD |
|---|---|---|---|
| 2 | Method A | | |
| 3 | Method A | FIG. 19 | 74.4% |
| 4 | Method A | | |
| 5 | Method B | | |
| 6 | Method B | | |
| 11 | Method A then purified by Method B | | |
| 12 | Method B | FIG. 11 | |
| 13 | Method B | FIG. 21 | 70.2% |
| 14 | Method B | FIG. 22 | 56.2% |
| 15 | Method C | FIG. 12 | |
| 16 | Method C | FIG. 24 | 65.2% |
| 17 | Method C then purified by prep-HPLC and lyophilised | FIG. 25 | 63.7% |
| 18 (stored batch 12) | Batch 12, stored as solid at −20° C. for 20 months | FIG. 20 | 70.4% |
| 19 (stored batch 15) | Batch 15, stored as solid at −20° C. for 14 months | FIG. 23 | 69.7% |

It should be mentioned that the temperature increases during XRPD analysis. As Compound 1 has a low melting point (and the amorphous form is contemplated to have a lower melting point than the crystalline form), the degree of crystallinity given in the table above may be regarded as minimum values.

Batch 3.

Figure 2:
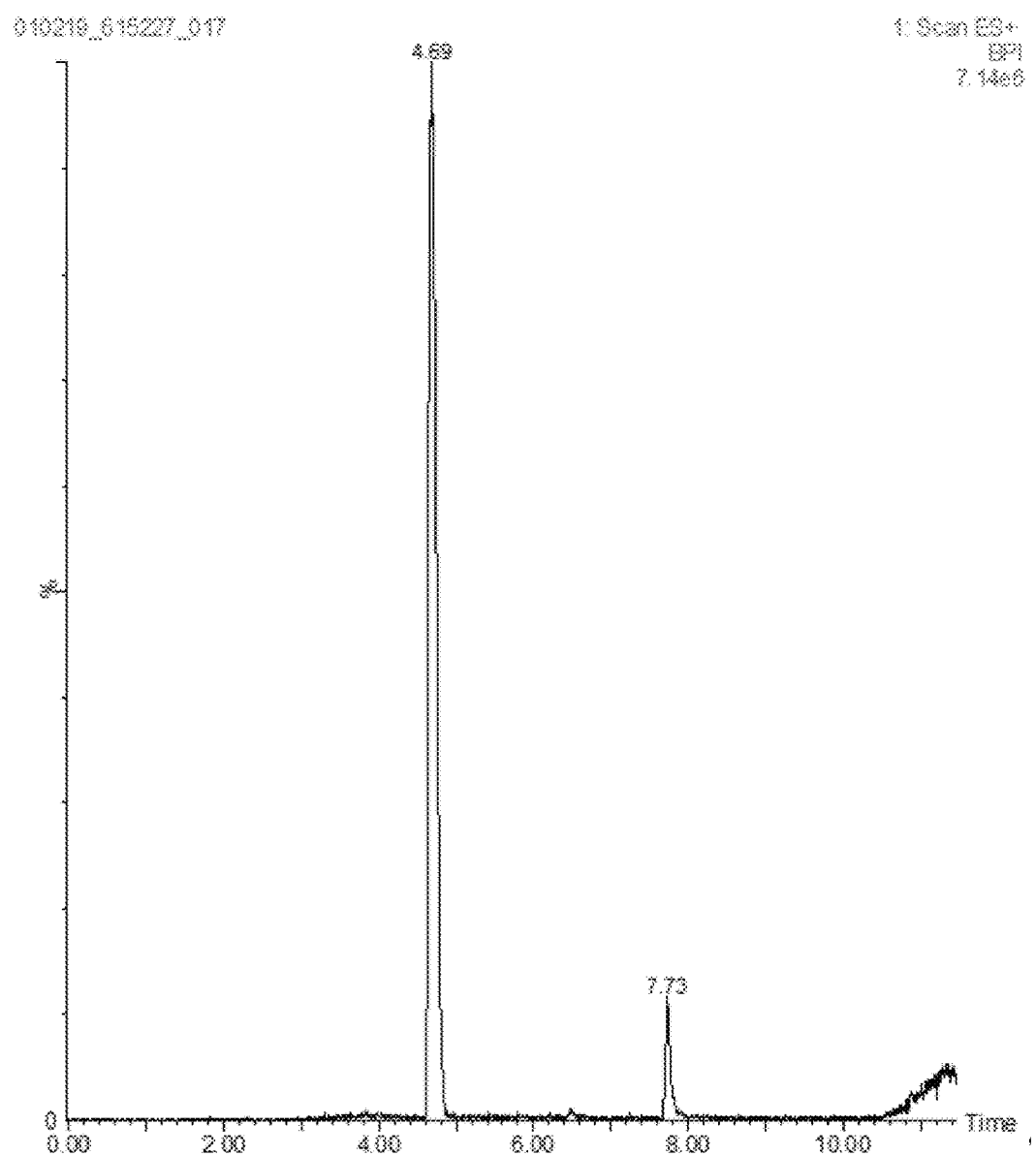
FIG. 2. LCMS analysis of Compound 1 Batch 3 depicting total ion count on a normalised scale versus time using HPLC Method 2.
Figure 3:
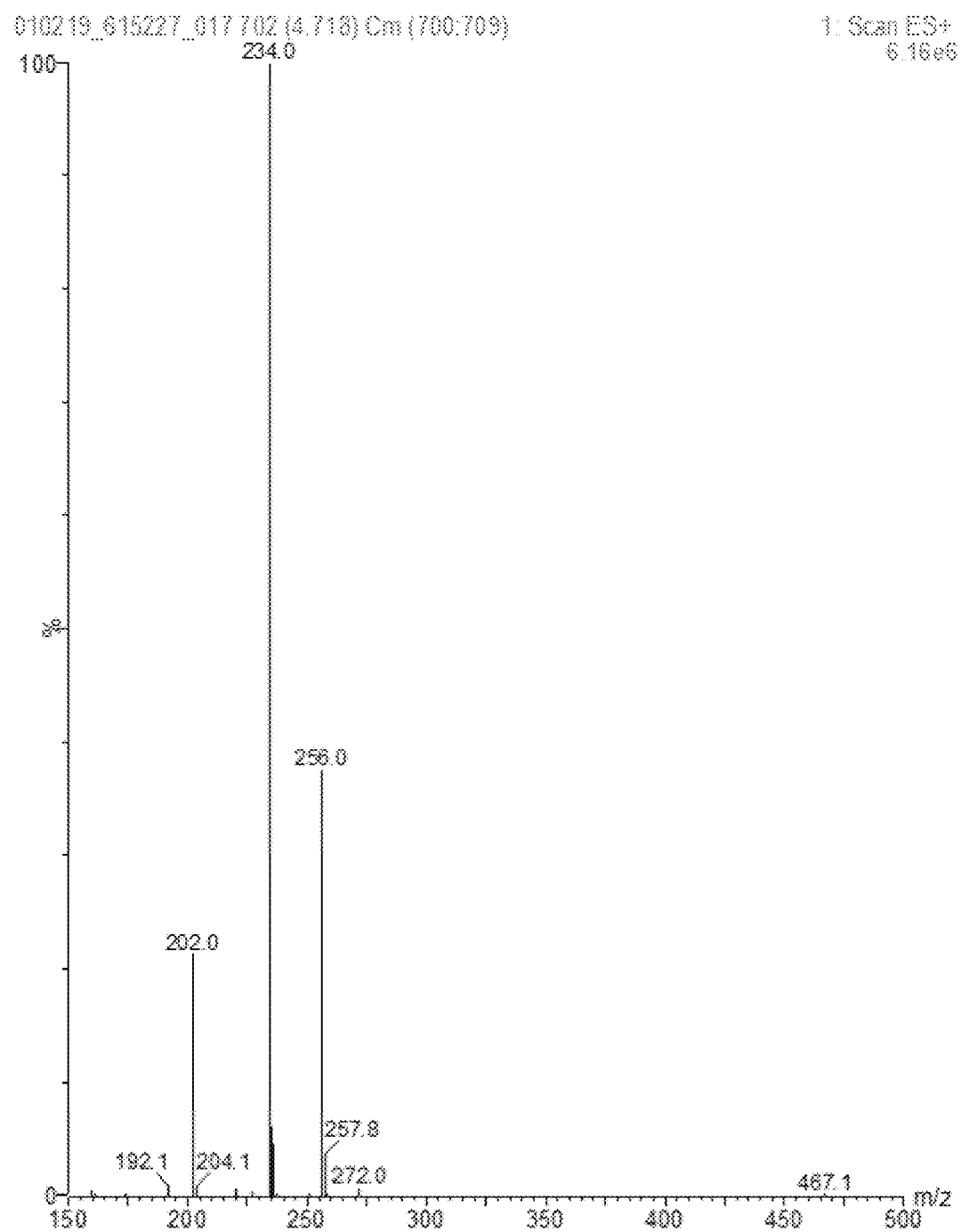
FIG. 3. LCMS analysis of Compound 1 Batch 3 depicting intensity (%) versus m/z using HPLC Method 2.

In TGA analysis the Batch 3 had a loss of 0.04% by weight at temperatures 20-150° C. FIGS. 1-3 shows the spectra from LCMS analysis of Batch 3. The melting point of Batch 3 was 50.4° C. as determined from Differential Scanning Calorimetry (DSC).

Batch 12.

Batch 12 was analysed by same methods as used for analysis of the above described Batch 3.

Figure 4:
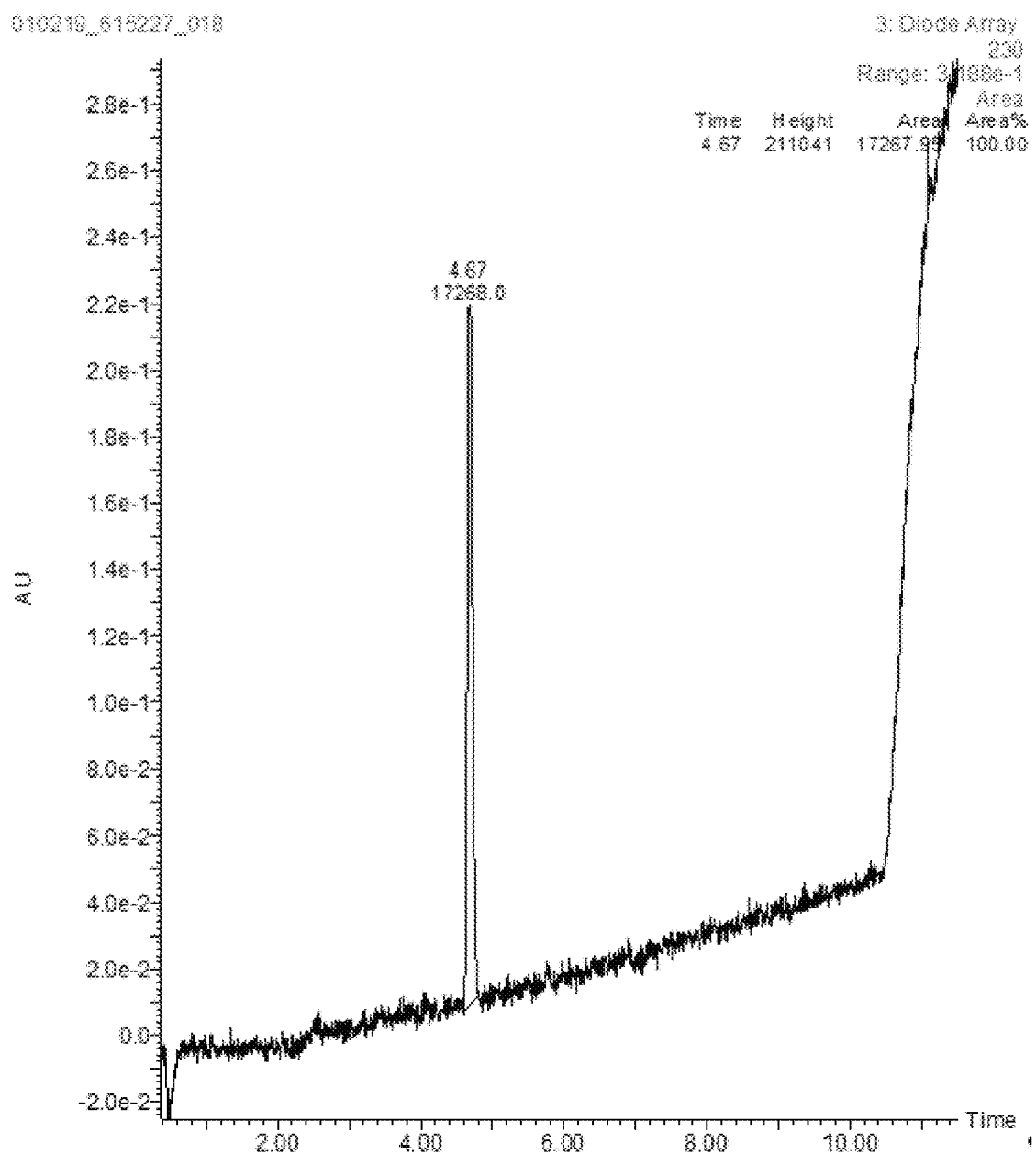
FIG. 4. LCMS analysis of Compound 1 Batch 12 depicting Absorbance Units (AU) versus time using HPLC Method 2.
Figure 5:
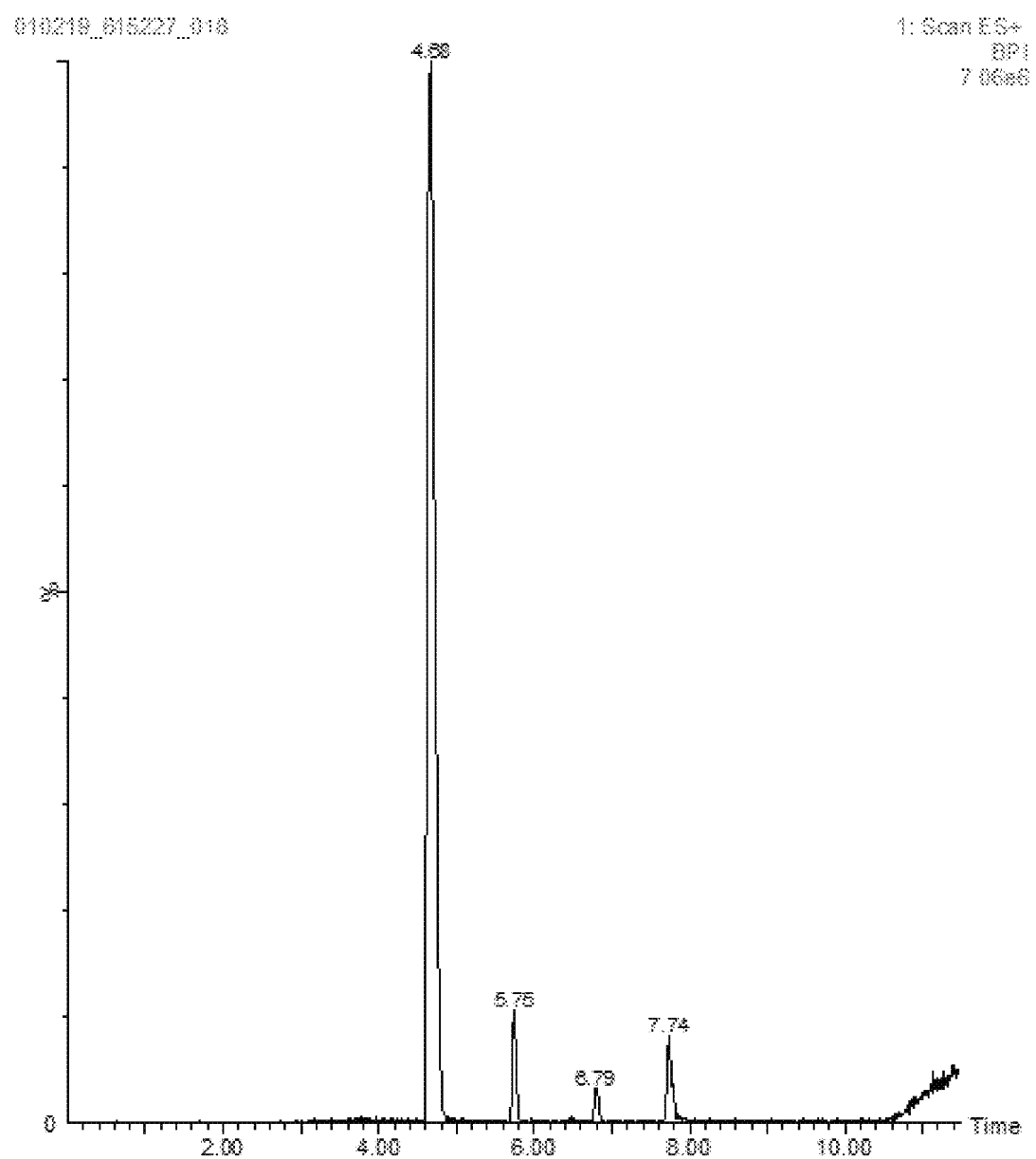
FIG. 5. LCMS analysis of Compound 1 Batch 12 depicting total ion count on a normalised scale versus time using HPLC Method 2.
Figure 6:
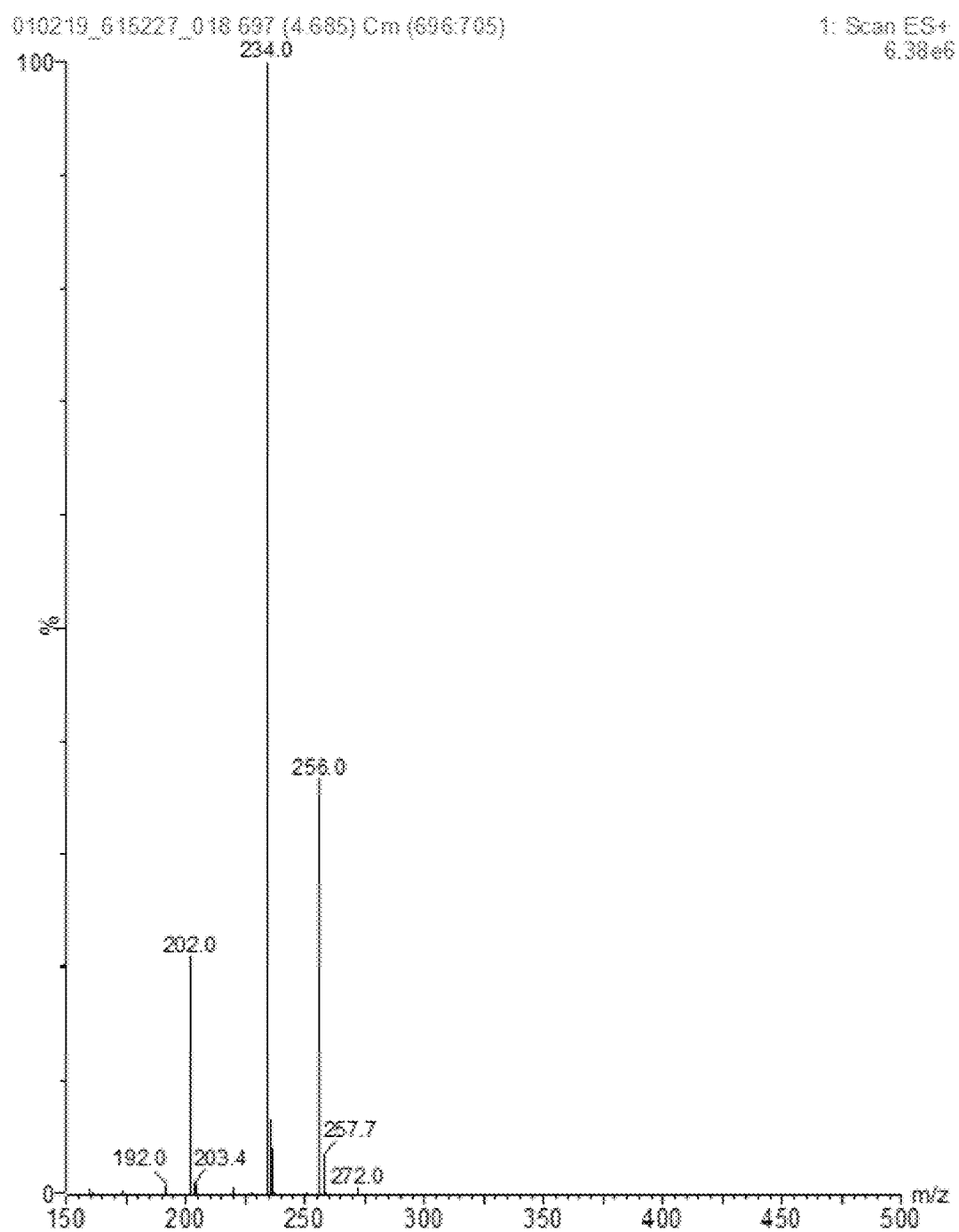
FIG. 6. LCMS analysis of Compound 1 Batch 12 depicting intensity (%) versus m/z using HPLC Method 2.

The loss in TGA analysis was 0.12% by weight at temperatures 20-150° C. Results from LCMS are depicted in FIGS. 4-6, the purity by qNMR was 96.1% and the melting point was 48.6° C.

Batch 13.

Batch 13 was analysed by same methods as used for analysis of the above batches. The loss in TGA analysis was 0.18% by weight at temperatures 20-150° C. Spectra from LCMS are not shown but results summarised in Table 5. The purity by qNMR was 96.3% and the melting point was 49.0° C.

Batch 14

Batch 14 was analysed by same methods as used for analysis of the above batches.

The loss in TGA analysis was 0.45% by weight at temperatures 20-150° C. Spectra from LCMS are not shown but results summarised in Table 5. The purity by qNMR was 91.6% and the melting point was 46.9° C.

Batch 15

Batch 15 was analysed by some of the same methods as used for analysis of the above batches.

Spectra from LCMS are not shown but results summarised in Table 5. The purity by qNMR was 98.9% and the melting point was 39° C.

Comparison of Batch Properties: Batches 3, 12, 13, 14, 15 and 16.

Table 5 also summarizes the purities, melting point and visual description of the solid Compound 1. The solid Compound 1 batches appeared as white, free-flowing powder, c.f. Table 5.

Additionally, Table 5 shows the solubility of the prepared Compound 1 batches were all at least 366-398 mg/ml and the appearance of such a formulation in water to visually appear as a clear and transparent or translucent solution.

TABLE 5

Summary of results from analyses of different batches of Compound 1.

| | Batch 3 | Batch 12 | Batch 13 | Batch 14 | Batch 15 | Batch 16 |
|---|---|---|---|---|---|---|
| Final Purification Method | Purified by silica gel column chromatography | Washed, dried and solvent removal | Washed, dried and solvent removal | Washed, dried and solvent removal | Washed, precipitated and dried. | Washed, precipitated and dried. |
| Purity by high pH HPLC (%) | 99.1 | 97.7 | 96.7 | 99.3 | 98.5 | 98.1 |
| Purity assay by qNMR (%) | 98.1 | 96.1 | 96.3 | 91.7 | 98.9 | 95.6 |
| Melting Point (° C.) | 50.4 | 48.6 | 49.0 | 46.9 | 39 | |
| Visual Description of Form | White, free-flowing powder; some 'clumped' material | Large white waxy lumps; some white, free-flowing powder | Large white waxy lumps; some white, free-flowing powder | Large white waxy lumps; some white, free-flowing powder | White, free-flowing powder | White, free-flowing powder |
| 400 mg Compound in 0.7 ml Water, Measured Conc. (mg/ml) | 381 | 378 | 395 | 366 | 414 | 435 |

TABLE 5-continued

Summary of results from analyses of different batches of Compound 1.

| | Batch 3 Purified by silica gel column chromatography | Batch 12 Washed, dried and solvent removal | Batch 13 Washed, dried and solvent removal | Batch 14 Washed, dried and solvent removal | Batch 15 Washed, precipitated and dried. | Batch 16 Washed, precipitated and dried. |
|---|---|---|---|---|---|---|
| Final Purification Method | | | | | | |
| Visual Description of Formulation in Water | Colourless, transparent solution | Cloudy, translucent solution | Colourless, transparent solution | Colourless, transparent solution | Colourless, transparent solution | Colourless, transparent solution |

TABLE 6

Summary of the analysis of the Compound 1 batches re purity and impurities (LCMS2 High pH Impurity Profiling).

| | | | | | | |
|---|---|---|---|---|---|---|
| RT (min) | 0.69 | 1.57 | 1.86 | 2.18 | 2.22 | 6.24 |
| RRT (min) | 0.439 | 1.000 | 1.185 | 1.389 | 1.414 | 3.975 |
| Apparent molecular weight | 161.0 | 233.0 | 319.9 | 247.0 | 305.0 | 278.0 |
| Structure (proposed from m/z) | [structure] | [structure] | TBC | TBC | TBC | TBC |
| % at 234 nm, batch 3 | 0.52 | 99.14 | | 0.35 | | |
| % at 234 nm, batch 12 | | 97.65 | 1.41 | 0.24 | 0.38 | 0.32 |
| % at 234 nm, batch 13 | 0.47 | 96.71 | 2.44 | 0.39 | | |
| % at 234 nm, batch 14 | 0.34 | 99.34 | | 0.32 | | |

Example 3

Preparation of Aqueous Formulations of Compound 1

Formulation Protocol

1. Weigh out the required amount of Compound 1 then add the required amount of excipient (0.9% w/v saline, 100 mM PBS pH 7.4, water) to the solid Compound 1 to give the required mg/ml concentration of Compound 1. For example, for a 400 mg/ml formulation of Compound 1 in water, weigh out 400 mg of Compound 1 and add 0.7 ml of water.
2. Sonicate the solution for 10 mins and then shake for 20 mins to ensure that Compound 1 is fully dissolved.
3. The solution can be centrifuged (13000 rpm, 10 mins) to remove any particulates if required.
4. The solution can be sterile filtered if required.

TABLE 7

Data for formulation in water of different batches of Compound 1 prepared sccording to the protocol above

| Sample | Target Conc. (mg/ml) | Inj. Vol. (μl) | Dilution factor | Calculated Conc. (mg/ml) | Purity (%) |
|---|---|---|---|---|---|
| Batch 3 in tap water | 400 | 2 | 1000 | 381 | 98.8 |
| Batch 12 in tap water | 400 | 2 | 1000 | 378 | 99.2 |
| Batch 13 in tap water | 400 | 2 | 1000 | 395 | 99.1 |
| Batch 14 in tap water | 400 | 2 | 1000 | 366 | 99.4 |

Formulation 50% w/v

Four batches of Compound 1 were formulated in PBS at 50% w/v.

~500 mg of compound was weighed into a vial, ~500 μl 100 mM PBS pH 7.4 added and the vial was sonicated for 10 mins then shaken for 20 mins. A sample was then removed, diluted 1/2000 and the concentration calculated by HPLC analysis.

TABLE 8

Preparation of Compound 1 formulations in PBS at pH 7.4. The concentration of Compound 1 was measured in the soluble formulation by HPLC.

| Sample | Amount Compound 1 added (mg) | Amount 100 mM PBS pH 7.4 added (μl) | Calculated concentration by HPLC, (mg/ml) |
|---|---|---|---|
| Batch 3 | 525 | 525 | 535 |
| Batch 4 | 514 | 514 | 526 |

TABLE 8-continued

Preparation of Compound 1 formulations in PBS at pH 7.4. The concentration of Compound 1 was measured in the soluble formulation by HPLC.

| Sample | Amount Compound 1 added (mg) | Amount 100 mM PBS pH 7.4 added (µl) | Calculated concentration by HPLC, (mg/ml) |
|---|---|---|---|
| Batch 5 | 494 | 494 | 531 |
| Batch 6 | 481 | 481 | 543 |

Formulation Liquid Compound 1

Compound 1 batch 3 was heated in an oven to 60° C. for 20 mins, at which point it became a translucent pale-yellow liquid. 100 mM PBS pH 7.4 (20% v/v) was added and the solution was mixed for 20 mins on a shaker. After this time, the solution had cooled to room temperature and remained a translucent liquid. The solution was placed at 4° C. for 72 hours. Observation after this time confirmed that it remained a translucent liquid.

Formulation Summary

The amount of Compound 1 that can be formulated in aqueous solutions such as 0.9% w/v saline, 100 mM PBS pH 7.4 or water seems to have no reachable limit. This can possibly be explained by the melting point of Compound 1 which was measured to approx. 47-50° C. in several batches. When the aqueous solution is added to the solid, it disrupts the intramolecular interactions of Compound 1 molecules it becomes miscible with water.

Example 4

Gel Formulation

Formulate Compound 1 into gel packs at 2.25 mg/ml.

Experimental Details

One HydroGel gel pack (Clear $H_2O$ hydrogel, 8 oz pouch, HydroGel, Portland, ME) was taken and divided up into falcon tubes for different experiments.

Firstly, blue food dye was used to see how easily an aqueous solution could be mixed into the gel. Two samples of the gel were taken, one was kept at RT, the other was melted in the microwave (1 min). The blue food dye (1% v/v) was added and the solutions were mixed. Mixing is much more efficient when the gel has been melted. The dye can be fully incorporated after mixing for <10 s.

Next, the dye solution was replaced for a solution of Compound 1.

Water was added to Compound 1 (225 mg/ml, 100× required concentration) and sonicated for 20 mins then shaken for 30 mins. A sample was taken for HPLC analysis to check the concentration.

TABLE 9

Compound 1 measured concentration in water stock.

| Sample | Expected conc, (mg/ml) | Inj. Vol. (ul) | Dilution factor | Calc, mg/ml | Purity (%) |
|---|---|---|---|---|---|
| Water stock for addition into gel | 225 | 1 | 100 | 222.749 | 98.8 |

The analysis showed that Compound 1 had been fully solubilised.

Another 2 portions of the gel were melted, and the Compound 1 water solution was added (1% v/v). The gels were shaken for the same length of time as when the dye was added (10 s). The gels were left to set.

Once the gels had set, samples were taken for HPLC analysis to check Compound 1 was evenly distributed.

Sampling procedure

1. A sample of the gel (100 mg) was added to an Eppendorf and MeOH was added (0.9 ml, 1/10 dilution)
2. The sample was shake on a vibrax for 30 mins
3. The sample was centrifuged (13000 rpm, 10 mins)
4. The supernatant was taken for HPLC analysis

TABLE 10

Compound 1 measured concentration in gel samples.

| Sample | Expected conc, (mg/ml) | Inj. Vol. (ul) | Dilution factor | Calc. mg/ml | Purity (%) |
|---|---|---|---|---|---|
| 4° C. | 2.25 | 5 | 10 | 2.07 | 99.4 |
| 37° C. | 2.25 | 5 | 10 | 2.03 | 99.5 |

The concentration of Compound 1 was slightly lower than the 2.25 mg/ml expected, but the two samples are in good agreement, which suggests Compound 1 has been evenly distributed and that the dilution factor is slightly out.

One of the gel samples was kept at RT (room temperature) and the other at 4° C. to test the stability of Compound 1 in the gel.

Stability of Gel Formulation

The gel was sampled as above at regular timepoint to check the stability at both 4° C. and RT. Data from these experiments are shown in Tables 11-12.

TABLE 11

Compound 1 concentrations in gel samples taken over 20 days storage at 4° C.

| Time (days) | Expected conc. (mg/ml) | Inj. Vol. (ul) | Dilution factor | Calc. mg/ml | AUC (% of T = 0) | Purity at 230 nm (%) |
|---|---|---|---|---|---|---|
| 0 | 2.25 | 5 | 10 | 2.071 | 100.0 | 99.4 |
| 1 | 2.25 | 5 | 10 | 2.024 | 97.8 | 99.4 |
| 5 | 2.25 | 5 | 10 | 1.937 | 93.5 | 99.4 |
| 7 | 2.25 | 5 | 10 | 1.979 | 95.6 | 99.4 |
| 11 | 2.25 | 5 | 10 | 2.007 | 96.9 | 99.4 |
| 14 | 2.25 | 5 | 10 | 2.167 | 104.7 | 99.4 |
| 20 | 2.25 | 5 | 10 | 2.218 | 107.1 | 99.5 |

TABLE 12

Compound 1 concentrations in gel samples taken over 20 days storage at RT (approx. 20° C.).

| Time (days) | Expected conc. (mg/ml) | Inj. Vol. (ul) | Dilution factor | Calc. mg/ml | AUC (% of T = 0) | Purity at 230 nm (%) |
|---|---|---|---|---|---|---|
| 0 | 2.25 | 5 | 10 | 2.034 | 100.0 | 99.5 |
| 1 | 2.25 | 5 | 10 | 1.746 | 85.8 | 99.5 |
| 5 | 2.25 | 5 | 10 | 2.053 | 100.9 | 99.4 |
| 7 | 2.25 | 5 | 10 | 1.721 | 84.6 | 99.2 |
| 11 | 2.25 | 5 | 10 | 1.889 | 92.9 | 99.1 |
| 14 | 2.25 | 5 | 10 | 2.739 | 134.6 | 99.4 |
| 20 | 2.25 | 5 | 10 | 2.273 | 111.7 | 99.4 |

The general trend in the data, especially the purity at 230 nm data suggests Compound 1 is stable in the gel formulation for at least 20 days. The AUC data has more error due to inaccuracies in weighing gel samples for extraction and possibly differences in localised concentration of Compound 1 in the gel.

Protocol for Preparation of Gel Formulation

Prepare a 100× concentrated solution of Compound 1 in water, so it can be added to the gel at 1/100 of the volume of the gel. The example given is for a 2.25 mg/ml final concentration in a 200 ml gel pack, therefore requires 2 ml of 100× Compound 1 in water (225 mg/ml). It is also suggested that a food dye is added to the stock solution and the combined solution is injected into the gel pack (provided it will cause no adverse effect to the study). This gives a visual check that the Compound 1 solution has been evenly distributed in the gel. If the food dye is included, it is recommended that the food dye is also added to the gel of control group.

1. Weigh out 500 mg Compound 1 into a 3 ml vial (or similar)
2. Add 2 ml water (the addition of 2 ml water to 500 mg Compound 1 accounts for the volume of the solid Compound 1 and has been confirmed by HPLC calibration curve to be 225 mg/ml), sonicate for 20 mins, then shake for 30 mins (the solution may remain slightly cloudy). Add 1 ml of a natural food dye (the food dye will help to show that even distribution has been achieved).
3. This solution can be sterile filtered if necessary
4. Heat the unopened gel pack by submersing in 70° C. water for 10 mins and the gel will become a mobile liquid
5. Take up the Compound 1 solution into a needle/syringe (with/without the food dye)
6. Inject the Compound 1 solution (and the food dye) into the gel pack by piercing a small hole in the gel pack with the needle
7. Re-seal the gel pack at the injection site with tape
8. Shake the gel pack vigorously for 5 mins to get even distribution of Compound 1 (if the food dye is included it will become evident when the injected solution is evenly distributed by a colour change of the gel)
9. Allow the gel to solidify, this takes around 45 mins at room temperature
10. Use the gel or store sealed at 4° C. (it is recommended that the gel is stored at 4° C. for a maximum of 14 days once opened)
11. Compound 1 is stable in the gel for at least 14 days at 4° C. and room temperature Test of Protocol The gel formulation was prepared according to the protocol and HPLC analysis showed that the correct concentration of Compound 1 was achieved in the water stock and the gel formulation.

TABLE 13

Compound 1 concentrations the water stock solution and the gel formulation

| Sample | Expected conc. (mg/ml) | Inj. Vol. (ul) | Dilution factor | Calc. mg/ml | Purity at 230 nm (%) |
| --- | --- | --- | --- | --- | --- |
| Water stock for addition into gel | 225 | 2 | 200 | 229.496 | 99.0 |
| Gel formulation | 2.25 | 5 | 10 | 2.355 | 99.7 |

2 ml of the water stock was added to 1 ml of food dye. This was diluted and analysed by HPLC. The AUC for the water stock diluted with food dye was 0.63 times that of the water stock before the dilution, indicating that Compound 1 remains soluble when diluted with food dye.

OUTCOME/CONCLUSION

Compound 1 can be formulated in aqueous gel packs at 2.25 mg/ml and is stable at both 4° C. and RT for at least 20 days.

Example 5

Saline Formulation of Compound 1

1. Weigh out 400 mg Compound 1 and add 0.7 ml saline (0.9% w/v)
2. Sonicate for 20 mins then shake for 30 mins or until all compound is soluble by eye Compound 1 Freeze/Thaw Stability Method 1. Saline (0.9% w/v) was added to Compound 1 (1 mg/ml) then sonicated for 10 mins until fully dissolved
2. A sample was taken for HPLC analysis (F/T 0)
3. The solution was frozen at −80° C. overnight.
4. The solution was thawed, and a sample was taken for HPLC analysis (F/T 1)
5. Steps 3&4 were repeated for 3 cycles

TABLE 14

Purity of Compound 1 upon Freeze/Thaw (FT) cycles.

| Sample | FT cycle | Expected conc. (mg/ml) | Inj. Vol. (ul) | Dilution factor | Calc. mg/ml | Purity (%) |
| --- | --- | --- | --- | --- | --- | --- |
| Compound 1 in saline | 0 | 1 | 2 | 1 | 1.157 | 98.9 |
| | 1 | 1 | 2 | 1 | 1.148 | 98.8 |
| | 2 | 1 | 2 | 1 | 1.153 | 98.9 |
| | 3 | 1 | 2 | 1 | 1.146 | 98.8 |

The results (Table 14) show that there is no significant change in assay or purity of Compound 1 in saline, so Compound 1 is stable for at least 3 freeze/thaw cycles.

Compound 1 RT Stability

Method:
1. Saline (0.9% w/v) was added to Compound 1 (1 mg/ml) then sonicated for 10 mins until fully dissolved
2. A sample was taken for HPLC analysis (T=0)
3. The solution was stored at RT
4. Samples were taken periodically for HPLC analysis of stability Results:

The results showed that there is no significant change in assay or purity of Compound 1 in saline (data not depicted), so Compound 1 is stable for at least 14 days at room temperature.

Compound 1 200-500 mg/ml Formulation

Method:
1. Saline (0.9% w/v) was added to Compound 1 batch 11 in different amounts then sonicated for 10 mins—the samples remained slightly cloudy
2. The samples were shaken for 30 mins at which point the solutions became translucent
3. The solutions were diluted for HPLC analysis Results:

TABLE 15

Purity of Compound 1 at increasing concentrations in saline solution.

| Sample | RT (min) | Inj. Vol. (ul) | Dilution factor | Calc. mg/ml | Purity (%) |
|---|---|---|---|---|---|
| 400 mg Compound 1 in 1 ml saline | 8.21 | 5 | 1000 | 261 | 98.7 |
| 400 mg Compound 1 in 0.7 ml saline | 8.21 | 5 | 1000 | 403 | 98.7 |
| 400 mg Compound 1 in 0.4 ml saline | 8.21 | 5 | 1000 | 545 | 98.6 |

The results show (Table 15) that over 500 mg/ml Compound 1 in saline solution can be reached.

Protocol for Transfer (400 mg/ml Formulation)

3. Weigh out 400 mg Compound 1 batch 11 and add 0.7 ml saline (0.9% w/v)
4. Sonicate for 20 mins then shake for 30 mins or until all compound is soluble by eye

OUTCOME/CONCLUSION

Compound 1 Freeze/Thaw Stability

Compound 1 is stable for at least 3 freeze/thaw cycles.

Compound 1 RT Stability

Compound 1 is stable for at least 14 days at room temperature (data collection to be continued).

Compound 1 400 mg/ml Formulation

Over 500 mg/ml Compound 1 in saline can be reached.

Example 6

Compound 1 Stability in Water and DMSO

Compound 1 was separately dissolved in water and DMSO at a concentration of 1 mg/ml and stored at RT, 37° C. and 65° C. for stability over a 40 day period.

TABLE 16

Compound 1 in water at RT in the dark (conc. 1 mg/ml) with purity measurements.

| Time (days) | AUC at 230 nm | AUC (% of T = 0) | Purity at 230 nm (%) | Purity by LCMS (%) |
|---|---|---|---|---|
| 0 | 9041 | 100.0 | 100.0 | 100.0 |
| 1 | 8847 | 97.9 | 100.0 | 99.2 |
| 2 | 8807 | 97.4 | 100.0 | 98.3 |
| 4 | 8045 | 89.0 | 100.0 | 99.0 |
| 7 | 8588 | 95.0 | 100.0 | 99.2 |
| 11 | 8554 | 94.6 | 100.0 | 98.7 |
| 14 | 8662 | 95.8 | 100.0 | 95.6 |
| 17 | 8873 | 98.1 | 100.0 | 98.1 |
| 23 | 8561 | 94.7 | 100.0 | 98.9 |
| 38 | 8555 | 94.6 | 100.0 | 98.7 |

Small loss in purity and assay is noted in Compound 1 in water at room temperature over the period of 38 days.

TABLE 17

Compound 1 in water at 37° C. in the dark (conc. 1 mg/ml) with purity measurements.

| Time (days) | AUC at 230 nm | AUG (% of T = 0) | Purity at 230 nm (%) | Purity by LCMS (%) |
|---|---|---|---|---|
| 0 | 9044 | 100.0 | 100.0 | 100.0 |
| 1 | 9798 | 108.3 | 100.0 | 99.6 |
| 2 | 8681 | 96.0 | 100.0 | 97.5 |
| 4 | 8156 | 90.2 | 100.0 | 99.0 |
| 7 | 9106 | 100.7 | 100.0 | 98.9 |
| 11 | 8577 | 94.8 | 100.0 | 98.4 |
| 14 | 7777 | 86.0 | 100.0 | 96.9 |
| 17 | 7928 | 87.7 | 100.0 | 93.2 |
| 23 | 7567 | 83.7 | 100.0 | 98.4 |
| 38 | 7579 | 83.8 | 100.0 | 98.3 |

Loss in purity and assay is noted in Compound 1 in water at 37° C. over the period of 38 days. Loss in assay is more 2 significant than that observed in water at room temperature.

TABLE 18

Compound 1 in water at 65° C. in the dark (conc. 1 mg/ml) with purity measurements.

| Time (days) | AUG at 230 nm | AUG (% of T = 0) | Purity at 230 nm (%) | Purity by LCMS (%) |
|---|---|---|---|---|
| 0 | 8741 | 100.0 | 100.0 | 100.0 |
| 1 | 8614 | 98.5 | 100.0 | 98.3 |
| 2 | 8410 | 96.2 | 100.0 | 97.3 |
| 5 | 7512 | 85.9 | 100.0 | 95.9 |
| 8 | 8750 | 100.1 | 100.0 | 99.1 |
| 14 | 9095 | 104.0 | 100.0 | 99.0 |
| 29 | 4521 | 50.0 | 100.0 | 89.1 |

Loss in purity and assay is noted in Compound 1 in water over the period of 29 days. Loss in purity and assay is me re significant than that observed in water at 37 °C.

TABLE 19

Compound 1 in DMSO at 37° C. in the dark (conc. 1 mg/ml) with purity measurements.

| Time (days) | AUC at 230 nm | AUC (% of T = 0) | Purity at 230 nm (%) | Purity by LCMS (%) |
|---|---|---|---|---|
| 0 | 16363 | 100.0 | 100.0 | 98.4 |
| 1 | 17465 | 106.7 | 100.0 | 98.4 |
| 4 | 17041 | 104.1 | 100.0 | 98.2 |
| 8 | 17644 | 107.8 | 100.0 | 98.2 |
| 11 | 17434 | 106.5 | 100.0 | 99.0 |
| 14 | 17557 | 107.3 | 100.0 | 98.2 |
| 22 | 17353 | 106.1 | 100.0 | 98.0 |
| 37 | 17904 | 109.4 | 100.0 | 97.6 |

No significant loss in purity or assay is noted in Compound 1 in DMSO at 37° C. over the period of 37 days.

TABLE 20

Compound 1 in DMSO at 65° C. in the dark (conc 1 mg/ml) with purity measurements.

| Time (days) | AUC at 230 nm | AUC (% of T = 0) | Purity at 230 nm (%) | Purity by LCMS (%) |
|---|---|---|---|---|
| 0 | 15834 | 100.0 | 100.0 | 98.1 |
| 1 | 16974 | 107.2 | 100.0 | 98.3 |
| 2 | 16185 | 102.2 | 100.0 | 96.8 |
| 5 | 17175 | 108.5 | 100.0 | 99.2 |

TABLE 20-continued

Compound 1 in DMSO at 65° C. in the dark (conc 1 mg/ml) with purity measurements.

| Time (days) | AUC at 230 nm | AUC (% of T = 0) | Purity at 230 nm (%) | Purity by LCMS (%) |
|---|---|---|---|---|
| 8 | 14415 | 91.0 | 100.0 | 96.7 |
| 14 | 13846 | 87.4 | 100.0 | 93.9 |
| 29 | 16472 | 100.7 | 100.0 | 97.7 |

No significant loss in purity or assay is noted in Compound 1 in DMSO at 65° C. over the period of 29 days.

Example 7

Analysis of Compound 1

Material from Method C (Batch 15) from Example 1 was analysed by XRPD. The data are shown in FIG. 12 and shows crystalline material.

Material from Method A (Batch 12) was also analysed by XRPD and appeared to show crystalline material with the same polymorph (FIG. 11).

Example 8

Comparison of Solubility of Compound 1 with Other Succinate Prodrugs

Solubility of Compound 1 in aqueous formulations in comparison to other succinate prodrugs was assessed by dissolving solid material in aqueous formulations and measuring the quantity in solution by HPLC(-MS). Compound 1 was seen to dissolve in water at over 350 mg/mL, PBS (pH 7.4) at 190 mg/mL and over 500 mg/mL in 0.9% saline, whereas other succinate prodrugs assessed had much lower solubility. In many cases the max solubility of other prodrugs was lower than 100 uM. See Table 21 for example solubility data in PBS pH 7.4 for other succinate prodrugs.

TABLE 21

Solubility of example succinate prodrugs

| Test article | Solubility (μM) |
|---|---|
| 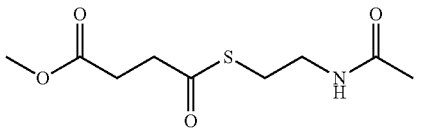 Compound 1 | >>100 (see text) |

TABLE 21-continued

Solubility of example succinate prodrugs

| Test article | Solubility (μM) |
|---|---|
| 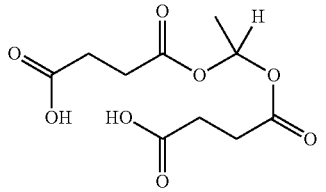 A | 52 |

Example 9

Comparison of Bioavailability of Compound 1 with Other Succinate Prodrugs

The cell penetrance and potential for oral bioavailability of Compound 1 was tested using a standard caco-2 bioavailability in vitro assay (in brief, confluent Caco-2 cells (L1, A. P., 1992; Grass, G. M, et al., 1992, Volpe, D. A., et al., 2001) in a 24 well Corning Costar Transwell format were provided by In Vitro Technologies Inc. (IVT Inc., Baltimore, Md., U.S.A.). The apical chamber contained 0.15 mL Hank's balanced buffer solution (HBBS) pH 7.4, 1% DMSO, 0.1 mM Lucifer Yellow. The basal chamber contained 0.6 mL HBBS pH 7.4, 1% DMSO. Controls and tests were incubated at 37° C. in a humidified incubator, shaken at 130 rpm for 1 h. Lucifer Yellow permeates via the paracellular (between the tight junctions) route only, a high Apparent Permeability (Papp) for Lucifer Yellow indicates cellular damage during assay and all such wells were rejected. Propranolol (good passive permeation with no known transporter effects) & acebutalol (poor passive permeation attenuated by active efflux by P-glycoprotein) were used as reference compounds. Compounds were tested in a uni- and bi-directional format by applying compound to the apical or basal chamber (at 0.01 mM). Compounds in the apical or basal chambers were analysed by HPLC-MS. Results were expressed as Apparent Permeability, Papp, (nm/s), in comparison to other succinate prodrugs, including a number from WO2015/155231. Data is presented in table 22 below and shows that the Apical to Basolateral transfer is highest for Compound 1, showing improved cell penetrance and bioavailability. This was confirmed by in vivo pharmacokinetic studies which showed Compound 1 also had a high oral bioavailability and was brain penetrant, unlike other prodrugs tested.

TABLE 22

Caco-2 bioavailability of Compound 1 in comparison to other succinate pro-drugs.

| Compound ID | $P_{app}$(A-B) nm/s |
|---|---|
| 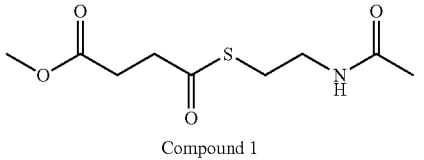 Compound 1 | 4.12 |

TABLE 22-continued
Caco-2 bioavailability of Compound 1 in comparison to other succinate pro-drugs.
| Compound ID | $P_{app}$(A-B) nm/s |
|---|---|
| 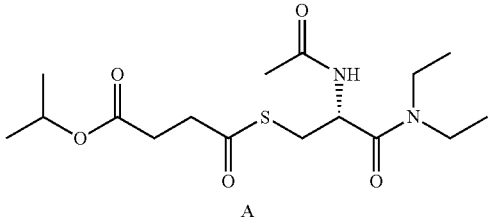 A | 3.13 |
| 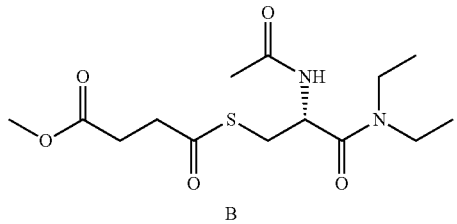 B | 1.92 |
| 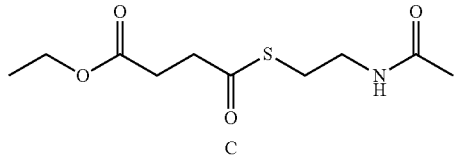 C | 1.28 |
| 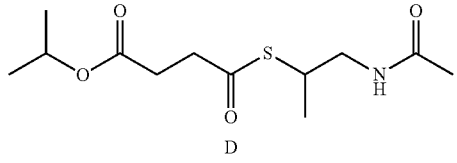 D | 1.42 |
| 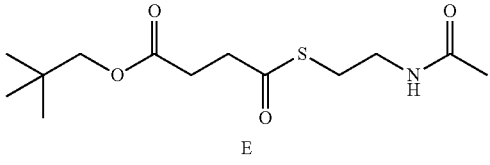 E | <0.21 |
| 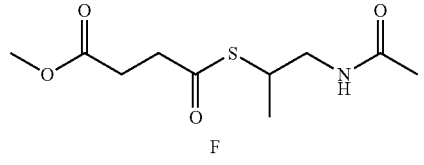 F | 1.45 |
| 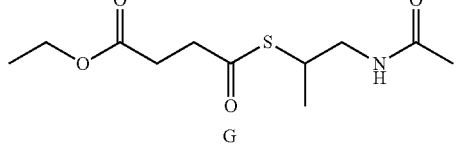 G | 0.87 |

TABLE 22-continued

Caco-2 bioavailability of Compound 1 in comparison to other succinate pro-drugs.

| Compound ID | $P_{app}$(A-B) nm/s |
|---|---|
| H | 2.62 |
| I | |
| J | 1.35 |
| K | 1.68 |
| L | 0.16 |
| M | 0.97 |

Example 10

Comparison of Thermodynamic Solubility of Different Batches of Compound 1

Two batches of Compound 1 were generated with different crystallinity. Batch 2 had higher crystallinity than Batch 3, which is regarded as having a higher degree of amorphous Compound 1—Batch 2 is therefore regarded as a more crystalline batch, whereas Batch 3 is regarded as a more amorphous batch. The methods used are discussed in this document. PBS was generated as usual (NaCl (8 g/L), KCl (0.2 g/L), disodium hydrogen phosphate anhydrous (1.42 g/L) and potassium dihydrogen phosphate anhydrous (0.24 g/L) were added to 250 mL of deionised water and the mixture stirred until all the solid had dissolved. The pH of the solution was adjusted to pH 7.4 using HCl (1 M) or NaOH (1 M) as necessary).

A sample of the more amorphous Compound 1 batch 3 was added to PBS or water to a final concentration of 258 mg/mL and sonicated for 10 minutes, then shaken for 30 minutes. Following centrifugation to remove solid material, analysis revealed a concentration of 258 mg/mL had been reached.

A sample of the more crystalline Compound 1 batch 2 was added to HPLC-grade water (Fisher) to a final concentration of 30 mg/mL and sonicated for 10 minutes, then shaken for 30 minutes. Following centrifugation to remove solid material, analysis revealed a concentration of 17 mg/mL had been reached.

A sample of the more crystalline Compound 1 batch 2 was added to HPLC-grade water (Fisher) to a final concentration of 52 mg/mL and sonicated for 20 minutes, then shaken for 1 hour. Following centrifugation to remove solid material, analysis revealed a concentration of 52 mg/mL had been reached.

As can be seen from the data presented—the more amorphous material has much higher kinetic solubility than the more crystalline material.

A sample of the more crystalline Compound 1 batch 2 was added to HPLC-grade water (Fisher) to a final concentration of 2000 mg/mL and sonicated for 20 minutes, then shaken for 1.5 hours. Following centrifugation to remove solid material, analysis revealed a concentration of 850 mg/mL had been reached. This result show that the water solubility of the more crystalline Compound is at least 850 mg/ml, i.e. it has a high water solubility, but the kinetic solubility is higher for the more amorphous Compound 1.

Example 11

Comparison of Stability of Compound 1 in Purified or Non-Purified Water

A side-by-side experiment of the stability of Compound 1 in 'purified' HPLC grade water (Fisher Scientific) and 'non-purified' tap water was set up. In brief, 1 mg/mL solutions of Compound 1 were generated in 'purified' HPLC grade water (Fisher Scientific) and 'non-purified' tap water. These were incubated at room temperature for up to 10 days. Concentration and purity of Compound 1 was assessed over time by HPLC in comparison to a standard (AUC of 8.21 RT peak at 230 nm for calculated concentration and AUC of Compound 1 peak vs impurities for purity analysis). Data presented is the average of two samples.

TABLE 23

Compound 1 batch 3 dissolved in tap water at 1 mg/ml, stored at room temperature for number of days noted in table

| Time (days) | Expected Conc. (mg/mL) | Calculated Conc. (mg/mL) | Purity (%) |
|---|---|---|---|
| 0 | 1 | 1.06 | 98.5 |
| 3 | 1 | 0.98 | 95.7 |
| 5 | 1 | 0.93 | 94.4 |
| 6 | 1 | 0.89 | 93.3 |
| 10 | 1 | 0.83 | 93.0 |

TABLE 24

Compound 1 batch 3 dissolved in HPLC grade water (Fisher Scientific) at 1 mg/ml, stored at room temperature for number of days noted in table

| Time (days) | Expected Conc. (mg/mL) | Calculated Conc. (mg/mL) | Purity (%) |
|---|---|---|---|
| 0 | 1 | 1.02 | 99.0 |
| 3 | 1 | 1.04 | 98.8 |
| 5 | 1 | 1.03 | 99.0 |
| 6 | 1 | 1.01 | 99.0 |

Significant degradation of Compound 1 is noted in samples dissolved in (non-purified) tap water after storage at room temperature for 6 days, as seen by loss in purity and assay. This is not observed for the samples dissolved in (purified) HPLC grade water (Fisher Scientific). Similar data was seen for two independent samples of different batches of Compound 1.

Example 12

HP-Cyclodextrin Formulation of Compound 1

Excipient Preparation

Kleptose hydroxypropyl β-Cyclodextrin (25% w/v), sodium dihydrogen phosphate anhydrous (0.048% w/v), disodium hydrogen phosphate dihydrate (0.295% w/v) and calcium disodium EDTA (0.5% w/v) were added to 100 mL deionised water. The mixture was sonicated for 20 mins then stirred until all the solid had dissolved then adjusted to pH 7.4 with HCl (1 M).

Formulation Protocol

1. Weigh out the required amount of Compound 1 then add the required amount of prepared excipient to the solid Compound 1 to give the required mg/ml concentration of Compound 1 (maximum tested 25 mg/ml). For example, for a 20 mg/ml formulation of Compound 1, weigh out 20 mg of Compound 1 and add 1 ml of the prepared excipient.
2. Sonicate the solution for 10 mins and then shake for 20 mins to ensure that Compound 1 is fully dissolved.
3. The solution can be centrifuged (13000 rpm, 10 mins) to remove any particulates if required.
4. The solution can be sterile filtered if required.

Example 13

Infusion of Compound 1 Delivers Succinate, Increases Succinate Metabolism in Pigs and Reduces Blood Lactate Concentrations Infusion of Compound 1 increases plasma succinate levels, increases metabolism of succinate to fumarate in tissues and decreases blood lactate concentrations. See FIG. 7.

Yorkshire landrace hybrid pigs were anaesthetised and implanted with venous catheters for infusions of Compound 1 or vehicle (PBS) and collection of blood samples.

Two animals received an escalating dose of Compound 1 (2-6 mg/kg/min) over a period of 2.5 hours, where the dose was increased by 1 mg/kg/min every 30 minutes.

One animal was infused at a constant rate of 2 mg/kg/min. The control animal was infused with PBS. Blood samples were taken with 30 min intervals and plasma was separated by centrifugation. Plasma and tissue samples were stored frozen and later analysed for succinate in an LC/MS method using a Thermo Vanquish UPLC+Thermo Quantis triple quadrupole MS instrument, an Acquity UPLC HSS C18 (100×2.1 mm, 1.8 µm) column with guard filter and gradient elution; A=0.1% Formic acid, B=Acetonitrile. [13C]-labelled succinate was used as internal standard.

Plasma succinate concentrations increased proportional to the time of Compound 1 infusion (FIG. 7A) demonstrating release of succinate from Compound 1. At the end of the study, fumarate, the primary metabolite of succinate in the TCA cycle was higher in tissues of the animal receiving Compound 1 than in the vehicle animal particularly in tissues with high metabolic activity such as retina, brain and heart. The data therefore suggest that Compound 1 delivers metabolizable succinate to these tissues and has the ability to pass the blood brain barrier.

Figure 7C:
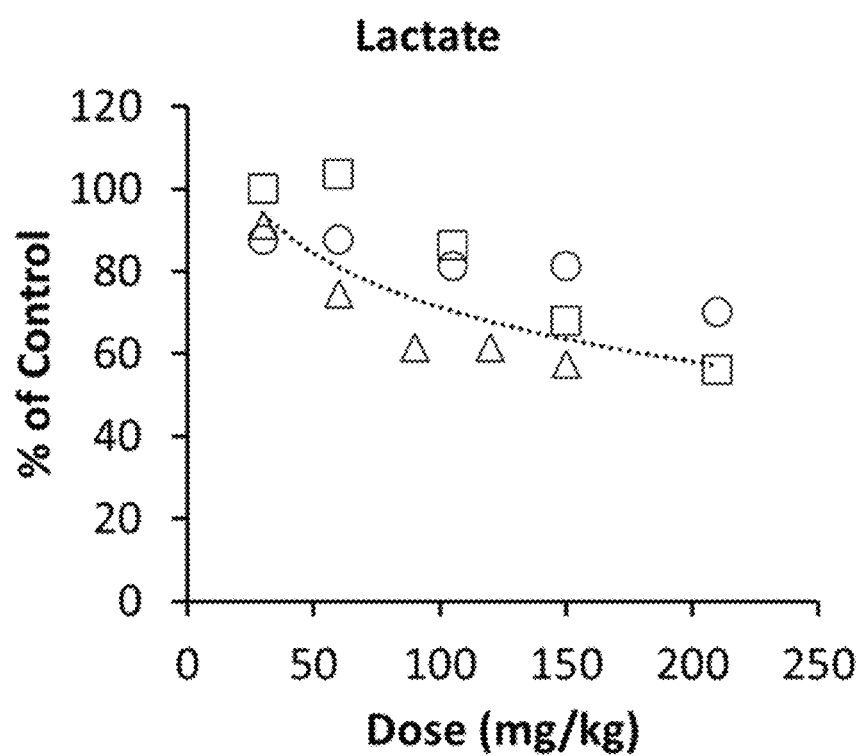
FIG. 7C. Intravenous infusion of PBS or Compound 1 in an anesthesised pig depicting effect on blood lactate concentrations.
Figure 8A:
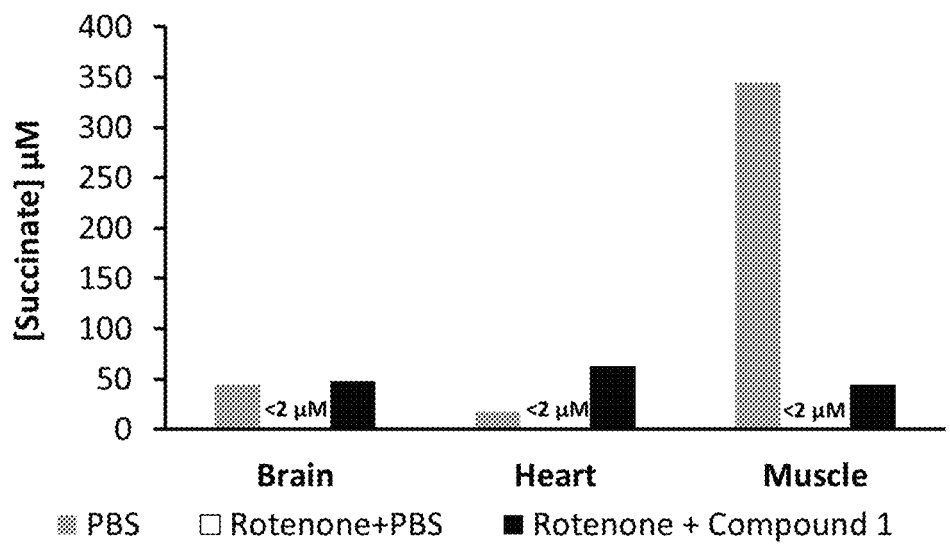
FIG. 8A-8B. Intravenous infusion of PBS or Compound 1 in an anesthesised pig simultaneously infused with the complex 1 inhibitor rotenone, depicting succinate concentrations in tissues at the end of infusion in (FIG. 8A), and lactate concentrations in brain microdialysates expressed as percent of the baseline value before initiation of infusion versus time in (FIG. 8B).
Figure 8B:
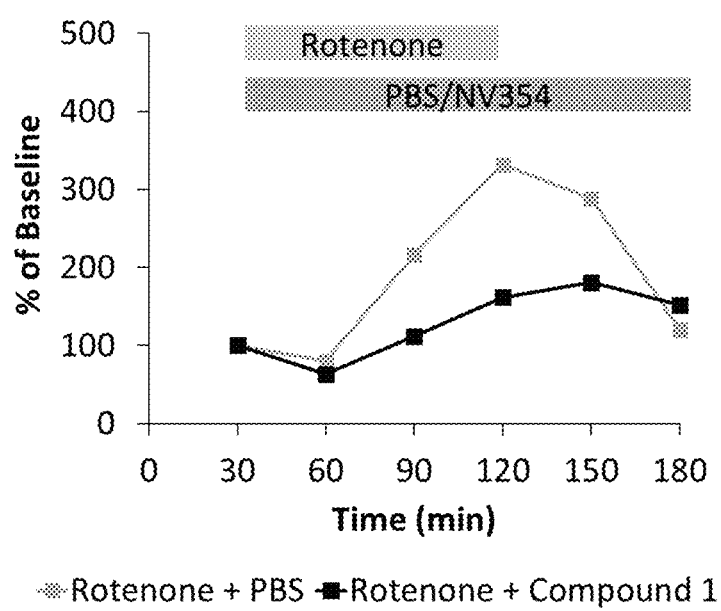

Blood lactate data combined from three animals were expressed as percentage of the initial value and plotted as a function of the cumulative dose at the time of sampling (FIG. 7C).

Lactate decreased relative to initial values after intravenous infusion of Compound 1 suggesting that Compound 1 delivers succinate to complex 2 and increases the supply of electrons to the mitochondrial electron transport chain to increase ATP production and decrease the need for glycolytic conversion of pyruvate to lactate.

Example 14

Pig Model of Rotenone Induced Mitochondrial Complex 1 Dysfunction

Infusion of Compound 1 restores rotenone depleted succinate levels in the organs and decreases rotenone induced lactate in the brain. See FIG. 8.

To study the effect of rotenone-mediated inhibition of complex 1, Yorkshire landrace hybrid pigs were anaesthetised and implanted with venous catheters for simultaneous infusion of rotenone and Compound 1 or vehicle (PBS). Rotenone (7.1 mg/hr) was infused during 1.5 hours. Compound 1 was infused at a constant rate of 2 mg/kg/min over a period of 2.5 hours. The control animal was infused with PBS. Blood samples were taken with 30 min intervals and plasma was separated by centrifugation. Microdialysates were collected by inserting a microdialysis probe into the striatum of the brain and analysed for lactate using an ISCUS instrument (MDialysis). At the end of infusion, the animal was euthanised and terminal blood and organ samples were collected.

Plasma and tissue samples were stored frozen and later analysed for succinate in an LC/MS method using a Thermo Vanquish UPLC+Thermo Quantis triple quadrupole MS instrument, an Acquity UPLC HSS C18 (100×2.1 mm, 1.8 μm) column with guard filter and gradient elution; A=0.1% Formic acid, B=Acetonitrile. [13C]-labelled succinate was used as internal standard. Lactate data were expressed as percentage of the baseline value obtained before start of rotenone infusion.

Rotenone infusion decrease tissue concentrations of succinate to a level below quantification (<2 μM) indicating an increased utilisation of succinate to compensate for the decrease in electron transfer from complex 1. Administration of Compound 1 restored tissue succinate concentrations to detectable levels suggesting that the delivery of succinate by Compound 1 exceeded the increased succinate utilisation caused by complex 1 inhibition. Furthermore, administration of Compound 1 counteracted a rotenone induced increase in brain lactate, confirming a decreased need for glycolytic conversion of pyruvate to lactate by delivery of succinate to the brain.

Example 15

Mouse Genetic Ndufs4 Knock-out Model of Complex 1 Dysfunction

Figure 9A:
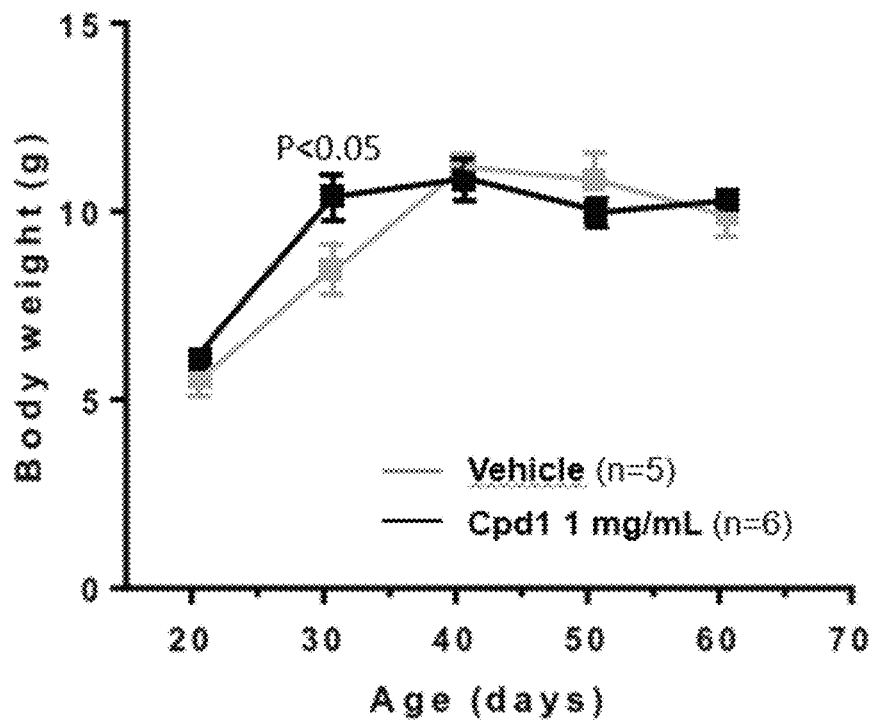
FIG. 9A-9B. Treatment of Ndufs4 KO mice with Compound 1 in the drinking water depicting body weight development versus time in (FIG. 9A) and percent survival versus time in (FIG. 9B).

Administration of Compound 1 in the drinking water (1 mg/mL) from weaning (day 21) results in transiently increased body weight and a trend of prolonged survival in the high concentration group. See FIG. 9.

Figure 9B:
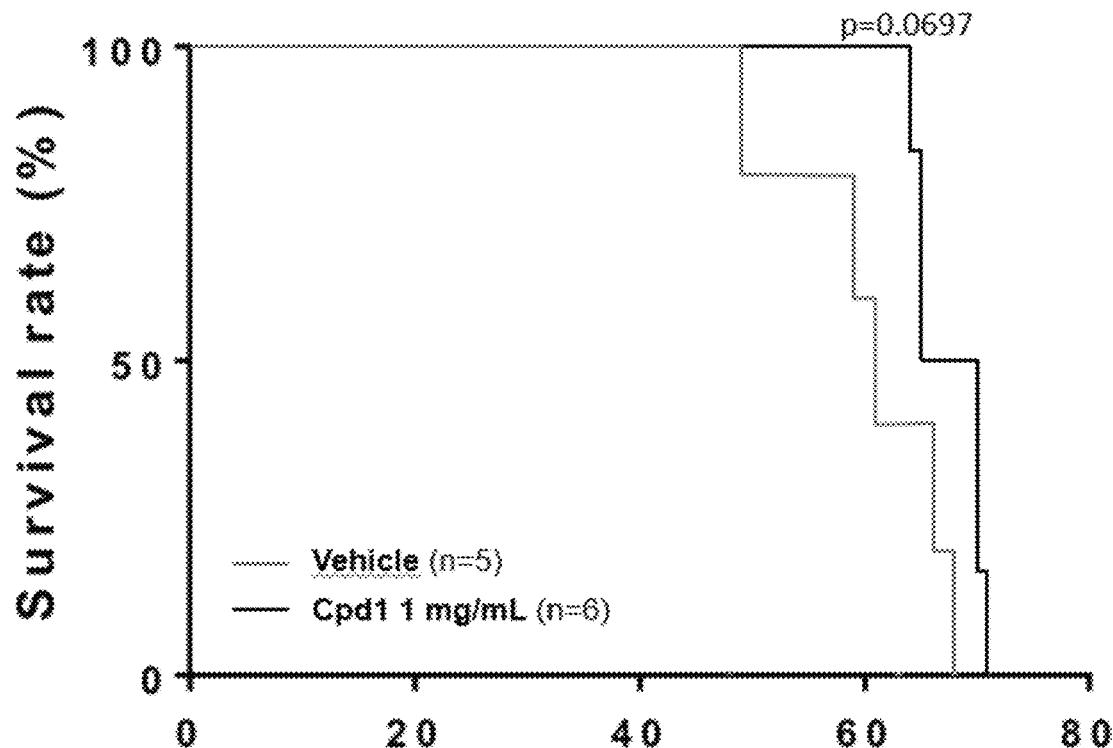

C57BL/6 mice with a genetic ablation of the complex I gene Ndufs4 (Quintana et al., Proceedings of the National Academy of Sciences. 107, 24 (2010), 10996-11001) were given Compound 1 (1 mg/mL) in the drinking water or plain drinking water from weaning. Body weight development was monitored every 10 days (FIG. 9A) and animal health was monitored daily (FIG. 9B). Compound 1 increased weigh gain (p<0.05) during the first 10 days and increased the survival rate (p=0.0697). The results suggest that a therapeutic benefit of succinate supplementation in the form of Compound 1 can be achieved in a genetic model of mitochondrial complex I dysfunction I with features of Leigh syndrome.

Example 16

Rat Model of Rotenone Induced Motor Dysfunction and Lactic Acidosis

Figure 10A:
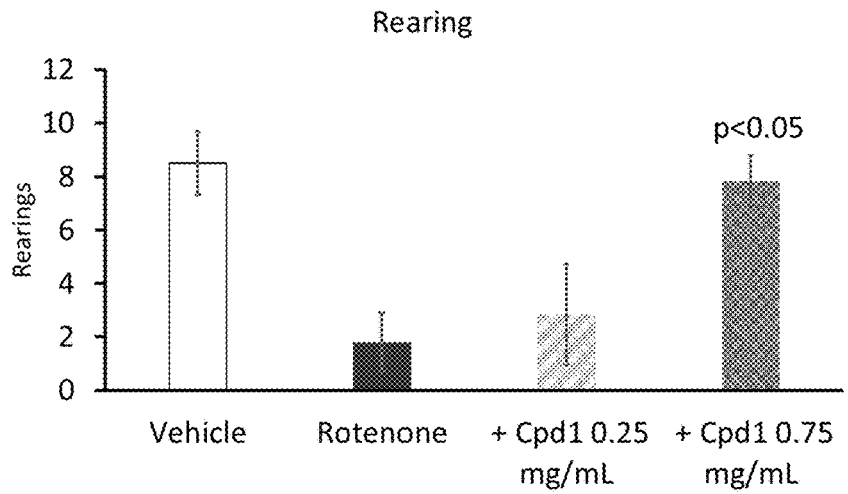
FIG. 10A-10C. Treatment of rotenone injected rats with Compound 1 in the drinking water depicting number of rearings versus treatment in (FIG. 10A), displacement distance in a postural instability test versus treatment in (FIG. 10B) and blood lactate concentration versus treatment in (FIG. 10C).
Figure 10B:
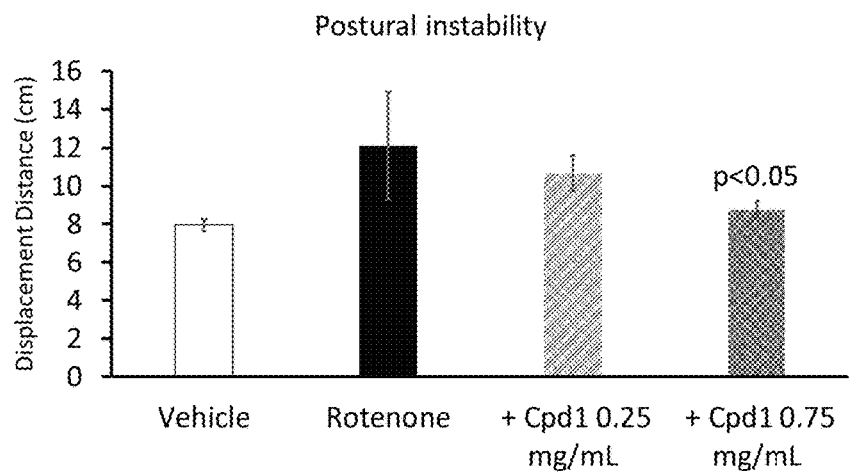
Figure 10C:
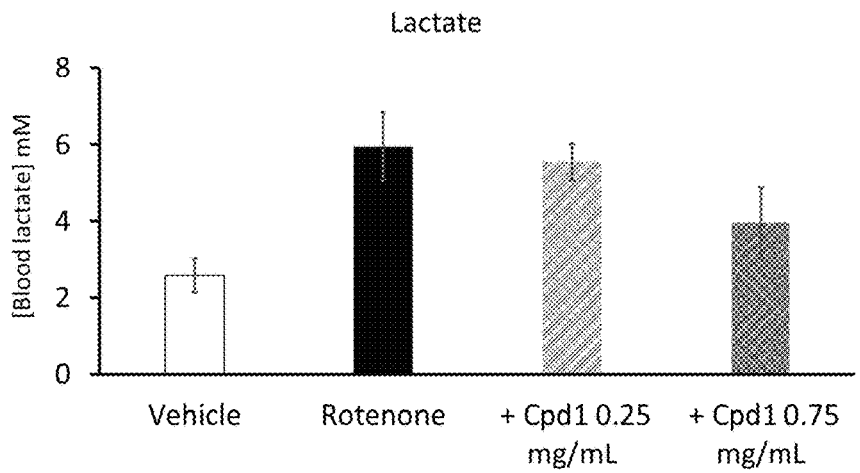

Compound 1 administered in the drinking water prevents motor dysfunctions and reduces blood lactate concentrations. See FIG. 10.

A rotenone induced rat Parkinson disease model (Cannon et al., Neurobiol Dis. 2009 May; 34(2):279-90) was used to study the effect of oral administration of Compound 1 on motoric and metabolic dysfunctions caused by complex 1 inhibition.

Twelve-week old Lewis rats (6 animals per group) received daily intraperitoneal injections of rotenone (0.25-0.75 mg/kg) for 4 days. Compound 1 was dissolved in the drinking water at a concentration of 0.25 and 0.75 mg/mL. Functional tests and lactate measurements were performed day 4. Rearing was measured by placing animals in a clear glass cylinder (height=30 cm; diameter=18 cm) during five minutes. To be classified as rearing, the forelimbs should be raised above shoulder level and make contact with the cylinder wall with either one or both forelimbs.

Postural instability was measured on a table-top covered with P-120 sandpaper, marked with lines and numbers every centimetre (see below). The animal was held in a vertical position ("wheelbarrow"-like position), at a nearly 90° angle to the surface with one forelimb gently restrained against the animal's torso. The centre of gravity of the animal was then shifted forward over the single planted forelimb to trigger two "catch-up" steps, to regain its balance. The change in position of the nose was recorded as the distance that triggered a catch-up step in the unrestrained forelimb. The experiment was repeated three times for each forelimb and an average of for both forelimbs was calculated. Blood lactate (FIG. 10C) was measured in a VetScan iSTAT-1 Analyser.

Rotenone treatment resulted in decrease rearing activity. Administration of Compound 1 (0.75 mg/mL) in the drinking water resulted in a significant increase in rearings (FIG. 10A) and postural instability (FIG. 10B) compared to treated animals receiving water. The data therefore suggest that Compound 1 is orally bioavailable and is able to ameliorate motoric dysfunctions caused by mitochondrial complex 1 dysfunction.

Blood lactate concentrations were increased significantly in animals treated with rotenone. There was a trend of decreasing lactate concentrations in blood from the low concentration (0.25 mg/mL) of Compound 1 in the drinking water to the high concentration (0.75 mg/mL). The data suggest that succinate delivered from Compound 1 can achieve metabolic compensation at the level of glycolysis and conversion of pyruvate to lactate when delivered via the oral route by intermittent administration in the drinking water and implicates suitability as an oral treatment.

Example 17

Succinate Release Data

In brief, a stock of Compound 1 Batch 12 was prepared in 50/50 DMSO/MeCN (200 mM, ×200). This mixture was then diluted 1 in 10 into microsome buffer (20 mM, ×20) consisting of $K_2HPO_4$ (Sigma Aldrich, 13.9 g/L, anhydrous), $KH_2PO_4$ (Sigma Aldrich, 2.72 g/L, anhydrous), $MgCl_2.6H_2O$ (Fisher, 1.02 g/L) and EDTA (Sigma Aldrich, 0.375 g/L) dissolved in HPLC grade water. A 200 mM malonic acid (Sigma Aldrich) stock was then prepared in microsome buffer (200 mM, ×20). A 20 mM NADPH stock was also prepared in microsome buffer (20 mM, ×10). A stock of microsomes (Sekisui XenoTech, 0.625 mg/ml) was prepared in a 7 ml vial. Samples were prepared for each timepoint (T=0, 5, 15, 60 mins) as follows: 80 µL microsome stock (0.5 mg/mL final concentration), 5 µL of Compound stock (2 mM final concentration), 5 µL of malonate stock (10 mM final concentration). The T=0 sample was quenched by adding 100 µL MeOH. Reaction of all timepoints was then initiated with addition of 10 µL NADPH stock (2 mM final concentration). At each timepoint, the reaction was terminated by the addition of 100 µL MeOH. Samples were shaken for 1 min, placed on ice for 10 min, then centrifuged at 3000 rpm for 10 minutes. The supernatant was then analysed by LCMS.

TABLE 25

| | Species detected by LCMS | | |
|---|---|---|---|
| Time (min) | Compound 1 (mM) | Succinic acid (mM) | Mono-methyl succinate (mM) |
| 0 | 0.934 | 0.058 | 0.088 |
| 5 | 0.688 | 0.136 | 0.161 |
| 15 | 0.388 | 0.285 | 0.205 |
| 60 | 0.080 | 0.599 | 0.308 |

As can be seen from the data, Compound 1 releases succinic acid over time when incubated with microsomes.

Example 18

Mineral Instability

Compound 1 Batch 14 (2-3 mg) was dissolved in water for injection at room temperature (WFI) (1 mg/ml) containing different sources of minerals commonly found in tap water (with different accompanying counter ions to be able to distinguish differences between the effects of cation or anion) and samples were taken at different time intervals for HPLC analysis.

Mineral sources used in the form of inorganic salts:
$CuCl_2$, $CaCl_2$, $NiSO_4$, $CoCl_2$, $NH_4Cl$, $MnCl_2$, $NaF$, $NaNO_3$, $CuSO_4$, $Ca(NO_3)_2$, $AlSO_4$, $CaCO_3$, $(NH_4)_2CO_3$.

TABLE 26

| Time | Percentage (%) of Compound 1 remaining when compared to the T = 0 timepoint for each different salt added to HPLC water | | | | | | |
|---|---|---|---|---|---|---|---|
| (days) | WFI | $CuCl_2$ | $CaCl_2$ | $NiSO_4$ | $CoCl_2$ | $NH_4Cl$ | $MnCl_2$ |
| 0 | 100 | 100 | 100 | 100 | 100 | 100 | 100 |
| 7 | 98.7 | 99.5 | 100 | 98.4 | 101 | 101 | 98.9 |
| 14 | 97.7 | 98.3 | 97.9 | 99.1 | 101 | 99.8 | 99.2 |

| Time | Percentage (%) of Compound 1 remaining when compared to the T = 0 timepoint for each different salt added to HPLC water | | | | | | |
|---|---|---|---|---|---|---|---|
| (days) | NaF | $NaNO_3$ | $CuSO_4$ | $Ca(NO_3)_2$ | $AlSO_4$ | $CaCO_3$ | $(NH_4)_2CO_3$ |
| 0 | 100 | 100 | 100 | 100 | 100 | 100 | 100 |
| 7 | 101 | 99.2 | 100 | 99.4 | 99.8 | 79.5 | 91.3 |
| 14 | 100 | 99.4 | 99.4 | 98.9 | 100 | 66.0 | 87.4 |

As can be seen from the data, Compound 1 degrades more rapidly when in aqueous solution with carbonate ions.

Example 19

Carbonate Instability

Compound 1 Batch 14 (2-3 mg) was dissolved in HPLC grade water at room temperature (1 mg/ml) containing different sources of calcium and carbonate ions (two concentrations for each source, with the pH recorded) and samples were taken at different time intervals for HPLC analysis.

Calcium and carbonate sources used in the form of inorganic salts:
$CaCl_2 \cdot Ca(NO_3)_2 \cdot CaCO_3 \cdot (NH_2CO_3$

TABLE 27

| | Percentage (%) of Compound 1 remaining when compared to the T = 0 timepoint for each different mineral added to HPLC water | | | | |
|---|---|---|---|---|---|
| Time (days) | HPLC water (control, pH 6.5) | $CaCO_3$ (3.4 mM, pH 7.6) | $CaCO_3$ (0.34 mM, pH 7.6) | $CaCl_2$ (3.4 mM, pH 7.5) | $CaCl_2$ (0.34 mM, pH 7.4) |
| 0 | 100 | 100 | 100 | 100 | 100 |
| 3 | 94.3 | 93.6 | 93.8 | 101 | 98.4 |
| 17 | 91.4 | 49.5 | 50.4 | 96.7 | 95.1 |

TABLE 27-continued

Percentage (%) of Compound 1 remaining when compared to the T = 0 timepoint for each different mineral added to HPLC water

| Time (days) | Ca(NO$_3$)$_2$ (3.4 mM, pH 7.2) | Ca(NO$_3$)$_2$ (0.34 mM, pH 7.3) | (NH$_4$)$_2$CO$_3$ (3.4 mM, pH 9.3) | (NH$_4$)$_2$CO$_3$ (3.4 mM, pH 8.9) |
|---|---|---|---|---|
| 0 | 100 | 100 | 100 | 100 |
| 3 | 100 | 101 | 98.9 | 99.6 |
| 17 | 97.1 | 97.5 | 57.5 | 85.5 |

As can be seen from the data, Compound 1 degrades more rapidly when in aqueous solution with carbonate ions.

Example 19

Carbonate Concentration Dependence

Compound 1 Batch 14 (2-3 mg) was dissolved in HPLC grade water (1 mg/ml) containing different concentrations of calcium carbonate and samples were taken at different time intervals for HPLC analysis.

TABLE 28

Percentage (%) of Compound 1 remaining when compared to the T = 0 timepoint for each different mineral added to HPLC water

| Time (days) | CaCO$_3$ (0 mM) | CaCO$_3$ (0.425 mM) | CaCO$_3$ (0.85 mM) | CaCO$_3$ (1.7 mM) | CaCO$_3$ (3.4 mM) |
|---|---|---|---|---|---|
| 0 | 100 | 100 | 100 | 100 | 100 |
| 7 | 98.7 | 98.1 | 97.8 | 93.8 | 83.4 |
| 14 | 98.6 | 98.4 | 97.1 | 90.8 | 71.4 |

Example 20

Kinetic Solubility

Solid Compound 1 Batches s3, s12-17 (~80 mg) were added to wells of a flat clear bottom 96 well plate. PBS at 5° C. was added to give a 460 mg/ml final concentration of 01-354 for all batches. After addition of the PBS, the plate was agitated for 10 s then immediately analysed for turbidity at 620 nm in real time for 3 mins by an Epoch Microplate Spectrophotometer (BioTek). A rate constant for the dissolution was calculated from the exponential decay fit of the recorded data.

TABLE 29

| Compound 1 Batch No. | Rate constants, k (s$^{-1}$) |
|---|---|
| 3 | 0.014 |
| 12 | 0.022 |
| 13 | 0.013 |
| 14 | 0.011 |
| 15 | 0.074 |
| 16 | 0.055 |
| 17 | 0.111 |

General Method for Assessing Crystallinity

X-ray powder diffractions studies were conducted using a Bruker AXS D8 discover HTS.

Anode: Cu anode at 40 kV and 4 mV; Göbel mirror and line optics.

Detector: linear detector (LYNXEYE XE) with receiver slit of 2.95°.

Measurement: scan range 2-45° 2θ, 1 s/step, 0.005°/step

Data collection software: Diffrac.Commander v7.3.3.0.0

Data analysis software: Diffrac Eva v4.2.1

No background correction or smoothing was applied. Data are reported as peak 2θ angle and intensity. In order to determine the extent of crystallinity the combined area for all defined peaks was divided by the total area under curve and expressed as a percentage.

Peak List

The following list details the peaks returned after XRPD on a number of crystal-line batches. Peaks underlined are common to most batches. Those where there is an asterisk next to the angle may be peaks more common or unique to polymorphic forms.

Peak list NV354-s3 - batch 3

| Angle | d Value | Intensity | Rel. Intensity |
|---|---|---|---|
| 9.4 | 9.389 | 54 | 1.4% |
| <u>10.9</u> | <u>8.136</u> | <u>453</u> | <u>12.1%</u> |
| <u>11.1*</u> | <u>7.997</u> | <u>1270</u> | <u>33.7%</u> |
| 11.4 | 7.777 | 110 | 2.9% |
| 12.9 | 6.870 | 208 | 5.5% |
| 13.1 | 6.776 | 1240 | 32.9% |
| <u>13.1</u> | <u>6.728</u> | <u>120</u> | <u>3.2%</u> |
| <u>13.8</u> | <u>6.420</u> | <u>36</u> | <u>1.0%</u> |
| 14.5 | 6.104 | 60 | 1.6% |
| 14.9 | 5.939 | 406 | 10.8% |
| 15.6 | 5.659 | 63 | 1.7% |
| <u>16.2</u> | <u>5.476</u> | <u>179</u> | <u>4.8%</u> |
| <u>16.9*</u> | <u>5.246</u> | <u>89</u> | <u>2.4%</u> |
| 17.9 | 4.941 | 89 | 2.4% |
| 18.5 | 4.785 | 49 | 1.3% |
| 19.2 | 4.624 | 176 | 4.7% |
| 19.6 | 4.528 | 226 | 6.0% |
| 19.7 | 4.499 | 214 | 5.7% |
| 20.1 | 4.418 | 111 | 3.0% |
| <u>21.4</u> | <u>4.143</u> | <u>831</u> | <u>22.1%</u> |
| <u>21.7</u> | <u>4.100</u> | <u>95</u> | <u>2.5%</u> |
| 22.2 | 3.994 | 163 | 4.3% |
| 22.7 | 3.919 | 698 | 18.6% |
| 22.8 | 3.893 | 1410 | 37.4% |
| <u>23.1</u> | <u>3.847</u> | <u>2760</u> | <u>73.4%</u> |
| <u>23.3</u> | <u>3.813</u> | <u>307</u> | <u>8.2%</u> |
| <u>24.0</u> | <u>3.711</u> | <u>3760</u> | <u>100.0%</u> |
| 24.4 | 3.640 | 58 | 1.5% |
| 24.8 | 3.591 | 602 | 16.0% |
| <u>25.2</u> | <u>3.538</u> | <u>78</u> | <u>2.1%</u> |
| 25.5 | 3.487 | 283 | 7.5% |
| <u>26.1</u> | <u>3.409</u> | <u>1340</u> | <u>35.5%</u> |
| <u>27.2</u> | <u>3.282</u> | <u>53</u> | <u>1.4%</u> |
| 27.7 | 3.221 | 76 | 2.0% |
| 28.0 | 3.185 | 58 | 1.5% |
| 28.5 | 3.128 | 48 | 1.3% |
| 29.9 | 2.989 | 69 | 1.8% |
| 30.2 | 2.956 | 115 | 3.1% |
| 30.8 | 2.901 | 89 | 2.4% |
| 30.9 | 2.890 | 73 | 1.9% |
| 31.3 | 2.857 | 64 | 1.7% |
| 31.6 | 2.829 | 29 | 0.8% |
| 32.2 | 2.776 | 42 | 1.1% |
| 32.8 | 2.730 | 27 | 0.7% |
| 33.0 | 2.711 | 42 | 1.1% |
| 33.2 | 2.694 | 59 | 1.6% |
| 35.0 | 2.560 | 73 | 1.9% |
| 35.4 | 2.536 | 37 | 1.0% |
| 36.6 | 2.456 | 86 | 2.3% |
| 38.6 | 2.333 | 49 | 1.3% |
| 40.1 | 2.248 | 52 | 1.4% |
| 41.6 | 2.169 | 58 | 1.5% |
| 44.7 | 2.026 | 86 | 2.3% |
| 44.8 | 2.022 | 57 | 1.5% |

Peak list NV354-s12 - batch 18

| Angle | d Value | Intensity | Rel. Intensity |
|---|---|---|---|
| 5.6 | 15.805 | 68 | 3.3% |
| 9.4 | 9.390 | 99 | 4.9% |
| 10.9 | 8.141 | 233 | 11.5% |
| 11.1 | 7.949 | 365 | 18.0% |
| 11.2 | 7.883 | 635 | 31.3% |
| 11.4 | 7.744 | 252 | 12.4% |
| 12.9 | 6.848 | 183 | 9.0% |
| 13.2 | 6.710 | 103 | 5.1% |
| 13.8 | 6.432 | 115 | 5.7% |
| 14.9 | 5.941 | 446 | 22.0% |
| 15.7 | 5.657 | 91 | 4.5% |
| 16.2 | 5.484 | 312 | 15.4% |
| 16.9 | 5.243 | 288 | 14.2% |
| 17.3 | 5.119 | 107 | 5.3% |
| 18.1 | 4.902 | 87 | 4.3% |
| 18.6 | 4.779 | 60 | 3.0% |
| 19.3 | 4.607 | 274 | 13.5% |
| 19.3 | 4.594 | 154 | 7.6% |
| 19.7 | 4.506 | 164 | 8.1% |
| 20.1 | 4.411 | 505 | 25.0% |
| 21.4 | 4.148 | 1030 | 51.1% |
| 21.6 | 4.110 | 160 | 7.9% |
| 22.2 | 4.001 | 395 | 19.5% |
| 22.7 | 3.919 | 2030 | 100.0% |
| 22.8 | 3.892 | 1960 | 96.6% |
| 23.0 | 3.865 | 1990 | 98.3% |
| 23.2 | 3.824 | 204 | 10.1% |
| 24.0 | 3.709 | 90 | 4.5% |
| 24.5 | 3.637 | 122 | 6.0% |
| 24.8 | 3.593 | 226 | 11.1% |
| 25.1 | 3.539 | 227 | 11.2% |
| 25.5 | 3.487 | 126 | 6.2% |
| 26.1 | 3.407 | 151 | 7.4% |
| 27.8 | 3.210 | 196 | 9.7% |
| 28.5 | 3.124 | 53 | 2.6% |
| 32.8 | 2.728 | 41 | 2.0% |
| 35.0 | 2.560 | 64 | 3.2% |
| 37.7 | 2.386 | 75 | 3.7% |
| 41.6 | 2.169 | 62 | 3.0% |
| 43.0 | 2.104 | 26 | 1.3% |

Peak list NV354-s13 - batch 13

| Angle | d Value | Intensity | Rel. Intensity |
|---|---|---|---|
| 7.9 | 11.190 | 39 | 2.3% |
| 9.4 | 9.405 | 118 | 6.9% |
| 10.9 | 8.136 | 668 | 39.3% |
| 11.1 | 7.963 | 408 | 24.0% |
| 11.2 | 7.884 | 294 | 17.3% |
| 11.4 | 7.743 | 179 | 10.5% |
| 12.9 | 6.858 | 209 | 12.3% |
| 13.2 | 6.709 | 103 | 6.1% |
| 13.8 | 6.432 | 26 | 1.6% |
| 14.5 | 6.099 | 71 | 4.2% |
| 14.9 | 5.954 | 474 | 27.9% |
| 15.6 | 5.659 | 155 | 9.1% |
| 16.2 | 5.472 | 326 | 19.2% |
| 16.9 | 5.250 | 134 | 7.9% |
| 17.4 | 5.102 | 44 | 2.6% |
| 18.1 | 4.906 | 89 | 5.2% |
| 19.0 | 4.677 | 57 | 3.3% |
| 19.2 | 4.619 | 269 | 15.8% |
| 19.4 | 4.577 | 180 | 10.6% |
| 19.7 | 4.505 | 162 | 9.5% |
| 20.1 | 4.414 | 392 | 23.0% |
| 21.4 | 4.145 | 536 | 31.5% |
| 21.6 | 4.106 | 79 | 4.7% |
| 22.3 | 3.990 | 396 | 23.3% |
| 22.7 | 3.913 | 898 | 52.7% |
| 22.9 | 3.887 | 1700 | 100.0% |
| 23.1 | 3.855 | 1380 | 80.9% |
| 23.3 | 3.812 | 336 | 19.9% |
| 24.0 | 3.711 | 84 | 4.9% |
| 24.6 | 3.620 | 131 | 7.7% |
| 24.8 | 3.590 | 371 | 21.8% |
| 25.2 | 3.536 | 152 | 8.9% |
| 25.5 | 3.487 | 94 | 5.5% |
| 26.1 | 3.407 | 195 | 11.4% |
| 27.2 | 3.280 | 71 | 4.2% |
| 27.8 | 3.210 | 100 | 5.9% |
| 28.0 | 3.185 | 90 | 5.3% |
| 29.6 | 3.015 | 47 | 2.8% |
| 30.2 | 2.959 | 34 | 2.0% |
| 30.8 | 2.902 | 72 | 4.2% |
| 31.3 | 2.858 | 37 | 2.2% |
| 31.6 | 2.827 | 27 | 1.6% |
| 32.0 | 2.795 | 68 | 4.0% |
| 32.8 | 2.730 | 79 | 4.6% |
| 34.2 | 2.620 | 65 | 3.8% |
| 34.4 | 2.602 | 52 | 3.0% |
| 35.1 | 2.555 | 63 | 3.7% |
| 35.4 | 2.535 | 66 | 3.9% |
| 37.7 | 2.384 | 44 | 2.6% |
| 40.1 | 2.246 | 35 | 2.1% |
| 41.6 | 2.170 | 68 | 4.0% |
| 44.2 | 2.049 | 27 | 1.6% |

Peak list NV354-s14 - batch 14

| Angle | d Value | Intensity | Rel. Intensity |
|---|---|---|---|
| 7.9 | 11.145 | 111 | 5.5% |
| 9.4 | 9.370 | 132 | 6.5% |
| 10.8 | 8.175 | 130 | 6.4% |
| 10.9 | 8.132 | 74 | 3.7% |
| 11.1 | 7.992 | 343 | 16.9% |
| 11.4 | 7.750 | 184 | 9.0% |
| 12.9 | 6.841 | 73 | 3.6% |
| 13.2 | 6.713 | 169 | 8.3% |
| 14.9 | 5.935 | 113 | 5.6% |
| 15.6 | 5.663 | 80 | 3.9% |
| 16.2 | 5.484 | 161 | 7.9% |
| 16.9 | 5.248 | 47 | 2.3% |
| 18.0 | 4.937 | 33 | 1.6% |
| 18.6 | 4.777 | 52 | 2.6% |
| 19.4 | 4.564 | 220 | 10.9% |
| 19.7 | 4.502 | 195 | 9.6% |
| 20.1 | 4.421 | 46 | 2.3% |
| 21.4 | 4.143 | 1150 | 56.5% |
| 22.2 | 4.000 | 355 | 17.5% |
| 22.7 | 3.921 | 2030 | 100.0% |
| 22.9 | 3.888 | 509 | 25.1% |
| 23.0 | 3.857 | 812 | 40.0% |
| 24.5 | 3.624 | 173 | 8.5% |
| 24.8 | 3.592 | 40 | 2.0% |
| 25.2 | 3.537 | 89 | 4.4% |
| 25.5 | 3.486 | 346 | 17.0% |
| 26.0 | 3.427 | 122 | 6.0% |
| 26.2 | 3.397 | 169 | 8.3% |
| 27.1 | 3.282 | 63 | 3.1% |
| 27.8 | 3.208 | 262 | 12.9% |
| 28.0 | 3.182 | 57 | 2.8% |
| 28.6 | 3.123 | 43 | 2.1% |
| 28.7 | 3.113 | 52 | 2.6% |
| 29.6 | 3.012 | 30 | 1.5% |
| 30.3 | 2.951 | 82 | 4.0% |
| 30.8 | 2.901 | 55 | 2.7% |
| 31.2 | 2.864 | 31 | 1.5% |
| 32.2 | 2.775 | 22 | 1.1% |
| 33.0 | 2.711 | 55 | 2.7% |

Peak list NV354-s14 - batch 14

| Angle | d Value | Intensity | Rel. Intensity |
|---|---|---|---|
| 34.2 | 2.618 | 83 | 4.1% |
| 34.8 | 2.577 | 44 | 2.2% |
| 35.1 | 2.556 | 57 | 2.8% |
| 36.2 | 2.483 | 167 | 8.2% |
| 37.3 | 2.408 | 69 | 3.4% |
| 37.7 | 2.386 | 44 | 2.2% |
| 39.8 | 2.266 | 26 | 1.3% |
| 41.6 | 2.169 | 83 | 4.1% |
| 41.7 | 2.164 | 45 | 2.2% |

Peak list NV354-s15 - batch 19

| Angle | d Value | Intensity | Rel. Intensity |
|---|---|---|---|
| 5.6 | 15.862 | 72 | 4.6% |
| 7.9 | 11.170 | 52 | 3.3% |
| 9.4 | 9.389 | 134 | 8.5% |
| 10.8 | 8.151 | 388 | 24.6% |
| 11.1 | 7.976 | 412 | 26.2% |
| 11.2 | 7.907 | 400 | 25.4% |
| 11.4 | 7.765 | 121 | 7.7% |
| 12.9 | 6.846 | 108 | 6.8% |
| 13.2 | 6.714 | 211 | 13.4% |
| 13.7 | 6.440 | 41 | 2.6% |
| 14.9 | 5.936 | 456 | 29.0% |
| 15.6 | 5.660 | 134 | 8.5% |
| 16.2 | 5.478 | 312 | 19.8% |
| 16.9 | 5.252 | 122 | 7.7% |
| 18.1 | 4.906 | 49 | 3.1% |
| 19.0 | 4.673 | 58 | 3.7% |
| 19.2 | 4.614 | 96 | 6.1% |
| 19.7 | 4.506 | 170 | 10.8% |
| 20.1 | 4.413 | 162 | 10.3% |
| 21.4 | 4.143 | 943 | 59.9% |
| 21.6 | 4.104 | 306 | 19.5% |
| 22.2 | 3.997 | 318 | 20.2% |
| 22.8 | 3.894 | 1400 | 88.7% |
| 23.1 | 3.854 | 1570 | 100.0% |
| 23.3 | 3.813 | 488 | 31.0% |
| 23.9 | 3.716 | 81 | 5.1% |
| 24.5 | 3.628 | 74 | 4.7% |
| 24.5 | 3.627 | 109 | 6.9% |
| 24.8 | 3.592 | 139 | 8.8% |
| 25.2 | 3.535 | 147 | 9.3% |
| 25.6 | 3.482 | 146 | 9.3% |
| 26.1 | 3.406 | 139 | 8.8% |
| 27.2 | 3.281 | 52 | 3.3% |
| 27.8 | 3.211 | 122 | 7.8% |
| 29.6 | 3.012 | 34 | 2.2% |
| 30.8 | 2.900 | 62 | 3.9% |
| 33.0 | 2.715 | 25 | 1.6% |
| 41.6 | 2.170 | 38 | 2.4% |

Peak list NV354-s16 - batch 16

| Angle | d Value | Intensity | Rel. Intensity |
|---|---|---|---|
| 5.6 | 15.858 | 91 | 4.2% |
| 7.9 | 11.148 | 63 | 2.9% |
| 9.4 | 9.395 | 138 | 6.3% |
| 10.9 | 8.134 | 401 | 18.4% |
| 11.1 | 7.945 | 354 | 16.3% |
| 11.2 | 7.891 | 514 | 23.6% |
| 11.4 | 7.748 | 167 | 7.7% |
| 12.9 | 6.852 | 100 | 4.6% |
| 13.2 | 6.709 | 175 | 8.0% |
| 13.8 | 6.424 | 72 | 3.3% |
| 14.5 | 6.091 | 54 | 2.5% |
| 14.9 | 5.943 | 370 | 17.0% |
| 15.7 | 5.656 | 151 | 7.0% |
| 16.2 | 5.479 | 233 | 10.7% |
| 16.9 | 5.244 | 248 | 11.4% |
| 17.4 | 5.106 | 31 | 1.4% |
| 18.1 | 4.895 | 106 | 4.9% |
| 18.6 | 4.777 | 43 | 2.0% |
| 19.2 | 4.613 | 284 | 13.1% |
| 19.4 | 4.583 | 214 | 9.8% |
| 19.7 | 4.507 | 179 | 8.2% |
| 20.1 | 4.413 | 274 | 12.6% |
| 21.4 | 4.147 | 622 | 28.6% |
| 21.6 | 4.102 | 210 | 9.7% |
| 22.2 | 3.995 | 293 | 13.5% |
| 22.7 | 3.921 | 834 | 38.3% |
| 22.8 | 3.891 | 1490 | 68.2% |
| 23.1 | 3.855 | 2180 | 100.0% |
| 23.3 | 3.813 | 279 | 12.8% |
| 24.0 | 3.711 | 87 | 4.0% |
| 24.5 | 3.627 | 100 | 4.6% |
| 24.8 | 3.592 | 266 | 12.2% |
| 25.2 | 3.533 | 180 | 8.3% |
| 25.5 | 3.489 | 122 | 5.6% |
| 26.2 | 3.403 | 162 | 7.4% |
| 27.1 | 3.283 | 36 | 1.6% |
| 27.8 | 3.207 | 173 | 7.9% |
| 28.0 | 3.184 | 49 | 2.2% |
| 28.5 | 3.125 | 34 | 1.6% |
| 29.6 | 3.015 | 33 | 1.5% |
| 30.8 | 2.905 | 82 | 3.8% |
| 31.6 | 2.829 | 44 | 2.0% |
| 32.0 | 2.791 | 24 | 1.1% |
| 32.8 | 2.725 | 42 | 1.9% |
| 34.2 | 2.618 | 71 | 3.3% |
| 35.0 | 2.559 | 61 | 2.8% |
| 35.4 | 2.537 | 28 | 1.3% |
| 36.1 | 2.484 | 35 | 1.6% |
| 37.7 | 2.387 | 48 | 2.2% |
| 40.2 | 2.244 | 47 | 2.2% |
| 41.6 | 2.170 | 98 | 4.5% |

Peak list NV354-s17 - batch 17

| Angle | d Value | Intensity | Rel. Intensity |
|---|---|---|---|
| 7.9 | 11.171 | 108 | 2.6% |
| 9.4 | 9.422 | 77 | 1.8% |
| 10.8 | 8.158 | 297 | 7.1% |
| 11.1 | 7.984 | 379 | 9.0% |
| 11.2 | 7.873 | 790 | 18.9% |
| 11.4 | 7.753 | 134 | 3.2% |
| 12.8 | 6.892 | 114 | 2.7% |
| 12.9 | 6.845 | 185 | 4.4% |
| 13.2 | 6.715 | 179 | 4.3% |
| 13.8 | 6.420 | 77 | 1.8% |
| 14.9 | 5.931 | 349 | 8.3% |
| 15.7 | 5.649 | 225 | 5.4% |
| 16.2 | 5.462 | 184 | 4.4% |
| 16.9 | 5.248 | 303 | 7.2% |
| 17.9 | 4.948 | 52 | 1.3% |
| 18.5 | 4.785 | 40 | 0.9% |
| 19.2 | 4.625 | 183 | 4.4% |
| 19.3 | 4.586 | 263 | 6.3% |
| 19.7 | 4.500 | 307 | 7.3% |
| 20.1 | 4.416 | 220 | 5.3% |
| 21.4 | 4.148 | 501 | 12.0% |
| 21.6 | 4.105 | 145 | 3.5% |
| 22.2 | 3.998 | 1100 | 26.3% |

-continued

| Peak list NV354-s17 - batch 17 | | | |
|---|---|---|---|
| Angle | d Value | Intensity | Rel. Intensity |
| 22.8 | 3.890 | 1700 | 40.6% |
| 23.1 | 3.853 | 2000 | 47.7% |
| 23.2 | 3.832 | 4190 | 100.0% |
| 24.6 | 3.616 | 264 | 6.3% |
| 24.8 | 3.590 | 771 | 18.4% |
| 25.2 | 3.535 | 230 | 5.5% |
| 25.5 | 3.489 | 127 | 3.0% |
| 26.1 | 3.410 | 242 | 5.8% |
| 27.8 | 3.207 | 285 | 6.8% |
| 29.6 | 3.015 | 24 | 0.6% |
| 30.8 | 2.901 | 151 | 3.6% |
| 30.9 | 2.896 | 155 | 3.7% |
| 31.2 | 2.861 | 314 | 7.5% |
| 31.6 | 2.830 | 160 | 3.8% |
| 33.1 | 2.707 | 38 | 0.9% |
| 33.7 | 2.658 | 164 | 3.9% |
| 34.2 | 2.621 | 62 | 1.5% |
| 35.0 | 2.561 | 103 | 2.5% |
| 38.6 | 2.331 | 95 | 2.3% |
| 38.9 | 2.311 | 44 | 1.0% |
| 40.7 | 2.216 | 77 | 1.8% |
| 41.6 | 2.171 | 48 | 1.1% |
| 42.4 | 2.129 | 34 | 0.8% |

The invention claimed is:

1. Isolated Methyl 3-[(2-acetylaminoethylthio) carbonyl] propionate (Compound 1) in solid form, having a purity of at least 80% w/w, at least 90% w/w, at least 95% w/w, at least 97% w/w, at least 98% w/w or at least 99% w/w.

2. The isolated Compound 1 according to claim 1, which is in the form of the free form or a salt, hydrate, or solvate thereof.

3. The isolated Compound 1 according to claim 1 having a melting point or a melting range in a range of from 35 to 55° C.

4. The isolated Compound 1 according to claim 1 having an aqueous solubility at room temperature of at least 300 mg/mL.

5. The isolated Compound 1 according to claim 4, wherein the aqueous solubility at room temperature is in a range of from 300 mg/mL to 900 mg/ml.

6. The isolated Compound 1 according to claim 1 having a kinetic aqueous solubility corresponding to a rate constant in a range of from 0.005 to 0.2 $s^{-1}$.

7. A method for treating a metabolic disease, a disease of mitochondrial dysfunction, a disease related to mitochondrial dysfunction, a mitochondrial disorder, mitochondrial energy deficiency, drug-induced mitochondrial side effects, cancer, diabetes, traumatic brain injury, acute liver injury, or atrial fibrillation, said method comprising administering the isolated Compound 1 according to claim 1 to a subject in need thereof.

8. The method according to claim 7 for treating or preventing metabolic dysfunction.

9. The method according to claim 7 for treating or preventing Leigh Syndrome, LHON, MELAS, MERRE (myoclonic epilepsy with ragged red fibers), or other diseases/conditions relating to mitochondrial Complex I defects.

10. A cosmeceutical comprising the isolated Compound 1 according to claim 1.

11. A nutricosmetics comprising the isolated Compound 1 according to claim 1.

12. An energy drink comprising the isolated Compound 1 according to claim 1.

13. A pharmaceutical composition comprising isolated Compound 1 according to claim 1.

14. A process for preparing isolated Compound 1 according to claim 1, said process comprising the steps of:
   a) reacting N-acetyl cysteamine and monomethyl succinate, in the presence of a coupling reagent, in organic solvent, between 0° C. and 100° C.; and
   b) isolating Compound 1.

\* \* \* \* \*